United States Patent
Cook et al.

(10) Patent No.: US 8,927,550 B2
(45) Date of Patent: Jan. 6, 2015

(54) HETEROCYCLIC COMPOUNDS AS CCR1 RECEPTOR ANTAGONISTS

(75) Inventors: Brian Nicholas Cook, Danbury, CT (US); Daniel Kuzmich, Danbury, CT (US)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 95 days.

(21) Appl. No.: 13/502,377

(22) PCT Filed: Oct. 21, 2010

(86) PCT No.: PCT/US2010/053477
§ 371 (c)(1),
(2), (4) Date: May 10, 2012

(87) PCT Pub. No.: WO2011/056440
PCT Pub. Date: May 12, 2011

(65) Prior Publication Data
US 2012/0270879 A1    Oct. 25, 2012

Related U.S. Application Data

(60) Provisional application No. 61/255,153, filed on Oct. 27, 2009.

(51) Int. Cl.
| A61K 31/444 | (2006.01) |
| A61P 37/08 | (2006.01) |
| C07D 401/12 | (2006.01) |
| C07D 209/42 | (2006.01) |
| C07D 471/04 | (2006.01) |

(52) U.S. Cl.
CPC ............ C07D 401/12 (2013.01); C07D 209/42 (2013.01); C07D 471/04 (2013.01)
USPC ........... 514/248; 546/121; 546/201; 546/113; 546/277.4; 548/469; 544/236

(58) Field of Classification Search
None
See application file for complete search history.

(56) References Cited

U.S. PATENT DOCUMENTS

| 4,999,363 | A | 3/1991 | Oshima et al. |
| 5,118,701 | A | 6/1992 | Oshima et al. |
| 5,242,931 | A | 9/1993 | Oshima et al. |
| 5,302,596 | A | 4/1994 | Oshima et al. |
| 5,534,481 | A | 7/1996 | Suzuki et al. |
| 5,612,360 | A | 3/1997 | Boyd et al. |
| 5,616,537 | A | 4/1997 | Yokota et al. |
| 5,670,452 | A | 9/1997 | Suzuki et al. |
| 5,760,028 | A | 6/1998 | Jadhav et al. |
| 5,763,616 | A | 6/1998 | Suzuki et al. |
| 5,770,544 | A | 6/1998 | Yokota et al. |
| 5,973,156 | A | 10/1999 | Chambers et al. |
| 6,025,374 | A | 2/2000 | Castro Pineiro et al. |
| 6,107,321 | A | 8/2000 | Madin |
| 6,211,219 | B1 | 4/2001 | MacLeod et al. |
| 6,326,382 | B1 | 12/2001 | Villalobos et al. |
| 6,331,640 | B1 | 12/2001 | Fotouhi et al. |
| 6,498,255 | B2 | 12/2002 | Villalobos et al. |
| 6,716,978 | B2 | 4/2004 | Marfat |
| 6,784,182 | B2 | 8/2004 | Liebeschuetz et al. |
| 6,803,384 | B2 | 10/2004 | Fotouhi et al. |
| 6,855,715 | B1 | 2/2005 | Liebeschuetz et al. |
| 6,878,725 | B2 | 4/2005 | Liebeschuetz et al. |
| 6,900,196 | B2 | 5/2005 | Liebeschuetz et al. |
| 6,936,611 | B2 | 8/2005 | Liebeschuetz et al. |
| 7,049,297 | B2 | 5/2006 | Zhang et al. |
| 7,053,078 | B2 | 5/2006 | Liebeschuetz et al. |
| 7,129,264 | B2 | 10/2006 | Smallheer et al. |
| 7,223,782 | B2 | 5/2007 | Atkinson et al. |
| 7,429,609 | B2 | 9/2008 | Ohi et al. |
| 7,879,873 | B2 | 2/2011 | Cook et al. |
| 8,008,327 | B2 | 8/2011 | DiSalvo et al. |
| 8,063,065 | B2 | 11/2011 | Cook et al. |
| 8,263,597 | B2 | 9/2012 | Kuzmich et al. |
| 8,293,917 | B2 | 10/2012 | Cook et al. |
| 8,338,610 | B2 | 12/2012 | Kuzmich et al. |

(Continued)

FOREIGN PATENT DOCUMENTS

| EP | 345747 A2 | 12/1989 |
| EP | 1201268 A2 | 5/2002 |

(Continued)

OTHER PUBLICATIONS

Horuk. Chemokine Receptor Antagonist: overcoming developmental hurdles. Nature Reviews Drug Discovery, 2009, vol. 8, pp. 23-33.*
Pease et al. Chemokine receptor antagonist: part 2. Expert Opin. Ther. Patents. 2009, vol. 19, pp. 199-221.*
Gerard et al. Chemokines and disease. Nature Immunology, 2001, vol. 2, pp. 108-115.*
Alzheimer's Disease. Retrieved online Dec. 15, 2010. http:/www.cnn.com/HEALTH/mentalhealt/alzheimers.
Caplus: 1990:478384, Bruneau, 1990.
Caplus: 2008:94643, Kitamura, 2008.
Caplus: 2009:583109, Doherty, 2009.

(Continued)

*Primary Examiner* — Melenie McCormick
*Assistant Examiner* — Taina D Matos Negron
(74) *Attorney, Agent, or Firm* — Michael P. Morris; Anthony P. Bottino

(57) ABSTRACT

Disclosed are CCR1 receptor antagonists of the formula (I) wherein Ar1, Ar2, R1-R3, X and L are disclosed herein. Also disclosed are compositions, methods of making and using compounds of the formula (I).

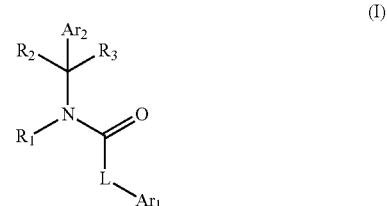

(I)

8 Claims, No Drawings

(56) References Cited

U.S. PATENT DOCUMENTS

| | | | |
|---|---|---|---|
| 2002/0037860 | A1 | 3/2002 | D'Andrea et al. |
| 2002/0052373 | A1 | 5/2002 | Zorn et al. |
| 2004/0127536 | A1 | 7/2004 | Bhagwat et al. |
| 2005/0009876 | A1 | 1/2005 | Bhagwat et al. |
| 2005/0020564 | A1 | 1/2005 | Atkinson et al. |
| 2005/0108582 | A1 | 5/2005 | Fung |
| 2005/0208582 | A1 | 9/2005 | Ohi et al. |
| 2005/0261339 | A1 | 11/2005 | Ohi et al. |
| 2006/0035938 | A1 | 2/2006 | Bladh et al. |
| 2006/0252781 | A1 | 11/2006 | Basarab et al. |
| 2006/0281739 | A1 | 12/2006 | Gadek et al. |
| 2007/0004761 | A1 | 1/2007 | Basarab et al. |
| 2007/0155738 | A1* | 7/2007 | Steeneck et al. ........... 514/230.5 |
| 2008/0262040 | A1 | 10/2008 | Callahan et al. |
| 2008/0280956 | A1 | 11/2008 | Gilligan et al. |
| 2009/0054397 | A1 | 2/2009 | Ohi et al. |
| 2010/0093724 | A1 | 4/2010 | Cook et al. |
| 2011/0034512 | A1 | 2/2011 | Disalvo et al. |
| 2011/0086846 | A1 | 4/2011 | Cook et al. |
| 2011/0137042 | A1 | 6/2011 | Razavi et al. |
| 2011/0230521 | A1 | 9/2011 | Cook et al. |
| 2011/0294808 | A1 | 12/2011 | Kuzmich et al. |
| 2012/0035370 | A1 | 2/2012 | Cook et al. |
| 2012/0136158 | A1 | 5/2012 | Cook et al. |
| 2012/0270870 | A1 | 10/2012 | Cook et al. |
| 2012/0270879 | A1 | 10/2012 | Cook et al. |
| 2012/0322790 | A1 | 12/2012 | Betageri et al. |

FOREIGN PATENT DOCUMENTS

| | | | |
|---|---|---|---|
| JP | 10001478 | A | 1/1998 |
| JP | 2008546794 | A | 12/2008 |
| WO | 9217475 | A1 | 10/1992 |
| WO | 9401415 | A1 | 1/1994 |
| WO | 9500509 | | 5/1995 |
| WO | 9617842 | A1 | 6/1996 |
| WO | 9711945 | A1 | 4/1997 |
| WO | 9719073 | A1 | 5/1997 |
| WO | 9723480 | A1 | 7/1997 |
| WO | 9803504 | A1 | 1/1998 |
| WO | 9923076 | A1 | 5/1999 |
| WO | 0021920 | A1 | 4/2000 |
| WO | 0076970 | A2 | 12/2000 |
| WO | 0076971 | A2 | 12/2000 |
| WO | 0100656 | A2 | 1/2001 |
| WO | 0165218 | A1 | 9/2001 |
| WO | 0210137 | A2 | 2/2002 |
| WO | 03087085 | A1 | 10/2003 |
| WO | 03101968 | A1 | 12/2003 |
| WO | 03105853 | A1 | 12/2003 |
| WO | WO 2004014905 | A1 * | 2/2004 |
| WO | 2004043924 | A1 | 5/2004 |
| WO | 2004056831 | A1 | 7/2004 |
| WO | 2004094372 | A2 | 11/2004 |
| WO | 2005016929 | A1 | 2/2005 |
| WO | 2006091496 | A2 | 8/2006 |
| WO | 2006125119 | A1 | 11/2006 |
| WO | 2007002293 | A2 | 1/2007 |
| WO | 2007028083 | A2 | 3/2007 |
| WO | 2007102883 | A2 | 9/2007 |
| WO | 2008011131 | | 1/2008 |
| WO | 2008089459 | A1 | 7/2008 |
| WO | 2009001129 | A1 | 12/2008 |
| WO | 2009024585 | A2 | 2/2009 |
| WO | 2009037570 | A2 | 3/2009 |
| WO | 2009134666 | A1 | 11/2009 |
| WO | 2009137338 | A1 | 11/2009 |
| WO | WO 2009134666 | A1 * | 11/2009 |
| WO | 2010036632 | A1 | 4/2010 |
| WO | 2011049917 | A1 | 4/2011 |
| WO | 2011056440 | A1 | 5/2011 |
| WO | 2011071730 | A1 | 6/2011 |
| WO | 2011137109 | A1 | 11/2011 |
| WO | 2012087782 | A1 | 6/2012 |

OTHER PUBLICATIONS

Carter, P.H. et al., "N-aryl pyrazoles, indazoles and azaindazoles as antagonists of CC chemokine receptor 1: patent cooperation treaty applications WO2010036632, WO2009134666 and WO2009137337". Expert Opinion Ther. Patents, 2010, 20(11), p. 1-10.

Cheng, J-F, et al., "CCR1 Antagonists". Molecular Diversity, Kluwer Academic Publishers, vol. 12, No. 1, Jun. 17, 2008, p. 17-23.

Conlon, K. et al., "Comparison of lymphokine secretion and mRNA expression in the CD45RA+ and CD45RO+ subsets of human peripheral blood CD4+ and CD8+ lympocytes". European Journal of Immunology, 1995, vol. 25, p. 644-648.

Finar, I.L. et al. The Beckmann Rearrangement of Some Pyrazolyl Oximes. Journal Chemical Soc. Sec. C, 1969, p. 1495-1499.

Gerard, C. et al., "Chemokines and disease". 2001 Nature Publishing Group, Chemokine Reviews, Nature Immunology, vol. 2, No. 2, Feb. 2001, p. 108-115.

Haringman, J.J. et al., "Chemokine blockade and chronic inflammatory disease: proof of concept in patients with rheumatoid arthritis". Ann Rheum Dis, 2003, 62, p. 715-721.

International Search Report and Written Opinion for PCT/US2010/053477 mailed Apr. 21, 2011.

Karpus, W. J. et al., "An Important Role for the Chemokine Macrophase Inflammatory Protein-1a in the Pathogenesis of the T Cell-Mediated Autoimmune Disease, Experimental Autoimmune Encephalomyelitis". The American Association of Immunologists, 1995, p. 5003-5010.

Koch, A. E., et al., "Macrophase Inflammatory Protein-1a. A Novel Chemotactic Cytokine for Macrophages in Rheumatoid Arthritis". The Journal of Clinical Investigation, Inc., vol. 93, Mar. 1994, p. 921-928.

Koch, A.E. et al., "Epithelial Neutrophil Activating Peptide-78: A Novel Chemotactic Cytokine for Neutrophils in Arthritis". The Journal of Clinical Investigations, Inc. vol. 94, Sep. 1994, p. 1012-1018.

Plater-Zyberk, C. et al., "Effect of a CC chemokine receptor antagonist on collagen induced arthritis in DBA/1 mice". Immunology Letters, 57, 1997, p. 117-120.

Revesz, L. et al., "Novel CCR1 antagonists with oral activity in the mouse collagen induced arthritis". Bioorganice and Medicinal Chemistry Letters, 2005, p. 1-5.

Trebst, C. et al., "CCR1+/CCR5+ Mononuclear Phagocytes Accumulate in the Central Nervous System on Patients with Multiple Sclerosis." American Journal of Pathology, vol. 159, No. 4, Nov. 2001, p. 1701-1710.

Volin, M.V. et al., "RANTES Expression and Contribution to Monocyte Chemotaxix in Arthritis". Clinical Immunology and Immunopathology, vol. 89, No. 1, Oct. 1998, Article II984590, p. 44-53.

Caplus: 2009:2329372, Loiseleur, 2009.

Engbersen, J.F.J. et al., "Synthesis of 2-Aminomethyl-1,10-phenanthroline. A new Chelating Agent and Versatile Synthon for other Chelating Compounds", Journal of Heterocyl Cehm., 1986, vol. 23, pp. 989-990.

Berge, S. M. et al., "Pharmaceuticals Salts", Journal of Pharmaceutical Sciences, Jan. 1977, vol. 66, No. 1, pp. 1-19.

International Search Report and Written Opinion for PCT/US2011/033923 mailed Oct. 6, 2011.

International Search Report and Written Opinion for PCT/US2010/058594 mailed Jan. 25, 2011.

International Search Report and Written Opinion for PCT/US2011/065350 mailed Feb. 22, 2012.

International Search Report for PCT/US2009/041485 mailed Jun. 29, 2009.

International Search Report for PCT/US2009/057778 mailed Jan. 11, 2010.

International Search Report/Written Opinion for PCT/US2009/042455 mailed Jul. 13, 2009.

International Search Report/Written Opinion for PCT/US2010/053142 mailed Dec. 27, 2010.

Tak, P. et al., "Chemokine receptor CCR1 antagonist CCX354-C treatment for rheumatoid arthritis: CARAT-2, a randomised, placebo controlled clinical trial." 2012, Ann Rheum Dis., pp. 1-10.

* cited by examiner

HETEROCYCLIC COMPOUNDS AS CCR1 RECEPTOR ANTAGONISTS

APPLICATION DATA

This application claims benefit to U.S. provisional application Ser. No. 61/255,153 filed Oct. 27, 2009.

FIELD OF THE INVENTION

This invention relates to heterocyclic compounds (fused 6,5 ring systems) that are useful as antagonists of CCR1 activity and are thus useful for treating a variety of diseases and disorders that are mediated or sustained through the activity of CCR1 including autoimmune diseases, such as rheumatoid arthritis and multiple sclerosis. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Chemotactic Cytokine Receptor 1 (CCR1) belongs to a large family (>20) of chemotactic cytokine (chemokine) receptors that interact with specific chemokines (>50) to mediate leukocyte trafficking, granule exocytosis, gene transcription, mitogenic effects and apoptosis. Chemokines are best known for their ability to mediate basal and inflammatory leukocyte trafficking. The binding of at least three chemokines (MIP-1 alpha/CCL3, MCP3/CCL7 and RANTES/CCL5) to CCR1 is responsible for the trafficking of monocytes, macrophages and TH1 cells to inflamed tissues of rheumatoid arthritis (RA) and multiple sclerosis (MS) patients (Trebst et al. (2001) *American J of Pathology* 159 p. 1701). Macrophage inflammatory protein 1 alpha (MIP-1 alpha), macrophage chemoattractant protein 3 (MCP-3) and regulated on activation, normal T-cell expressed and secreted (RANTES) are all found in the CNS of MS patients, while MIP-1 alpha and RANTES are found in the CNS in the experimental autoimmune encephalomyelitis (EAE) model of MS (Review: Gerard and Rollins (2001) *Nature Immunology*). Macrophages and Th1 cells in the inflamed synovia of RA patients are also major producers of MIP-1 alpha and RANTES, which continuously recruit leukocytes to the synovial tissues of RA patients to propagate chronic inflammation (Volin et al. (1998) *Clin. Immunol. Immunopathology*; Koch et al. (1994) *J. Clin. Investigation*; Conlon et al. (1995) *Eur. J. Immunology*). Antagonizing the interactions between CCR1 and its chemokine ligands is hypothesized to block chemotaxis of monocytes, macrophages and Th1 cells to inflamed tissues and thereby ameliorate the chronic inflammation associated with autoimmune diseases such as RA and MS.

Evidence for the role of CCR1 in the development and progression of chronic inflammation associated with experimental autoimmune encephalitis (EAE), a model of multiple sclerosis, is based on both genetic deletion and small molecule antagonists of CCR1. CCR1 deficient mice were shown to exhibit reduced susceptibility (55% vs. 100%) and reduced severity (1.2 vs. 2.5) of active EAE (Rottman et al. (2000) *Eur. J. Immunology*). Furthermore, administration of small molecule antagonist of CCR1, with moderate affinity ($K_i$=120 nM) for rat CCR1, was shown to delay the onset and reduce the severity of EAE when administered intravenously (Liang et al. (2000) *J. Biol. Chemistry*). Treatment of mice with antibodies specific for the CCR1 ligand MIP-1 alpha have also been shown to be effective in preventing development of acute and relapsing EAE by reducing the numbers of T cells and macrophages recruited to the CNS (Karpus et al. (1995) *J. Immunology*; Karpus and Kennedy (1997) *J. Leukocyte Biology*). Thus, at least one CCR1 ligand has been demonstrated to recruit leukocytes to the CNS and propagate chronic inflammation in EAE, providing further in vivo validation for the role of CCR1 in EAE and MS.

In vivo validation of CCR1 in the development and propagation of chronic inflammation associated with RA is also significant. For example, administration of a CCR1 antagonist in the collagen induced arthritis model (CIA) in DBA/1 mice has been shown to be effective in reducing synovial inflammation and joint destruction (Plater-Zyberk et al. (1997) *Immunology Letters*). Another publication described potent antagonists of murine CCR1 that reduced severity (58%) in LPS-accelerated collagen-induced arthritis (CIA), when administered orally (*Biorganic and Medicinal Chemistry Letters* 15, 2005, 5160-5164). Published results from a Phase Ib clinical trial with an oral CCR1 antagonist demonstrated a trend toward clinical improvement in the absence of adverse side effects (Haringman et al. (2003) *Ann. Rheum. Dis.*). One third of the patients achieved a 20% improvement in rheumatoid arthritis signs and symptoms (ACR20) on day 18 and CCR1 positive cells were reduced by 70% in the synovia of the treated patients, with significant reduction in specific cell types including 50% reduction in $CD4^+$ T cells, 50% reduction in $CD8^+$ T cells and 34% reduction in macrophages.

Studies such as those cited above support a role for CCR1 in MS and RA and provide a therapeutic rationale for the development of CCR1 antagonists.

BRIEF SUMMARY OF THE INVENTION

The present invention provides novel compounds which block the interaction of CCR1 and its ligands and are thus useful for treating a variety of diseases and disorders that are mediated or sustained through the activity of CCR1 including autoimmune diseases, such as rheumatoid arthritis and multiple sclerosis. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In its broadest generic aspect the invention provides a compound of the formula (I)

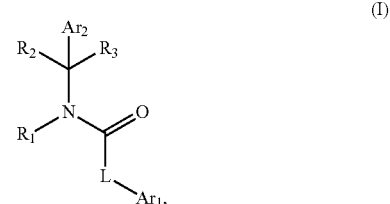

wherein:
L is selected from

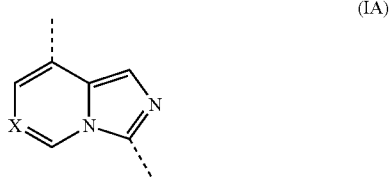

(IB)

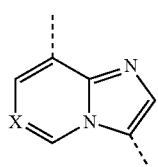

(IC)

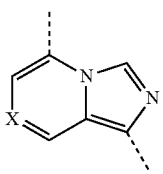

(ID)

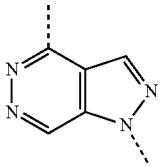

(IE)

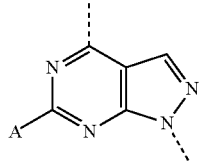

(IF)

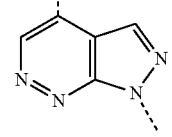

(IG)

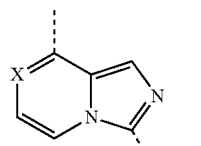
and (IH)

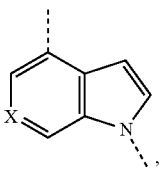, wherein $Ar_1$ is connected to the 5-member ring within L and wherein —C(O)N($R_1$)C$R_2R_3Ar_2$ is connected to the 6-member ring contained within L;

X is N or C-A;

A is selected from hydrogen, methyl, trifluoromethyl, halogen, hydroxyl, cyano and $C_1$-$C_5$ alkylthio wherein the sulfur atom is optionally oxidized to a sulfoxide or sulfone;

$Ar_1$ is carbocycle, heteroaryl or heterocyclyl each optionally substituted by one to three $R_a$;

$Ar_2$ is carbocycle, heteroaryl or heterocyclyl, each optionally substituted by one to three $R_b$;

$R_1$ is hydrogen, $C_{1-6}$ alkyl or $C_{1-6}$ alkoxy$C_{1-6}$ alkyl;

$R_2$, $R_3$ are each independently hydrogen, $C_{1-6}$ alkyl or $C_{1-6}$ alkenyl, wherein the $C_{1-6}$ alkyl or alkenyl is optionally partially or fully halogenated or substituted with one to three groups independently selected from cyano, $C_{1-6}$ alkoxy, hydroxyl, —CO$_2C_{1-6}$ alkyl, —C(O)N($R_e$)($R_f$), —N($R_e$)($R_f$) and heterocyclyl optionally substituted by oxo; or $R_2$ and $R_3$ together with the carbon atom they are commonly attached to form a $C_3$-$C_6$ cycloalkyl ring;

$R_a$ is $C_{1-6}$ alkyl, $C_{3-10}$ cycloalkyl, $C_{1-6}$ alkoxy, $C_{1-6}$ alkylthio, $C_{1-6}$ alkylsulfonyl, $C_{1-6}$ alkoxycarbonyl, amino, mono- or di-$C_{1-6}$ alkylamino, $C_{3-6}$ cycloalkylamino, $C_{1-6}$ alkylaminocarbonyl, $C_{1-6}$ acyl, $C_{1-6}$ acylamino, $C_{1-6}$ dialkylaminocarbonyl, hydroxyl, halogen, cyano, nitro, oxo, $R_4$—S(O)$_m$—NH—, $R_4$—NH—S(O)$_m$—, aryl or carboxyl;

$R_b$ is hydroxyl, carboxyl, halogen, —(CH$_2$)$_n$—CN, —(CH$_2$)$_n$—CO$_2C_{1-6}$alkyl, nitro, $C_{1-6}$ alkyl, $C_{2-6}$ alkenyl, $C_{2-6}$ alkynyl, $C_{3-10}$ cycloalkyl, $C_{1-6}$ alkoxy, $C_{1-6}$alkylC(O)—, —(CH$_2$)$_n$—N$R_cR_d$, $R_4$—S(O)$_m$(CH$_2$)$_{0-1}$—, $R_4$—S(O)$_m$—N$R_e$—, $R_4$—NR$_e$—S(O)$_m$(CH$_2$)$_{0-1}$—, —N$R_f$—C(O)—$R_e$, —(CH$_2$)$_y$—C(O)—(CH$_2$)$_n$—NR$_c$R$_d$, heterocyclyl, aryl or heteroaryl, each $R_b$ where possible is optionally halogenated or substituted with 1 to 3$C_{1-6}$ alkyl, hydroxyl, $C_{1-6}$ acyl, $C_{1-6}$ alkoxycarbonyl, $C_{1-6}$ alkyl-S(O)$_m$—, aryl or carboxyl;

each $R_c$, $R_d$ are independently hydrogen, $C_{1-6}$ alkyl, $C_{1-6}$ acyl, $C_{3-10}$ cycloalkyl, $C_{1-6}$ alkoxy, hydroxy$C_{1-6}$ alkyl, cyano-$C_{1-6}$ alkyl, $C_{1-6}$ alkyl$C_{1-6}$ alkoxy, $C_{1-6}$ alkylsulfonyl, $C_{1-6}$ alkoxycarbonyl$C_{0-3}$alkyl, —(CH$_2$)$_n$—C(O)—NR$_e$R$_f$ or —(CH$_2$)$_n$—NR$_e$R$_f$;

each $R_e$, $R_f$ are independently hydrogen, $C_{1-6}$ alkyl, $C_{3-10}$ cycloalkyl, $C_{1-6}$ alkoxy, $C_{1-6}$ alkoxy$C_{1-6}$alkyl, mono- or di $C_{1-6}$alkylamino$C_{1-6}$alkyl, hydroxy$C_{1-6}$ alkyl or $C_{1-6}$ acyl;

$R_4$ is hydrogen, $C_{1-6}$ alkyl, $C_{3-6}$cycloalkyl, heterocyclyl (CH$_2$)$_{0-1}$, mono- or di-$C_{1-6}$ alkylamino, mono- or di-$_{1-6}$alkylamino(CH$_2$)$_{2-3}$N(R$_e$)—, aryl or heteroaryl each optionally substituted with 1 to 3$C_{1-6}$ alkyl, $C_{3-6}$cycloalkyl, $C_{1-6}$alkoxy, halogen, hydroxyl, oxo, carboxyl, —C(O)NR$_e$R$_f$, amino, mono- or di-$C_{1-6}$ alkylamino, $C_{1-6}$ alkoxycarbonyl or $C_{1-6}$ acylamino;

each n, y are independently 0-3;

each m is independently 0-2;

or a pharmaceutically acceptable salt thereof.

In another embodiment of the invention there is provided a compound of the formula (I) as provided immediately above, and wherein X is N or C-A;

A is selected from hydrogen, methyl, trifluoromethyl, hydroxyl, cyano and $C_1$-$C_5$ alkylthio wherein the sulfur atom is optionally oxidized to a sulfoxide or sulfone;

$Ar_1$ is phenyl, cyclohexyl or tetrahydropyranyl each optionally substituted by one to three $R_a$;

$Ar_2$ is phenyl, pyridinyl, pyrimidinyl, thiophenyl, thiazolyl, oxazolyl, pyrazolyl, imidazolyl, cyclohexyl, piperidinyl, morpholinyl or piperazinyl, each optionally substituted by one to three $R_b$;

$R_1$ is hydrogen;

$R_2$, $R_3$ are each independently hydrogen or $C_{1-6}$ alkyl, wherein the $C_{1-6}$ alkyl is optionally partially or fully halogenated or substituted with one to three groups independently selected from cyano, $C_{1-6}$ alkoxy and hydroxyl; or $R_2$ and $R_3$ together with the carbon atom they are commonly attached to form a $C_{3-4}$ cycloalkyl ring;

$R_a$ is $C_{1-6}$ alkyl, hydroxyl, halogen, cyano or nitro;

$R_b$ is hydroxyl, carboxyl, halogen, $C_{1-6}$ alkyl, $C_{1-6}$ alkoxy, $C_{1-6}$alkylC(O)—, $R_4$—S(O)$_m$(CH$_2$)$_{0-1}$—, $R_4$—S(O)$_m$—NR$_e$— or $R_4$—NR$_e$—S(O)$_m$(CH$_2$)$_{0-1}$—, each $R_b$ where possible is optionally halogenated or substituted with 1 to 3$C_{1-6}$ alkyl, hydroxyl, $C_{1-6}$ acyl, $C_{1-6}$ alkoxycarbonyl, $C_{1-6}$ alkyl-S(O)$_m$— or carboxyl;

each $R_e$ is hydrogen, $C_{1-6}$ alkyl, $C_{3-10}$ cycloalkyl, $C_{1-6}$ alkoxy, $C_{1-6}$ alkoxyC$_{1-6}$alkyl, mono- or diC$_{1-6}$alkylamino C$_{1-6}$alkyl, hydroxyC$_{1-6}$ alkyl or $C_{1-6}$ acyl;

$R_4$ is hydrogen, $C_{1-6}$ alkyl, $C_{3-6}$cycloalkyl, piperidinyl, morpholinyl, tetrahydropyranyl, pyrrolidinyl, mono- or di-$C_{1-6}$ alkylamino, mono- or di-$_{1-6}$alkylamino(CH$_2$)$_{2-3}$N(R$_e$)—, aryl or heteroaryl each optionally substituted with 1 to 3$C_{1-6}$ alkyl, $C_{3-6}$cycloalkyl, carboxyl;

or a pharmaceutically acceptable salt thereof.

In another embodiment of the invention there is provided a compound of the formula (I) according to any of the embodiments described herein, and wherein X is N or C-A;

A is selected from hydrogen and cyano;

An$_1$ is phenyl is substituted by one to two $R_a$;

Ar$_2$ is phenyl, pyridinyl, or thiazolyl, each optionally substituted by one to two $R_b$;

$R_2$, $R_3$ are each independently hydrogen or $C_{1-3}$ alkyl; or $R_2$ and $R_3$ together with the carbon atom they are commonly attached to form a $C_3$ cycloalkyl ring;

$R_a$ is $C_{1-6}$ alkyl, halogen or cyano;

$R_b$ is halogen, $C_{1-3}$ alkyl, $R_4$—S(O)$_m$(CH$_2$)$_{0-1}$—, $R_4$—S(O)$_m$—NR$_e$—, or $R_4$—NR$_e$—S(O)$_m$(CH$_2$)$_{0-1}$—, each $R_b$ where possible is optionally halogenated;

each $R_e$ is hydrogen;

$R_4$ is $C_{1-6}$ alkyl or piperidinyl each optionally substituted with 1 to 3$C_{1-3}$ alkyl;

each m is 2.

In a further embodiment of the invention there is provided a compound of the formula (I) according to any of the embodiments described herein, and wherein $R_a$ is —F;

$R_b$ is $R_4$—S(O)$_2$(CH$_2$)$_{0-1}$—, $R_4$—S(O)$_2$—NR$_e$—, or $R_4$—NR$_e$—S(O)$_2$(CH$_2$)$_{0-1}$—, CF$_3$ or Br;

$R_4$ is $C_{1-3}$ alkyl or piperidinyl each optionally substituted with —CH$_3$;

In a further embodiment of the invention there is provided a compound of the formula (I) according to any of the embodiments described herein, and wherein L is selected from

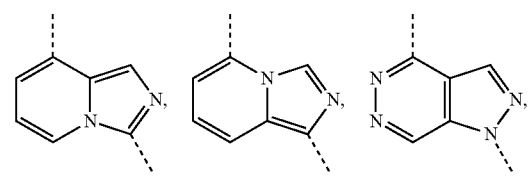

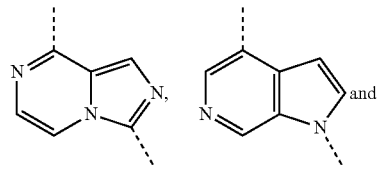

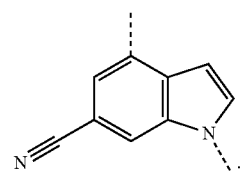

In a further embodiment of the invention there is provided a compound of the formula (I) according to any of the embodiments described herein, and wherein Ar$_2$ is

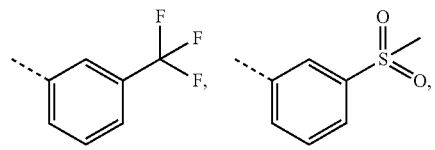

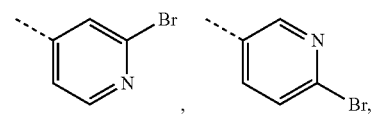

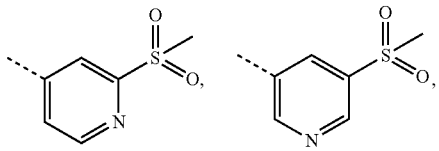

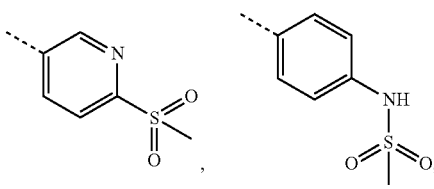

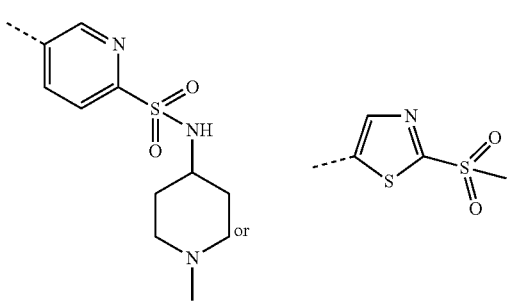

In a another embodiment of the invention there is provided a compound of the formula (I) as provided in Table I which can be made according to the general schemes and specific examples and methods known in the art.

TABLE I

| Structure | Name | HPLC-MS Data [a] | |
|---|---|---|---|
| | | Observed Mass [b] | rt (min) |
| 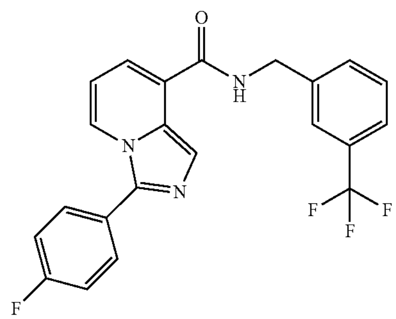 [SMILES: O=C(NCc1cccc(C(F)(F)F)c1)c1cccn2c(-c3ccc(F)cc3)ncc12] | 3-(4-Fluorophenyl)-imidazo[1,5-a]pyridine-8-carboxylic acid 3-trifluoromethyl-benzylamide | 414.5 | 1.56 |
| 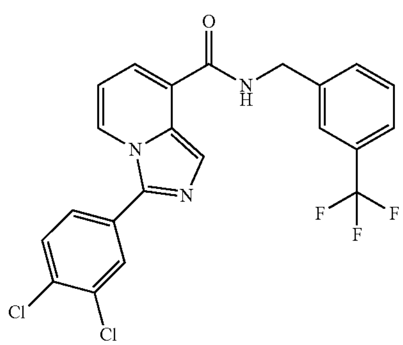 [SMILES: O=C(NCc1cccc(C(F)(F)F)c1)c1cccn2c(-c3ccc(Cl)c(Cl)c3)ncc12] | 3-(3,4-Dichlorophenyl)-imidazo[1,5-a]pyridine-8-carboxylic acid 3-trifluoromethyl-benzylamide | 464.4 | 1.82 |
| 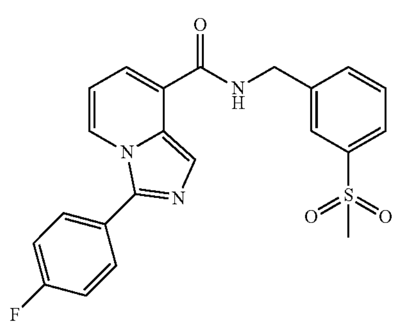 [SMILES: CS(=O)(=O)c1cccc(CNC(=O)c2cccn3c(-c4ccc(F)cc4)ncc23)c1] | 3-(4-Fluorophenyl)-imidazo[1,5-a]pyridine-8-carboxylic acid 3-methanesulfonyl-benzylamide | 424.6 | 1.22 |
| 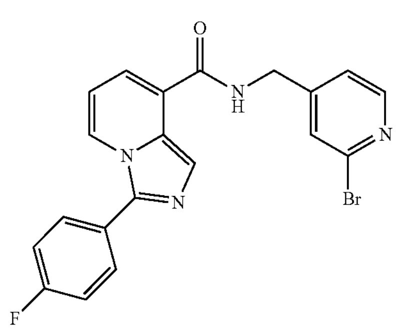 [SMILES: O=C(NCc1ccnc(Br)c1)c1cccn2c(-c3ccc(F)cc3)ncc12] | 3-(4-Fluorophenyl)-imidazo[1,5-a]pyridine-8-carboxylic acid (2-bromopyridin-4-ylmethyl)-amide | 425.5 427.5 | 1.26 |

TABLE I-continued

| Structure | Name | HPLC-MS Data [a] | |
|---|---|---|---|
| | | Observed Mass [b] | rt (min) |
| 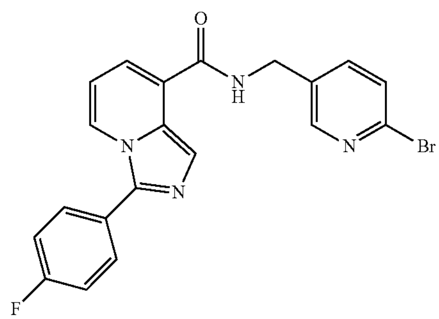 [SMILES: O=C(NCc1ccc(Br)nc1)c1cccn2c(-c3ccc(F)cc3)ncc12] | 3-(4-Fluorophenyl)-imidazo[1,5-a]pyridine-8-carboxylic acid (6-bromopyridin-3-ylmethyl)-amide | 425.5 427.5 | 1.29 |
| 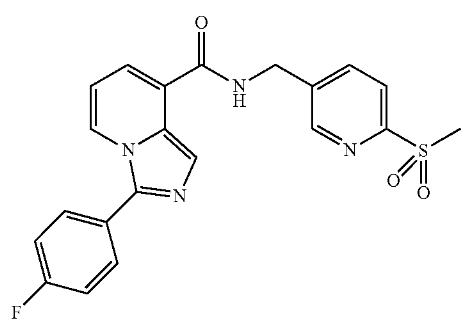 [SMILES: CS(=O)(=O)c1ccc(CNC(=O)c2cccn3c(-c4ccc(F)cc4)ncc23)cn1] | 3-(4-Fluorophenyl)-imidazo[1,5-a]pyridine-8-carboxylic acid (6-methanesulfonyl-pyridin-3-ylmethyl)-amide | 425.5 | 1.14 |
| 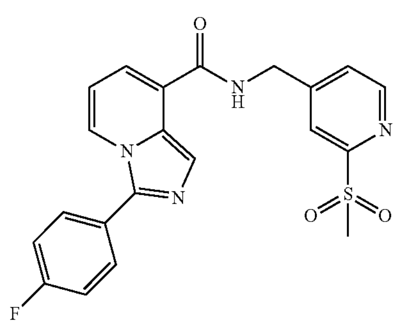 [SMILES: CS(=O)(=O)c1cc(CNC(=O)c2cccn3c(-c4ccc(F)cc4)ncc23)ccn1] | 3-(4-Fluorophenyl)-imidazo[1,5-a]pyridine-8-carboxylic acid (2-methanesulfonyl-pyridin-4-ylmethyl)-amide | 425.5 | 1.14 |
| 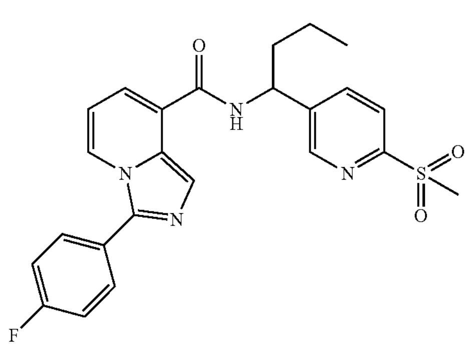 [SMILES: CCCC(NC(=O)c1cccn2c(-c3ccc(F)cc3)ncc12)c1ccc(S(C)(=O)=O)nc1] | 3-(4-Fluorophenyl)-imidazo[1,5-a]pyridine-8-carboxylic acid [1-(6-methanesulfonyl-pyridin-3-yl)-butyl]-amide | 467.6 | 1.34 |

TABLE I-continued

| Structure | Name | HPLC-MS Data [a] | |
|---|---|---|---|
| | | Observed Mass [b] | rt (min) |
| 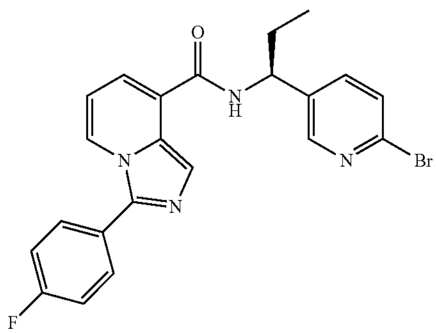 [SMILES: CC[C@H](NC(=O)c1cccn2c(-c3ccc(F)cc3)ncc12)c1ccc(Br)nc1] | 3-(4-Fluorophenyl)-imidazo[1,5-a]pyridine-8-carboxylic acid [(S)-1-(6-bromopyridin-3-yl)-propyl]-amide | 453.6 455.6 | 1.42 |
| 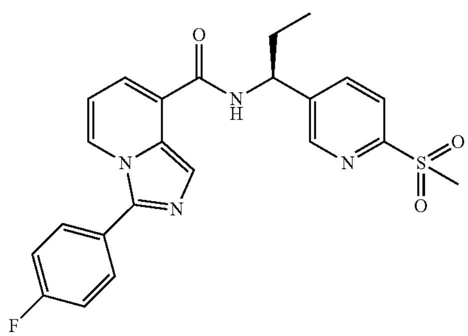 [SMILES: CC[C@H](NC(=O)c1cccn2c(-c3ccc(F)cc3)ncc12)c1ccc(S(C)(=O)=O)nc1] | 3-(4-Fluorophenyl)-imidazo[1,5-a]pyridine-8-carboxylic acid [(S)-1-(6-methanesulfonyl-pyridin-3-yl)-propyl]-amide | 453.8 | 1.24 |
| 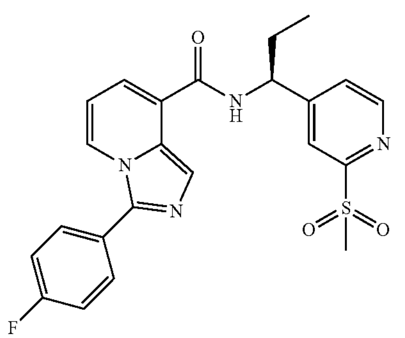 [SMILES: CC[C@H](NC(=O)c1cccn2c(-c3ccc(F)cc3)ncc12)c1ccnc(S(C)(=O)=O)c1] | 3-(4-Fluorophenyl)-imidazo[1,5-a]pyridine-8-carboxylic acid [(S)-1-(2-methanesulfonyl-pyridin-4-yl)-propyl]-amide | 453.7 | 1.26 |
| 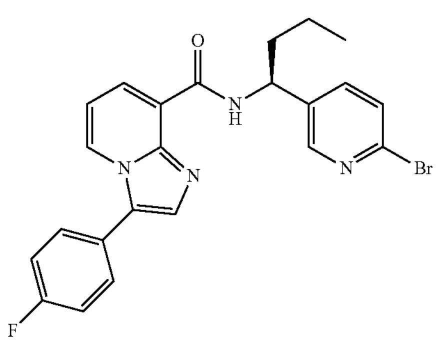 [SMILES: CCC[C@H](NC(=O)c1cccn2c(-c3ccc(F)cc3)cnc12)c1ccc(Br)nc1] | 3-(4-Fluorophenyl)-imidazo[1,2-a]pyridine-8-carboxylic acid [(S)-1-(6-bromopyridin-3-yl)-butyl]-amide | 467.6 469.6 | 1.89 |

TABLE I-continued

| Structure | Name | HPLC-MS Data [a] | |
|---|---|---|---|
| | | Observed Mass [b] | rt (min) |
| 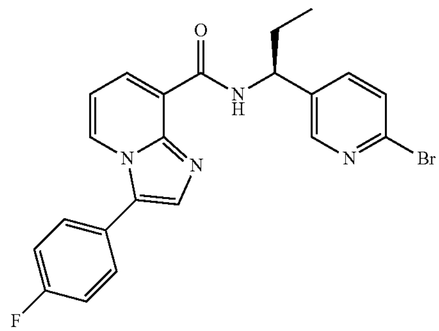 [SMILES: CC[C@H](NC(=O)c1cccn2c(-c3ccc(F)cc3)cnc12)c1ccc(Br)nc1] | 3-(4-Fluorophenyl)-imidazo[1,2-a]pyridine-8-carboxylic acid [(S)-1-(6-bromopyridin-3-yl)-propyl]-amide | 453.6 455.5 | 1.77 |
| 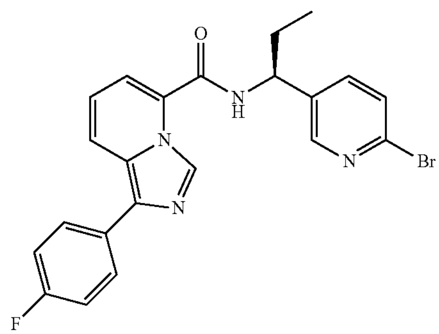 [SMILES: CC[C@H](NC(=O)c1cccc2c(-c3ccc(F)cc3)ncn12)c1ccc(Br)nc1] | 1-(4-Fluorophenyl)-imidazo[1,5-a]pyridine-5-carboxylic acid [(S)-1-(6-bromopyridin-3-yl)-propyl]-amide | 453.6 457.6 | 1.65 |
| 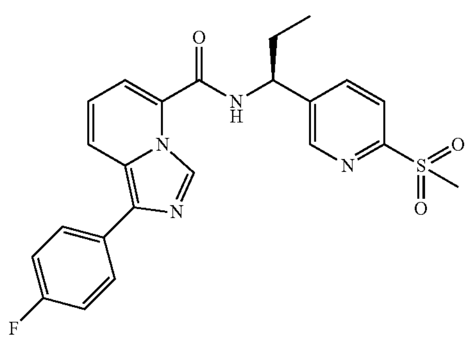 [SMILES: CC[C@H](NC(=O)c1cccc2c(-c3ccc(F)cc3)ncn12)c1ccc(S(C)(=O)=O)nc1] | 1-(4-Fluorophenyl)-imidazo[1,5-a]pyridine-5-carboxylic acid [(S)-1-(6-methanesulfonyl-pyridin-3-yl)-propyl]-amide | 453.7 | 1.46 |
| 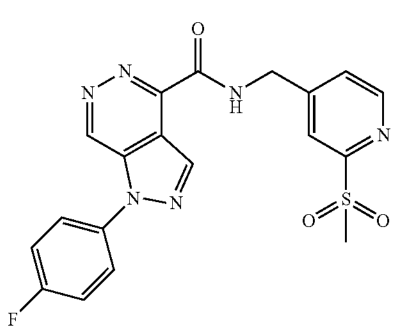 [SMILES: CS(=O)(=O)c1cc(CNC(=O)c2nncc3c2cnn3-c2ccc(F)cc2)ccn1] | 1-(4-Fluorophenyl)-1H-pyrazolo[3,4-d]pyridazine-4-carboxylic acid (2-methanesulfonyl-pyridin-4-ylmethyl)-amide | 427.7 | 1.38 |

TABLE I-continued

| Structure | Name | Observed Mass | rt (min) |
|---|---|---|---|
| 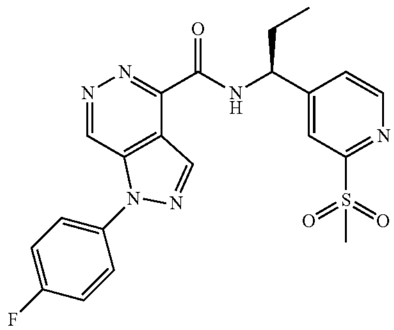 [SMILES: CC[C@H](NC(=O)c1nncc2c1cnn2-c1ccc(F)cc1)c1ccnc(S(C)(=O)=O)c1] | 1-(4-Fluorophenyl)-1H-pyrazolo[3,4-d]pyridazine-4-carboxylic acid [(S)-1-(2-methanesulfonyl-pyridin-4-yl)-propyl]-amide | 455.7 | 1.51 |
| 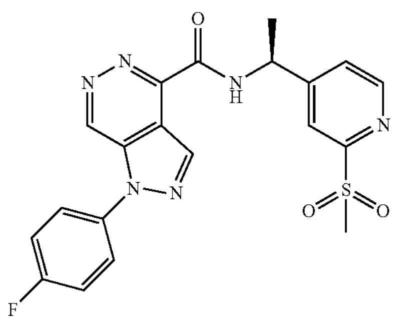 [SMILES: C[C@H](NC(=O)c1nncc2c1cnn2-c1ccc(F)cc1)c1ccnc(S(C)(=O)=O)c1] | 1-(4-Fluorophenyl)-1H-pyrazolo[3,4-d]pyridazine-4-carboxylic acid [(S)-1-(2-methanesulfonyl-pyridin-4-yl)-ethyl]-amide | 441.7 | 1.43 |
| 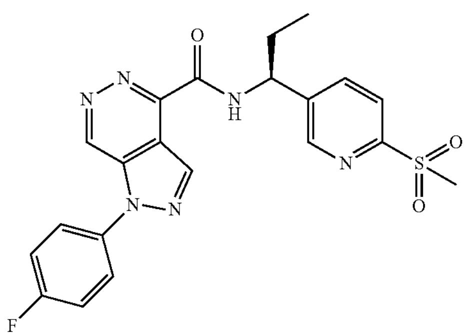 [SMILES: CC[C@H](NC(=O)c1nncc2c1cnn2-c1ccc(F)cc1)c1ccc(S(C)(=O)=O)nc1] | 1-(4-Fluorophenyl)-1H-pyrazolo[3,4-d]pyridazine-4-carboxylic acid [(S)-1-(6-methanesulfonyl-pyridin-3-yl)-propyl]-amide | 455.7 | 1.51 |
| 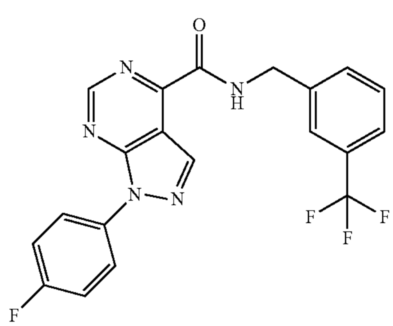 [SMILES: O=C(NCc1cccc(C(F)(F)F)c1)c1ncnc2c1cnn2-c1ccc(F)cc1] | 1-(4-Fluorophenyl)-1H pyrazolo[3,4-d]pyrimidine-4-carboxylic acid 3-trifluoromethyl-benzylamide | 416.4 | 1.98 |

TABLE I-continued

| Structure | Name | HPLC-MS Data [a] | |
|---|---|---|---|
| | | Observed Mass [b] | rt (min) |
| 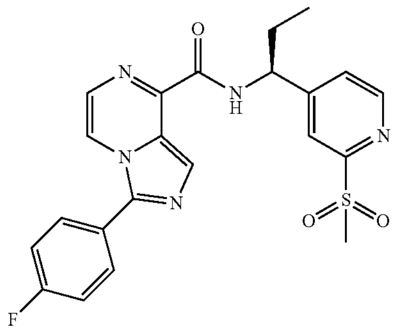 [SMILES: CC[C@H](NC(=O)c1nccn2c(-c3ccc(F)cc3)ncc12)c1ccnc(S(C)(=O)=O)c1] | 3-(4-Fluorophenyl)-imidazo[1,5-a]pyrazine-8-carboxylic acid [(S)-1-(2-methanesulfonyl-pyridin-4-yl)-propyl]-amide | 453.9 | 1.46 |
| 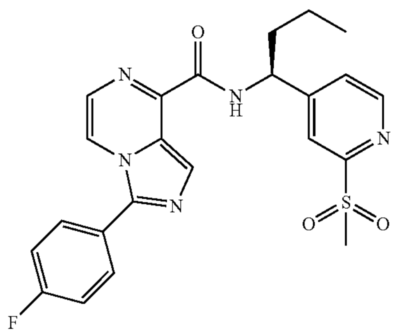 [SMILES: CCC[C@H](NC(=O)c1nccn2c(-c3ccc(F)cc3)ncc12)c1ccnc(S(C)(=O)=O)c1] | 3-(4-Fluorophenyl)-imidazo[1,5-a]pyrazine-8-carboxylic acid [(S)-1-(2-methanesulfonyl-pyridin-4-yl)-butyl]-amide | 468.1 | 1.53 |
| 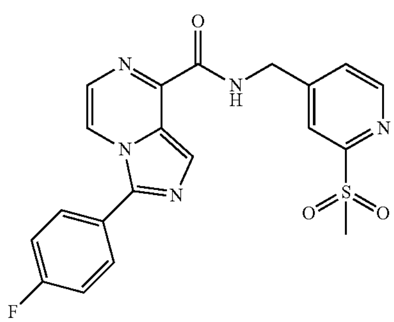 [SMILES: CS(=O)(=O)c1cc(CNC(=O)c2nccn3c(-c4ccc(F)cc4)ncc23)ccn1] | 3-(4-Fluorophenyl)-imidazo[1,5-a]pyrazine-8-carboxylic acid (2-methanesulfonyl-pyridin-4-ylmethyl)-amide | 426.2 | 1.36 |
| 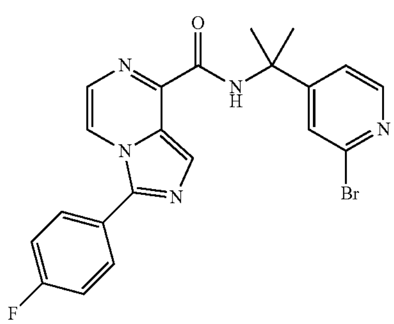 [SMILES: CC(C)(NC(=O)c1nccn2c(-c3ccc(F)cc3)ncc12)c1ccnc(Br)c1] | 3-(4-Fluorophenyl)-imidazo[1,5-a]pyrazine-8-carboxylic acid [1-(2-bromopyridin-4-yl)-1-methyl-ethyl]-amide | 454.1 456.1 | 1.62 |

TABLE I-continued

| Structure | Name | Observed Mass [b] | rt (min) |
|---|---|---|---|
| 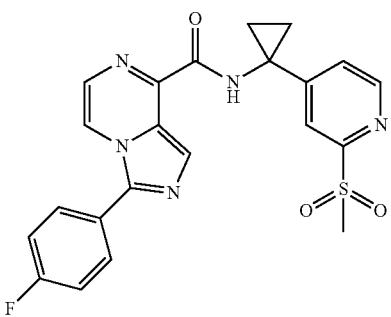 [SMILES: CS(=O)(=O)c1cc(C2(NC(=O)c3nccn4c(-c5ccc(F)cc5)ncc34)CC2)ccn1] | 3-(4-Fluorophenyl)-imidazo[1,5-a]pyrazine-8-carboxylic acid [1-(2-methanesulfonyl-pyridin-4-yl)-cyclopropyl]-amide | 452.1 | 1.42 |
| 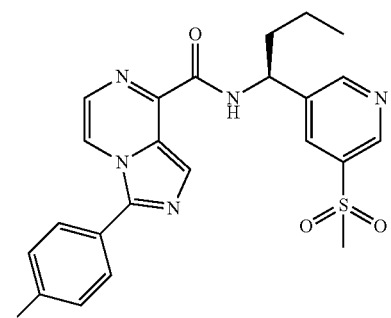 | 3-(4-Fluorophenyl)-imidazo[1,5-a]pyrazine-8-carboxylic acid [(S)-1-(5-methanesulfonyl-pyridin-3-yl)-butyl]-amide | 468.1 | 1.51 |
| 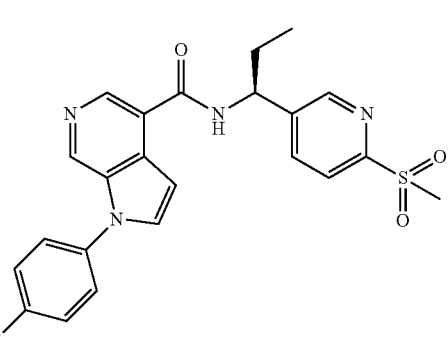 | 1-(4-Fluorophenyl)-1H-pyrrolo[2,3-c]pyridine-4-carboxylic acid [(S)-1-(6-methanesulfonyl-pyridin-3-yl)-propyl]-amide | 453.8 | 1.13 |
| 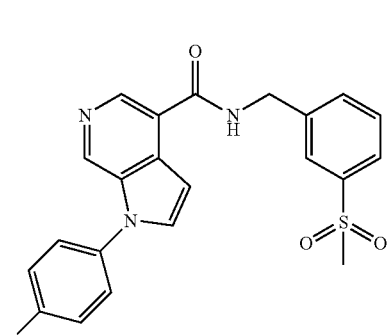 | 1-(4-Fluorophenyl)-1H-pyrrolo[2,3-c]pyridine-4-carboxylic acid 3-methanesulfonyl-benzylamide | 424.7 | 0.25 |

TABLE I-continued

| Structure | Name | HPLC-MS Data [a] | |
|---|---|---|---|
| | | Observed Mass [b] | rt (min) |
| 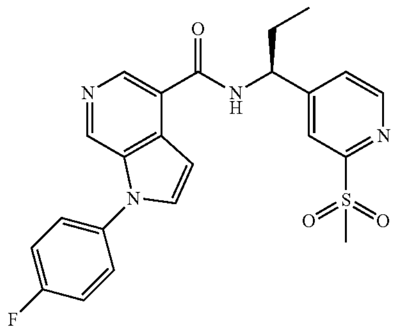 [SMILES: CC[C@H](NC(=O)c1cncc2c1ccn2-c1ccc(F)cc1)c1ccnc(S(C)(=O)=O)c1] | 1-(4-Fluorophenyl)-1H-pyrrolo[2,3-c]pyridine-4-carboxylic acid [(S)-1-(2-methanesulfonyl-pyridin-4-yl)-propyl]-amide | 453.7 | 1.13 |
| 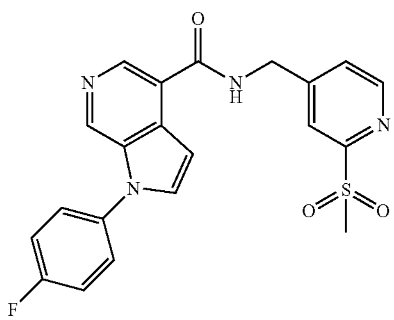 [SMILES: CS(=O)(=O)c1cc(CNC(=O)c2cncc3c2ccn3-c2ccc(F)cc2)ccn1] | 1-(4-Fluorophenyl)-1H-pyrrolo[2,3-c]pyridine-4-carboxylic acid (2-methanesulfonyl-pyridin-4-ylmethyl)-amide | 425.7 | 1.22 |
| 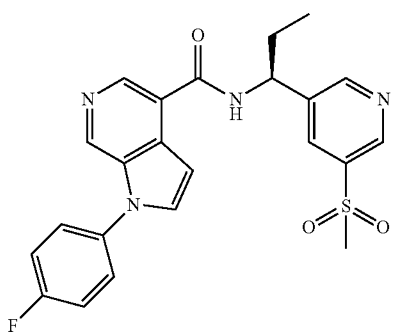 [SMILES: CC[C@H](NC(=O)c1cncc2c1ccn2-c1ccc(F)cc1)c1cncc(S(C)(=O)=O)c1] | 1-(4-Fluorophenyl)-1H-pyrrolo[2,3-c]pyridine-4-carboxylic acid [(S)-1-(5-methanesulfonyl-pyridin-3-yl)-propyl]-amide | 453.7 | 1.36 |
| 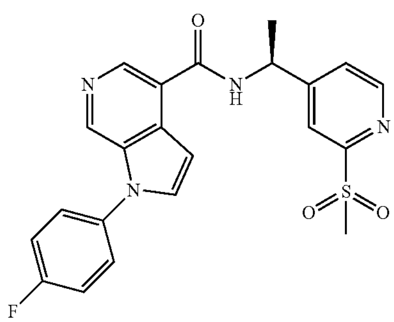 [SMILES: C[C@H](NC(=O)c1cncc2c1ccn2-c1ccc(F)cc1)c1ccnc(S(C)(=O)=O)c1] | 1-(4-Fluorophenyl)-1H-pyrrolo[2,3-c]pyridine-4-carboxylic acid [(S)-1-(2-methanesulfonyl-pyridin-4-yl)-ethyl]-amide | 439.7 | 1.16 |

TABLE I-continued

| Structure | Name | HPLC-MS Data [a] Observed Mass [b] | rt (min) |
|---|---|---|---|
| 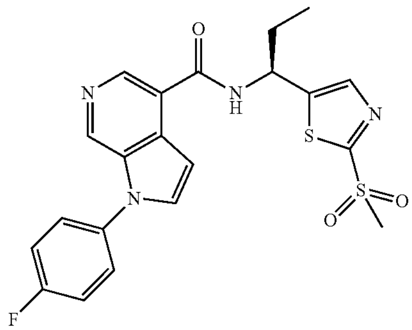 [SMILES: CC[C@H](NC(=O)c1cncc2c1ccn2-c1ccc(F)cc1)c1cnc(S(C)(=O)=O)s1] | 1-(4-Fluorophenyl)-1H-pyrrolo[2,3-c]pyridine-4-carboxylic acid [(S)-1-(2-methanesulfonyl-thiazol-5-yl)-propyl]-amide | 459.7 | 1.23 |
| 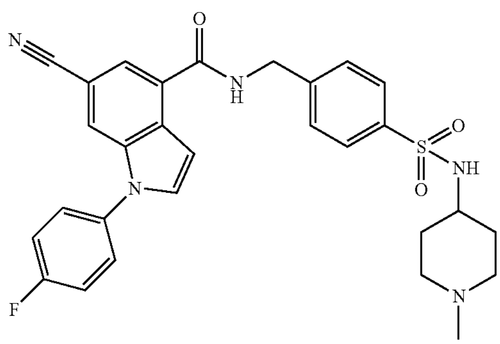 [SMILES: CN1CCC(NS(=O)(=O)c2ccc(CNC(=O)c3cc(C#N)cc4c3ccn4-c3ccc(F)cc3)cc2)CC1] | 6-Cyano-1-(4-fluorophenyl)-1H-indole-4-carboxylic acid 4-(1-methyl-piperidin-4-ylsulfamoyl)-benzylamide | 547.8 | 1.38 |
| 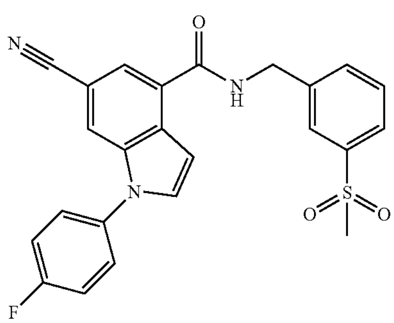 [SMILES: CS(=O)(=O)c1cccc(CNC(=O)c2cc(C#N)cc3c2ccn3-c2ccc(F)cc2)c1] | 6-Cyano-1-(4-fluorophenyl)-1H-indole-4-carboxylic acid 3-methanesulfonyl-benzylamide | 448.8 | 1.60 |
| 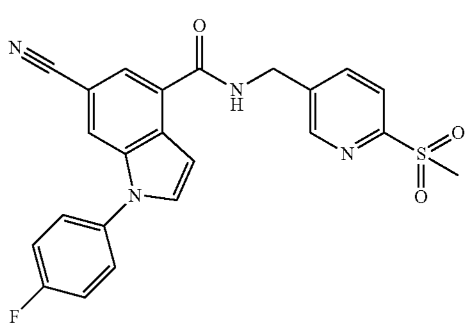 [SMILES: CS(=O)(=O)c1ccc(CNC(=O)c2cc(C#N)cc3c2ccn3-c2ccc(F)cc2)cn1] | 6-Cyano-1-(4-fluorophenyl)-1H-indole-4-carboxylic acid (6-methanesulfonyl-pyridin-3-ylmethyl)-amide | 449.7 | 1.54 |

TABLE I-continued

| Structure | Name | HPLC-MS Data [a] | |
|---|---|---|---|
| | | Observed Mass [b] | rt (min) |
| 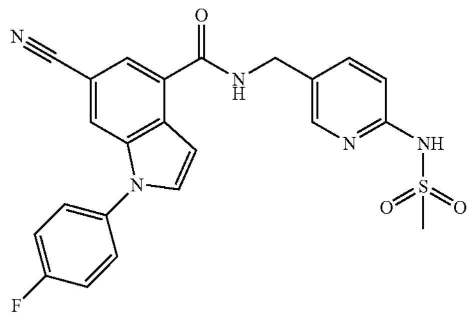 [SMILES: CS(=O)(=O)Nc1ccc(CNC(=O)c2cc(C#N)cc3c2ccn3-c2ccc(F)cc2)cn1] | 6-Cyano-1-(4-fluorophenyl)-1H-indole-4-carboxylic acid (6-methanesulfonylamino-pyridin-3-ylmethyl)-amide | 465.1 | 1.44 |
| 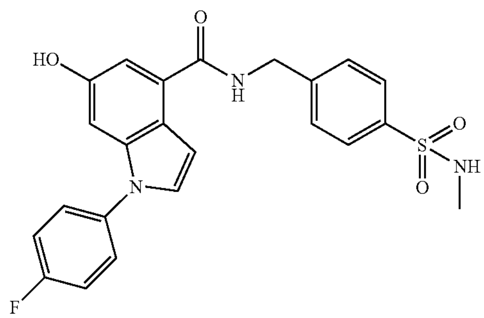 [SMILES: CNS(=O)(=O)c1ccc(CNC(=O)c2cc(O)cc3c2ccn3-c2ccc(F)cc2)cc1] | 1-(4-Fluorophenyl)-6-hydroxy-1H-indole-4-carboxylic acid 4-methylsulfamoyl-benzylamide | 454.7 | 1.47 |
| 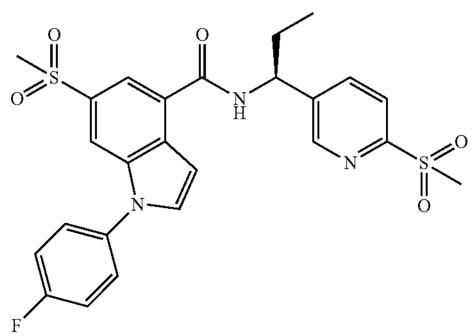 [SMILES: CC[C@H](NC(=O)c1cc(S(C)(=O)=O)cc2c1ccn2-c1ccc(F)cc1)c1ccc(S(C)(=O)=O)nc1] | 1-(4-Fluorophenyl)-6-methanesulfonyl-1H-indole-4-carboxylic acid [(S)-1-(6-methanesulfonyl-pyridin-3-yl)-propyl]-amide | 530.7 | 1.57 |
| 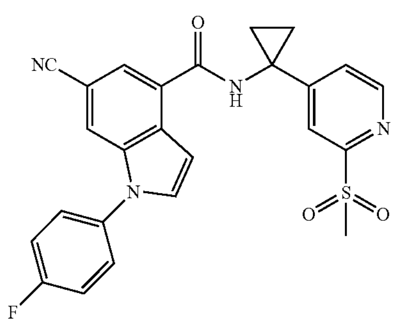 [SMILES: CS(=O)(=O)c1cc(C2(NC(=O)c3cc(C#N)cc4c3ccn4-c3ccc(F)cc3)CC2)ccn1] | 6-Cyano-1-(4-fluorophenyl)-1H-indole-4-carboxylic acid [1-(2-methanesulfonyl-pyridin-4-yl)-cyclopropyl]-amide | 475.2 | 1.70 |

[a] See Synthetic Example Section of HPLC-MS methods.
[b] [M + H]+ is reported for both 79Br and 81Br for bromine containing compounds.

or the pharmaceutically acceptable salts thereof.

For all compounds disclosed hereinabove in this application, in the event the nomenclature is in conflict with the structure, it shall be understood that the compound is defined by the structure.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes any of compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles include hydrocarbon rings containing from three to twelve carbon atoms. These carbocycles may be either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 4 or 6 membered) monocyclic or nonaromatic 8-11 membered bicyclic or spirocyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-8 membered monocyclic or 8-11 membered bicyclic ring containing 1-4 heteroatoms such as N, O and S.

Unless otherwise stated, heterocycles and heteroaryl include but are not limited to, for example furanyl, pyranyl, benzoxazolyl, benzothiazolyl, benzimidazolyl, tetrahydropyranyl, dioxanyl, dioxolanyl, tetrahydrofuranyl, oxazolyl, isoxazolyl, thiazolyl, pyrazolyl, pyrrolyl, imidazolyl, thienyl, thiadiazolyl, thiomorpholinyl, 1,1-dioxo-1$\lambda^{6}$-thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl and benzodioxolyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_{2}$—$C_{1-6}$ alkyl.

The term "alkyl" refers to a saturated aliphatic radical containing from one to ten carbon atoms or a mono- or polyunsaturated aliphatic hydrocarbon radical containing from two to twelve carbon atoms. A mono- or polyunsaturated aliphatic hydrocarbon radical must contain at least one double or triple bond, respectively. "Alkyl" refers to both branched and unbranched alkyl groups. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O).

The term "halogen" as used in the present specification shall be understood to mean bromine, chlorine, fluorine or iodine, preferably fluorine. The definitions "halogenated", "partially or fully halogenated"; partially or fully fluorinated; "substituted by one or more halogen atoms", includes for example, mono, di or tri halo derivatives on one or more carbon atoms. For alkyl, a nonlimiting example would be —$CH_{2}CHF_{2}$, —$CF_{3}$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1-C_4 \text{ alkyl})_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The invention additionally provides for methods for making compounds of formula I. The compounds of the invention may be prepared by the general methods and examples presented below, and methods known to those of ordinary skill in the art and reported in the chemical literature. Unless otherwise specified, solvents, temperatures, pressures, and other reaction conditions may be readily selected by one of ordinary skill in the art. Specific procedures are provided in the Synthetic Examples section.

Intermediate benzyl amines are commercially available, or may be synthesized via catalytic reduction of the corresponding aryl nitriles with Pd/C (Van Rompaey, K. et al. *Tetrahedron*, 2003, 59 (24), 4421) or Raney Ni (Gould, F. et al. *J. Org. Chem.*, 1960, 25, 1658) or through displacement of a benzyl bromide with sodium azide and reduction.

Intermediate aminomethylpyridines may also be commercially available or prepared by methods known to those skilled in the art. For example, methods of preparing 1-substituted-1-(pyridyl)methylamines from aldehydes or ketones are known (see, Kuduk, S. D. et al. *Tetrahedron Lett.* 2004, 45, 6641 and Chelucci, G. *Tetrahedron: Asymmetry* 2006, 17, 3163) and methods of preparing homoallylic primary amines are known (see, Kobayashi, S. et al. *J. Am. Chem. Soc.* 2006, 128, 11038). Methods of preparing 2,2,2-trifluoro-1-pyridylethylamine are known (see, Olah, G. A., et al. *Angew. Chem. Int. Ed.* 2001, 40, 589).

Intermediate carbocyclyl or heterocyclyl hydrazines may also be commercially available or prepared by methods known to those skilled in the art (see, for example, Nishino, S. et al. (2006) EP1661894 and Inoue, H. et al. (2004) EP1454897).

Aryl- or heteroaryl-cycloalkylamine intermediates are either commercially available, prepared according to the general procedures or references described below (hereby incorporated by reference in their entirety), or may be prepared by one skilled in the art using methods described in the chemical literature. Aryl- or heteroaryl-cyclopropylamine may be synthesized via titanium alkoxide-mediated reductive cyclopropanation of the corresponding aryl or heteroaryl nitriles with Grignard reagents (Szymoniak, J. et al. *J. Org. Chem.* 2002, 67, 3965, and Bertus, P. et al. *J. Org. Chem.* 2003, 68, 7133) or with zinc reagents (de Meijere, A. et al. *Org. Lett.* 5, 2003, 753). Alternatively, aryl-cyclopropylamines may be synthesized from aryl nitriles or aryl esters via cycloalkylation (e.g., Jonczyk, A. et al. *Org. Prep. Proc.* 27, 1995, 355), followed by conversion of the nitrile or ester group to a carboxylic acid, Curtius rearrangement of the resulting carboxylic acid to a carbamic ester (e.g., Hanano, T. et al. *Bioorg. Med. Chem. Lett.* 10, 2000, 881), and deprotection of the resulting carbamic ester.

Amide bond formations may be carried out by standard coupling conditions well-known in the art (see, for example, Bodanszky, M. *The Practice of Peptide Synthesis*, Springer-Verlag: 1984, which is hereby incorporated by reference in its entirety), for example, by reacting a carboxylic acid and an amine in the presence of 1-(3-dimethylaminopropyl)-3-ethylcarbodiimide (EDC) and 1-hydroxybenzotriazole. Reaction progress may be monitored by conventional methods such as thin layer chromatography (TLC). Intermediates and products may be purified by methods known in the art, including column chromatography, HPLC or recrystallization.

The methods described below and in the Synthetic Examples section may be used to prepare compounds of formula I where L is a heterocycle of formula IA-IG. In the schemes below X, $Ar_1$, $Ar_2$, $R_1$, $R_2$ and $R_3$ shall have the meanings defined in the detailed description of compounds of formula I.

Compounds of formula I where L is IA may be prepared according to Scheme I.

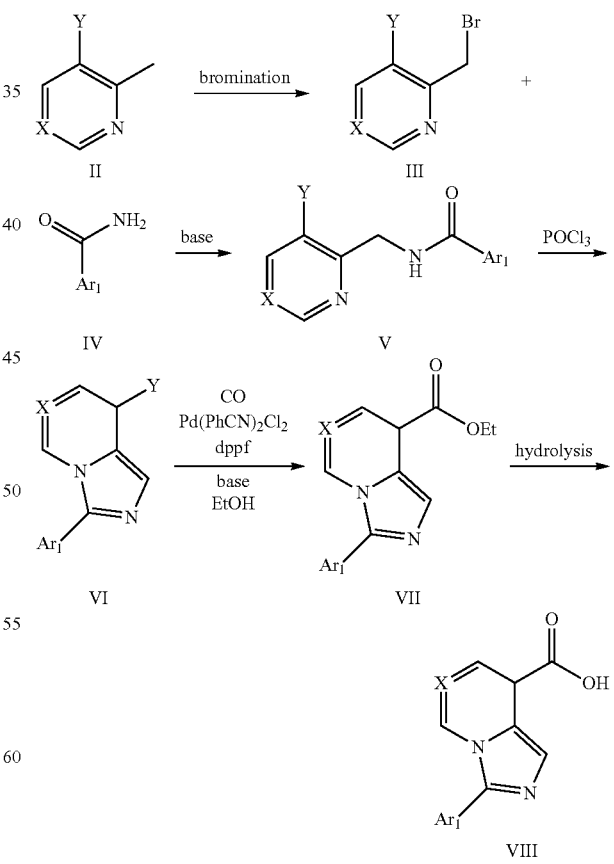

As illustrated in Scheme I, a methylpyridine (X=carbon), a substituted methylpyridine (X=C-A) or a methylpyrimidine (X=N) of formula II (where Y is a halogen chosen from chlorine or bromine) is brominated using a suitable brominating agent such as N-bromosuccinimide (NBS) in the presence of an initiator such as benzoyl peroxide in a suitable solvent such as carbon tetrachloride to provide a compound of formula III. Compounds of formula III may be reacted with an amide of formula IV bearing $Ar_1$ using a suitable base such as sodium hydride in a suitable solvent such as THF at reflux to afford a compound of formula V. The amide V will undergo a cyclization-dehydration using a suitable reagent such as phosphorous (V) oxychloride to afford heterocycle VII (IA with various $Ar_1$'s). Heterocycle VII may be heated with pressurized CO at about 10-20 bars in the presence of a Pd catalyst such as $Pd[PhCN]_2Cl_2$, a suitable ligand such as 1,1-bis(diphenylphosphino)ferrocene (dppf) and a base such as $Et_3N$ or N,N-diisopropylethyl amine (DIPEA) in absolute ethanol to provide an ethyl ester of formula VII. The ester (VII) is hydrolyzed for example by treatment with a suitable base such as KOH under aqueous conditions using a co-solvent such as methanol to provide a carboxylic acid of formula VIII.

An alternate method for preparing compounds of formula IA and IG (when X=carbon: IA equals IG) and new heterocycles of type IG (where X=N or C-A) may be prepared according to Scheme II.

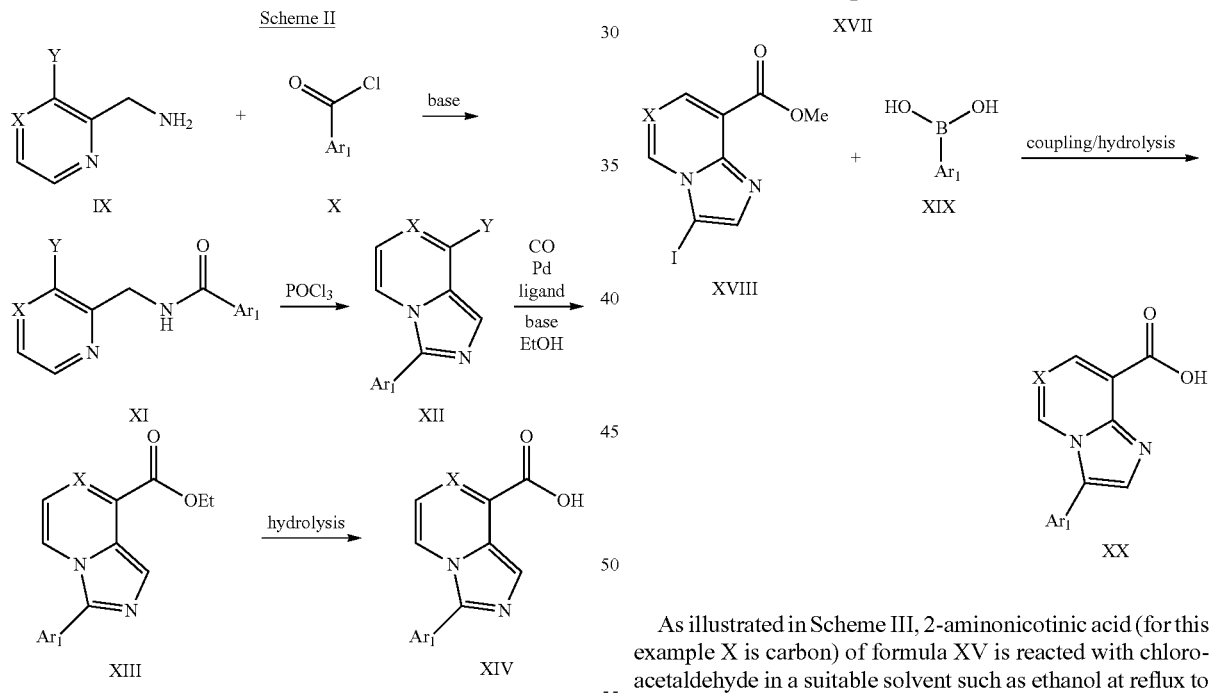

As illustrated in Scheme II, an aminomethylpyridine (X=carbon), a substituted aminomethylpyridine (X=C-A) or a aminomethylpyrazine (X=N) of formula IX (where Y is a halogen chosen from chlorine or bromine) is reacted with an acid chloride of formula X bearing $Ar_1$ in a suitable solvent such as $CH_2Cl_2$ in the presence of a suitable base such as DIPEA to afford amide XI. Cyclization and dehydration of amide XI using a suitable reagent such as phosphorous (V) oxychloride affords a heterocycle of formula XII (IA and IG are equivalent if X=carbon). Heterocycle XII is converted to a carboxylic acid of formula XIV as described in Scheme I.

Compounds of formula I where L is IB may be prepared according to Scheme III.

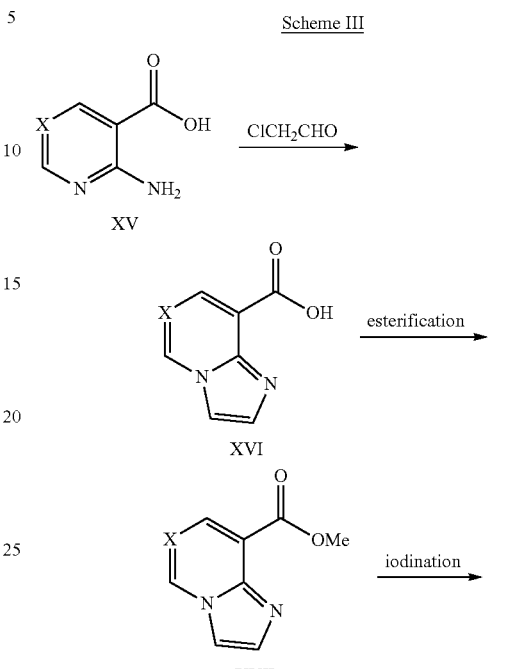

As illustrated in Scheme III, 2-aminonicotinic acid (for this example X is carbon) of formula XV is reacted with chloroacetaldehyde in a suitable solvent such as ethanol at reflux to afford a heterocycle of formula XVI. The carboxylic acid XVI is converted to the methyl ester XVII using a suitable reagent such as thionyl chloride in the presence of methanol at reflux. Iodination of heterocycle of formula XVII using N-iodosuccinimide (NIS) in a suitable solvent such as acetonitrile affords a compound of formula XVIII. The iodo compound XVIII is reacted under coupling conditions using a palladium catalyst such as tetrakis(triphenylphosphine)palladium (0) and an boronic acid of formula XIX bearing $Ar_1$ in the presence of a base such as aqueous sodium carbonate in a suitable solvent mixture such as ethanol-benzene or ethanol-toluene at reflux to afford a compound of formula XX.

Compounds of formula I where L is IC may be prepared according to Scheme IV.

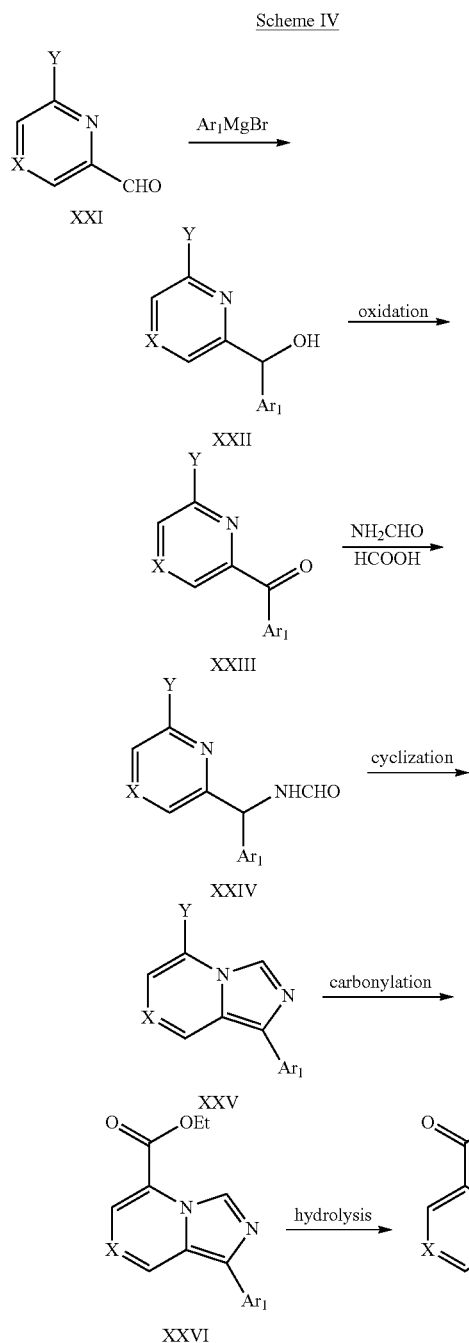

Carbonylation followed by hydrolysis as described in Scheme I affords first ester XXVI and then the carboxylic acid XXVII.

Compounds of formula I where L is IH may be prepared according to Scheme V.

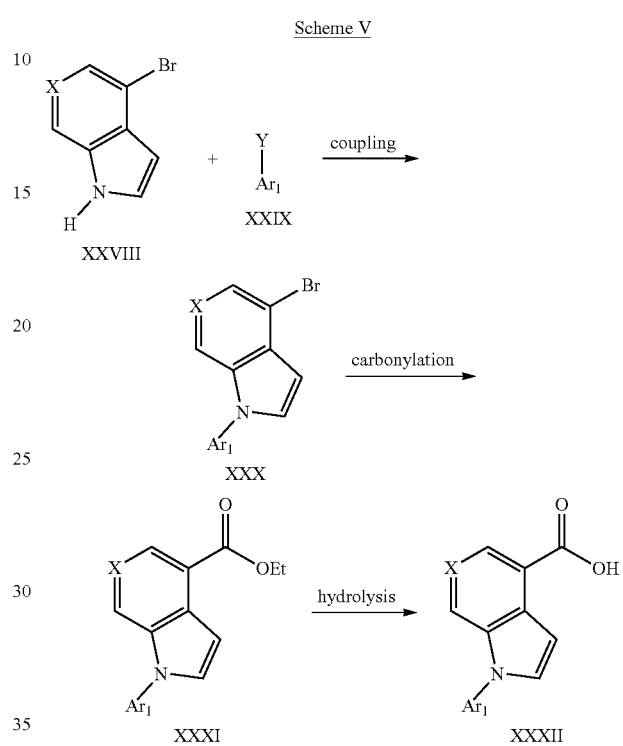

As illustrated in Scheme V, 4-bromoindole (X=carbon) or 4-bromo-6-azaindole (X=nitrogen) is reacted with $Ar_1Y$ (XXIX) where Y is a halogen (Br or I) in the presence of a suitable diamine ligand such as trans-N,N'-dimethylcyclohexane-1,2-diamine in the presence of a copper salt such as CuI and a suitable base such as $K_2CO_3$ in a suitable solvent such as N,N-dimethylformamide (DMF) to provide a compound of formula XXX. Carbonylation followed by hydrolysis as described in Scheme I affords first ester XXXI and then the carboxylic acid XXXII.

Compounds of formula I where L is ID may be prepared according to Scheme VI.

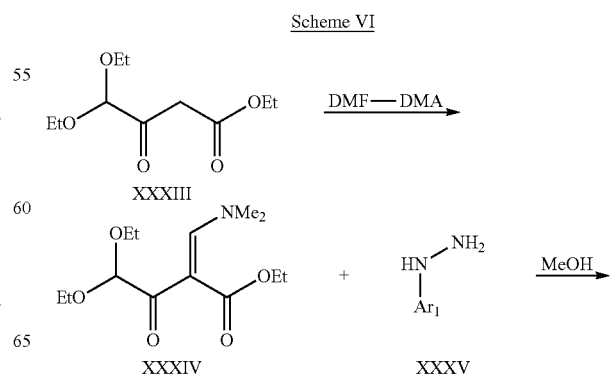

As illustrated in Scheme IV, a pyridine carboxaldehyde of formula XXI (for this example X is carbon) where Y is a halogen chosen from bromine or chlorine is reacted with a Grignard reagent bearing $Ar_1$ in a suitable solvent such as THF to afford a carbinol of formula XXII. Oxidation of XXII with a suitable oxidant such as pyridinium chlorochromate (PCC) in a suitable solvent such as dichloromethane affords ketone XXIII Treatment of ketone XXIII with a mixture of formic acid in formamide at elevated temperatures affords formamide XXIV. Cyclization-dehydration of XXIV using a suitable reagent such as $POCl_3$ affords heterocycle XXV.

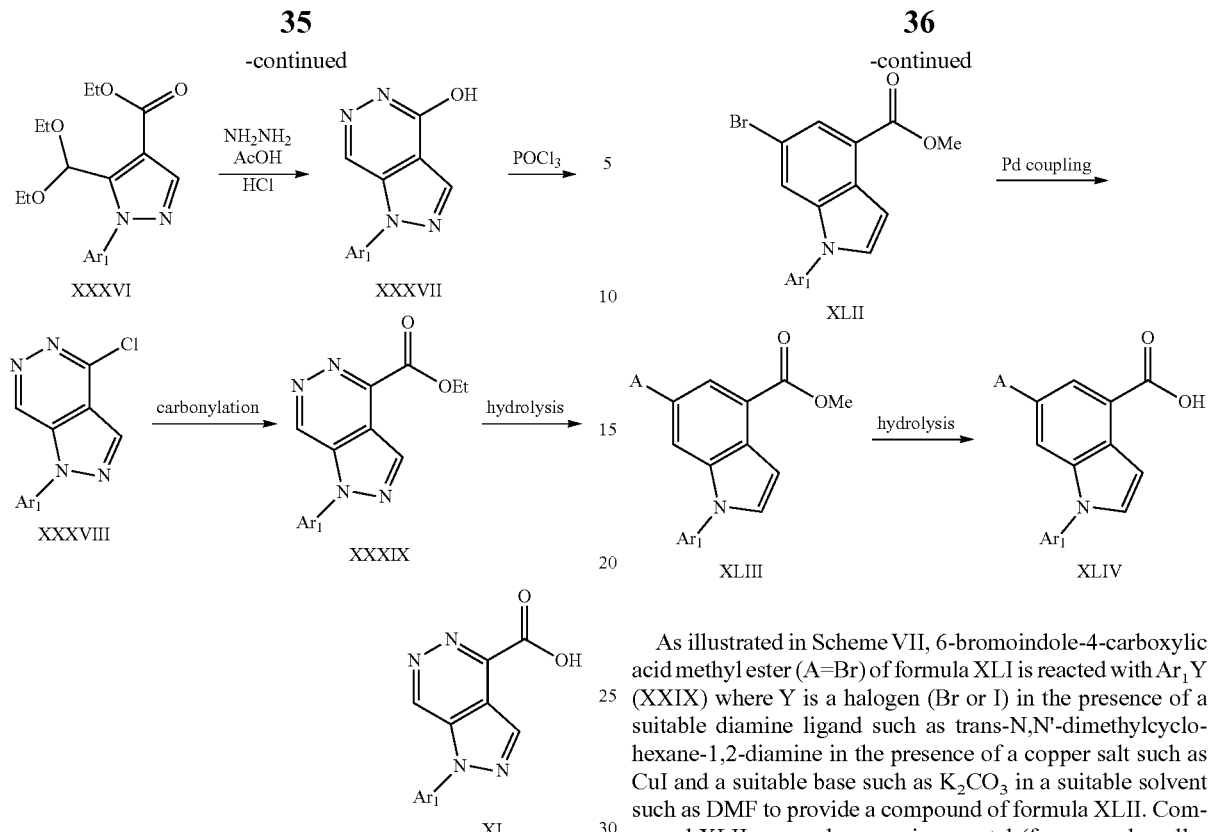

As illustrated in Scheme VI, a 1,3-dicarbonyl compound of formula XXXIII is condensed with dimethylformamide dimethyl acetal (DMF-DMA) in a suitable solvent such as xylenes at reflux to afford a compound of formula XXXIV. Compound XXXIV is reacted with a hydrazine of formula XXXV (free base or a suitable salt form such as a hydrochloride salt) bearing $Ar_1$ in a suitable solvent such as methanol at reflux to afford a pyrazole of formula XXXVI. Compound XXXVI is reacted with hydrazine monohydrate in a suitable solvent such as acetic acid in the presence of a catalytic amount of concentrated aqueous hydrochloric acid to afford a heterocycle of formula XXXVII. Compound XXXVII is converted to the 4-chloro intermediate XXXVIII using $POCl_3$ under refluxing conditions. Carbonylation followed by hydrolysis as described in Scheme I affords a carboxylic acid of formula XL.

Compounds of formula I where L is IH and X=C-A may be prepared according to Scheme VII.

Scheme VII

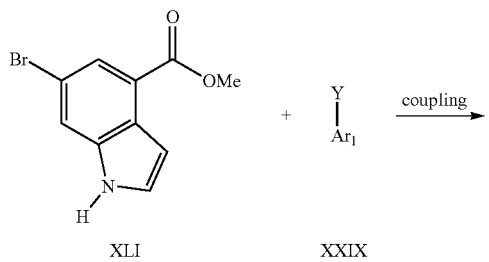

As illustrated in Scheme VII, 6-bromoindole-4-carboxylic acid methyl ester (A=Br) of formula XLI is reacted with $Ar_1Y$ (XXIX) where Y is a halogen (Br or I) in the presence of a suitable diamine ligand such as trans-N,N'-dimethylcyclohexane-1,2-diamine in the presence of a copper salt such as CuI and a suitable base such as $K_2CO_3$ in a suitable solvent such as DMF to provide a compound of formula XLII. Compound XLII can undergo various metal (for example palladium) mediated coupling reactions. For this example A=CN, reacting compound XLII with zinc cyanide with a suitable catalyst such as $Pd_2(dba)_3$ in a suitable solvent such as DMF provides a compound of formula XLIII. Compounds of formula XLII prepared by the above methods may be further converted to additional compounds of formula XLIII (where A=—OH, —$SO_2Me$) by methods known in the art. Hydrolysis of compound XLIII as described in Scheme I provides a carboxylic acid of formula XLIV.

The methods described below and in the Synthetic Examples section may be used to prepare compounds of formula I according to Scheme VIII and IX. In the schemes below L, X, $Ar_1$, $Ar_2$, $R_1$, $R_2$ and $R_3$ shall have the meanings defined in the detailed description of compounds of formula I.

Scheme VIII

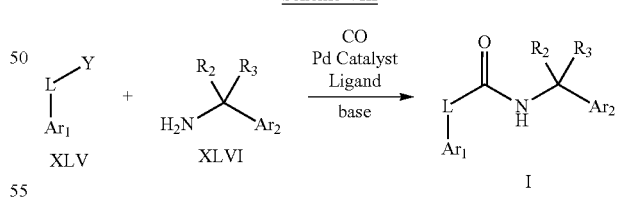

Heating XLV (where Y is a halogen chosen from chlorine or bromine, for example a compound of formula VI in Scheme I) in a sealed pressure vessel with an optionally substituted intermediate XLVI in the presence of a suitable Pd catalyst such as $Pd[PhCN]_2Cl_2$, a suitable ligand such as 1,1-bis(diphenylphosphino)ferrocene (dppf) and a base such as $Et_3N$ or DIPEA, in a solvent such as toluene in a CO atmosphere pressurized at about 15 bars provides the desired compound of formula I.

Alternatively, compounds of formula I may be synthesized according to the general procedure illustrated in Scheme IX.

Scheme IX

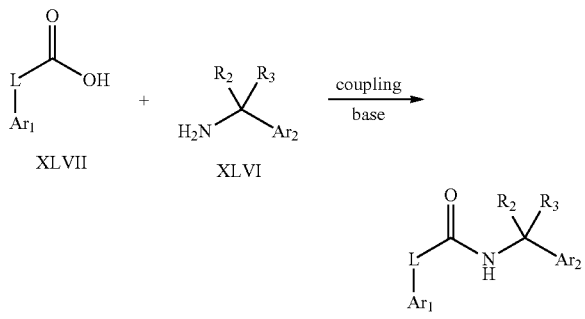

Carboxylic acid XLVII may be reacted with a suitable amine of formula XLVI under amide coupling conditions well known in the art. For example, acid XLVII may be treated with a suitable activating reagent such as thionyl chloride, oxalyl chloride, (benzotriazol-1-yloxy)tripyrrolidinophosphonium-hexafluorophosphate (PyBOP), O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU), or O-(benzotriazol-1-yl)-N,N,N',N'-tetramethyluronium tetrafluoroborate (TBTU) in the presence of a suitable amine of formula XLVI, a suitable base such as triethylamine or N,N-diisopropylethylamine (DIPEA) in a suitable solvent such as dimethylformamide or N-methylpyrrolidinone to provide the desired compound of formula I.

Compounds of formula I prepared by the above methods may be further converted to additional compounds of formula I by methods known in the art and exemplified in the Synthetic Examples section below.

SYNTHETIC EXAMPLES

General Methods:

All reactions are run at room temperature unless noted otherwise. All compounds are characterized by at least one of the following methods: $^1$H NMR, HPLC, HPLC-MS, and melting point.

The reported MS data is for observed [M+H]$^+$. For bromine and chlorine containing compounds, the [M+H]$^+$ is either reported for one or both of the bromine or chlorine isotopes (i.e., $^{79}$Br and $^{81}$Br or $^{35}$Cl and $^{37}$Cl; respectively).

Retention times (rt) are reported in Table I using one of the following methods:

| HPLC Method | Time (min) | Mobile Phase | | Flow (mL/min) | Column |
|---|---|---|---|---|---|
| | | H$_2$O (0.1% FA) | CH$_3$CN (0.1% FA) | | |
| A1 | 0 | 95 | 5 | 2.5 | Agilent Zorbax |
| | 1.7 | 5 | 95 | 2.5 | C18 SB 3.5 um |
| | 2 | 5 | 95 | 2.5 | 4.6 × 30 mm |
| | 2.1 | 95 | 5 | 2.5 | cartridge |
| | 2.3 | 95 | 5 | 2.5 | |
| B1 | 0 | 70 | 30 | 2.5 | Agilent Zorbax |
| | 1.7 | 5 | 95 | 2.5 | C18 SB 3.5 um |
| | 2 | 5 | 95 | 2.5 | 4.6 × 30 mm |
| | 2.1 | 70 | 30 | 2.5 | cartridge |
| | 2.3 | 70 | 30 | 2.5 | |
| C1 | 0 | 99 | 1 | 2.5 | Agilent Zorbax |
| | 1.7 | 50 | 50 | 2.5 | C18 SB 3.5 um |
| | 2 | 5 | 95 | 2.5 | 4.6 × 30 mm |
| | 2.1 | 5 | 95 | 2.5 | cartridge |
| | 2.3 | 99 | 1 | 2.5 | |
| D1 | 0 | 95 | 5 | 1.5 | Agilent Zorbax |
| | 7 | 5 | 95 | 1.5 | Eclipse XDB-C8 |
| | 9 | 5 | 95 | 1.5 | 5 um 4.6 × 150 mm |
| | 9.3 | 95 | 5 | 1.5 | |
| | 10 | 95 | 5 | 1.5 | |
| C2 | 0 | 99 | 1 | 2.5 | Agilent Zorbax |
| | 1.6 | 80 | 20 | 2.5 | C18 SB 3.5 um |
| | 1.7 | 5 | 95 | 2.5 | 4.6 × 30 mm |
| | 2 | 5 | 95 | 2.5 | cartridge |
| | 2.1 | 99 | 1 | 2.5 | |
| | 2.3 | 99 | 1 | 2.5 | |
| D2 | 0 | 99 | 1 | 1.5 | Agilent Zorbax |
| | 2 | 80 | 20 | 1.5 | Eclipse XDB-C8 |
| | 7 | 5 | 95 | 1.5 | 5 um 4.6 × 150 |
| | 9 | 5 | 95 | 1.5 | mm column |
| | 9.3 | 99 | 1 | 1.5 | |
| | 10 | 99 | 1 | 1.5 | |
| A3 | 0 | 88 | 12 | 1.5 | Agilent SB-C18 |
| | 0.25 | 70 | 30 | 1.5 | 1.8 um 3 × 50 |
| | 0.3 | 60 | 40 | 1.5 | mm column |
| | 1.19 | 5 | 95 | 1.5 | |
| | 1.75 | 0 | 100 | 1.5 | |
| B3 | 0 | 60 | 40 | 1.5 | Agilent Eclipse |
| | 1.19 | 15 | 85 | 1.5 | C8 1.8 um |
| | 1.75 | 0 | 100 | 1.5 | 3 × 50 mm column |
| C3 | 0 | 95 | 5 | 1.5 | Agilent SB-AQ |
| | 0.25 | 50 | 50 | 1.5 | 1.8 um 3 × 50 |
| | 0.3 | 70 | 30 | 1.5 | mm column |
| | 1.3 | 10 | 90 | 1.5 | |
| | 1.7 | 0 | 100 | 1.5 | |
| D3 | 0 | 95 | 5 | 1.5 | Agilent SB-C18 |
| | 3.8 | 10 | 90 | 1.5 | 1.8 um 3 × 50 |
| | 4.5 | 0 | 100 | 1.5 | mm column |

| HPLC Method | Time (min) | Mobile Phase | | Flow (mL/min) | Column |
|---|---|---|---|---|---|
| | | 95% H$_2$O + 5% CH$_3$CN (0.05% Formic Acid) | CH$_3$CN (0.05% Formic Acid) | | |
| E | 0 | 90 | 10 | 0.8 | BEH 2.1 × 50 mm |
| | 1.19 | 5 | 95 | 0.8 | C18, 1.7 um |
| | 1.7 | 5 | 95 | 0.8 | particle diameter |

Example 1

Synthesis of 3-(4-Fluorophenyl)-imidazo[1,5-a]pyridine-8-carboxylic acid (1)

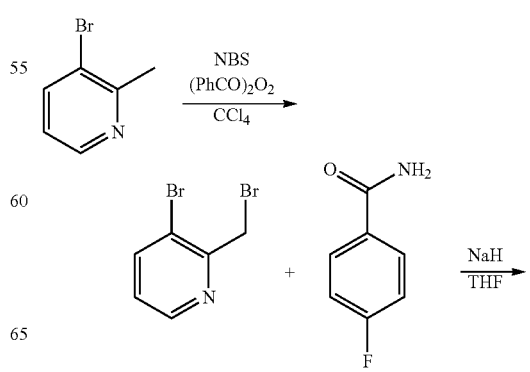

-continued

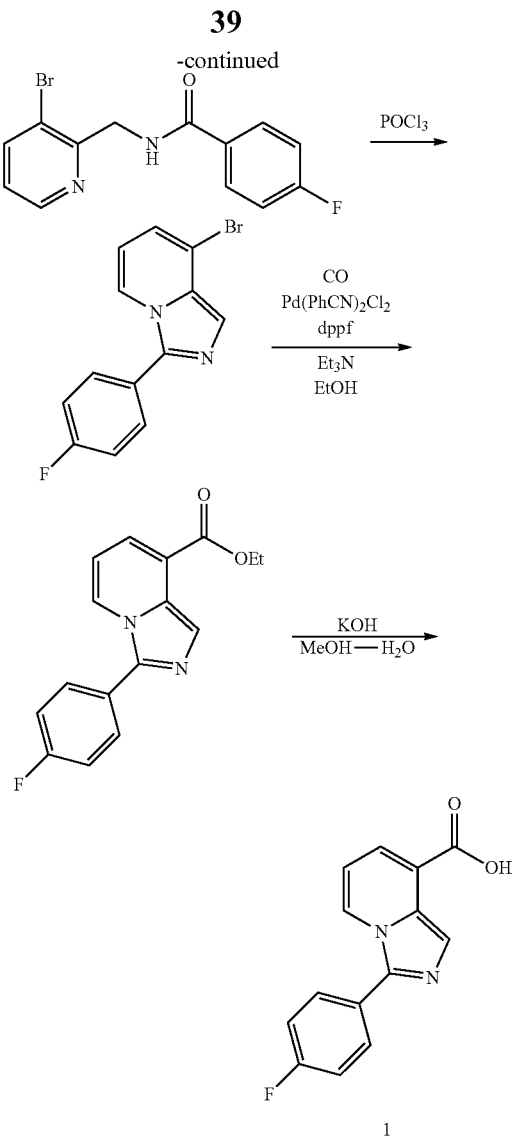

To a room temperature solution of 3-bromo-2-methylpyridine (2.60 g, 15.1 mmol) and N-bromosuccinimide (NBS) (2.90 g, 16.3 mmol) in $CCl_4$ is added benzoyl peroxide (150 mg, 1.08 mmol). The mixture is heated at reflux for 7 hours, cooled to room temperature, diluted with saturated aqueous sodium bicarbonate (30 mL) and extracted with ethyl acetate (EtOAc) (3×30 mL). The combined organic layers are washed with brine (3×30 mL), dried over magnesium sulfate, filtered and concentrated. LCMS analysis indicated starting material and the desired product. The residue is dissolved in $CCl_4$ (40 mL) and NBS (1.7 g, 9.6 mmol) and benzoyl peroxide (100 mg, 0.72 mmol) is added, and the mixture is warmed at reflux. After 24 hours, the mixture is cooled to room temperature, diluted with saturated aqueous sodium bicarbonate (30 mL) and extracted with EtOAc (3×30 mL). The combined organic layers are washed with brine (3×30 mL), dried over magnesium sulfate, filtered and concentrated. The residue is purified by silica gel chromatography eluting with a mixture of dichloromethane in hexanes (25:75, then 3:7) to afford 3-bromo-2-bromomethyl-pyridine.

To a mixture of 3-bromo-2-bromomethyl-pyridine (1.30 g, 5.18 mmol) and 4-fluoro-benzamide (725 mg, 5.21 mmol) in THF (20 mL) is added 60% sodium hydride in mineral oil (210 mg, 5.3 mmol) and the mixture is warmed at reflux. After 24 hours, the mixture is diluted with saturated aqueous ammonium chloride (25 mL) and extracted with ethyl acetate (2×25 mL). The combined organic layers are washed with brine (2×25 mL), dried over magnesium sulfate, filtered and concentrated. The residue is purified by silica gel chromatography eluting using a gradient of 5-25% EtOAc in hexanes to afford N-(3-bromopyridin-2-ylmethyl)-4-fluoro-benzamide.

The following compound is prepared by the method described above by reacting 3-bromo-2-bromomethyl-pyridine with 3,4-dichloro-benzamide:
N-(3-Bromo-pyridin-2-ylmethyl)-3,4-dichloro-benzamide.

A mixture of N-(3-bromopyridin-2-ylmethyl)-4-fluoro-benzamide (594 mg, 1.92 mmol) in $POCl_3$ (5.0 mL) is warmed at reflux. After 1.5 hours, the mixture is cooled to room temperature and poured into water while adding crushed ice to control the exotherm. The mixture is made basic with potassium carbonate and the precipitate is collected by filtration to afford 8-bromo-3-(4-fluorophenyl)-imidazo[1,5-a]pyridine.

According to the method above N-(3-Bromo-pyridin-2-ylmethyl)-3,4-dichloro-benzamide is converted to 8-bromo-3-(3,4-dichloro-phenyl)-imidazo[1,5-a]pyridine.

A mixture of 8-bromo-3-(4-fluorophenyl)-imidazo[1,5-a]pyridine (355 mg, 1.22 mmol), $Et_3N$ (330 µL, 2.5 mmol), $Pd[PhCN]_2Cl_2$ (11 mg, 0.029 mmol), and 1,1-bis(diphenylphosphino)ferrocene (dppf) (42 mg, 0.076 mmol) in absolute ethanol (15 mL) is placed in a pressure reactor with stirring and placed under 15 bars of carbon monoxide and warmed at 140° C. After 4 hours, the pressure reactor is cooled to room temperature, returned to atmospheric pressure and opened. The reaction mixture is concentrated in vacuo, the resulting residue is dissolved in dichloromethane and passed through a pad of silica gel eluting with ethyl ether to afford 3-(4-fluorophenyl)-imidazo[1,5-a]pyridine-8-carboxylic acid ethyl ester.

To a solution of 3-(4-fluorophenyl)-imidazo[1,5-a]pyridine-8-carboxylic acid ethyl ester (290 mg, 1.0 mmol) in methanol (20 mL) is added a solution of 85% potassium hydroxide pellets (0.300 g, 3.92 mmol) in water (5.0 mL). The reaction mixture is warmed at reflux for 5 minutes, cooled to room temperature and concentrated in vacuo to remove excess methanol. The mixture is acidified to pH 4 with 1 N aqueous HCl and the resulting precipitate is collected by filtration, washed with water and dried to afford the title product.

Example 2

Synthesis of 1-(4-Fluorophenyl)-1H-pyrazolo[3,4-d]pyridazine-4-carboxylic acid (2)

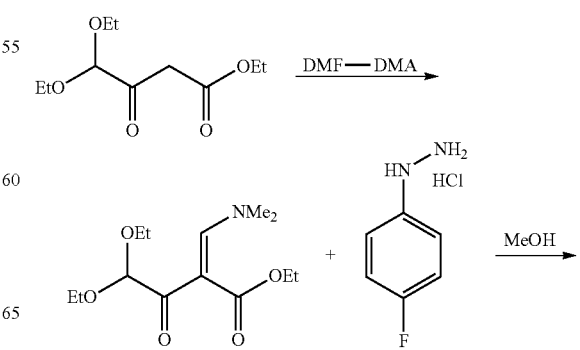

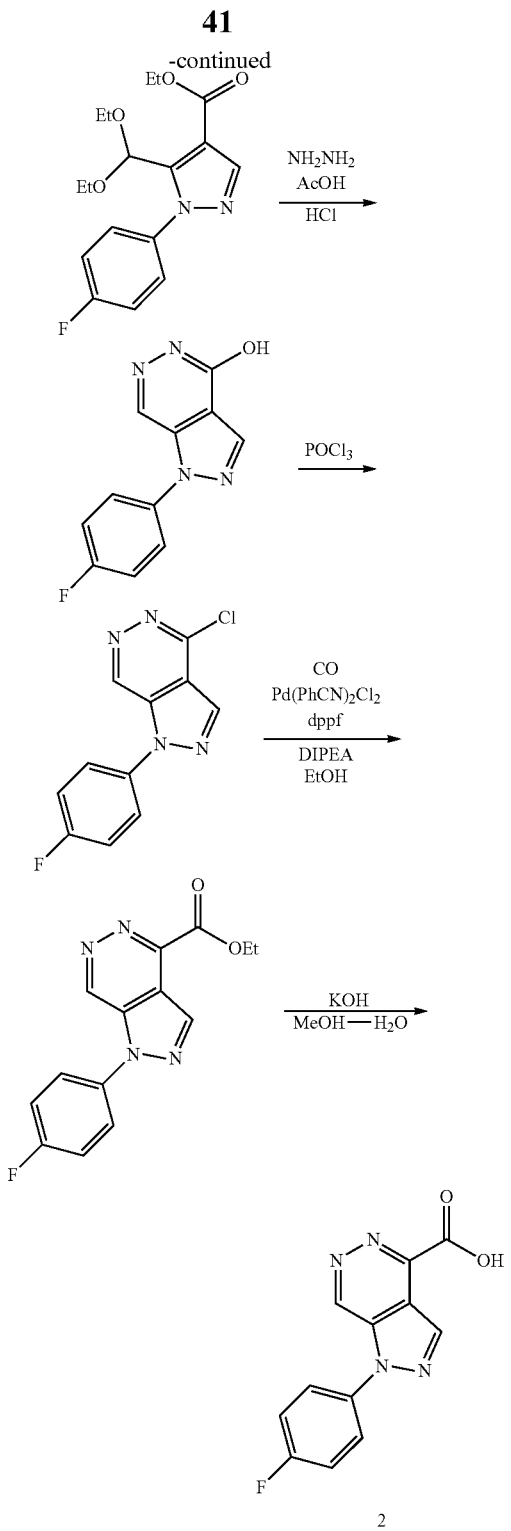

A mixture of the 4,4-diethoxy-3-oxo-butyric acid ethyl ester (0.500 g, 2.29 mmol, prepared according to the procedure described in JACS, 1919, 41, 812) and dimethylformamide dimethyl acetal (370 μL, 2.78 mmol) in xylenes (5.0 mL) is warmed at reflux. After 30 minutes, The reaction mixture is concentrated in vacuo to afford 2-[1-dimethylamino-meth-(Z)-ylidene]-4,4-diethoxy-3-oxo-butyric acid ethyl ester, which is used in the next step without purification.

To a solution of 2-[1-dimethylamino-meth-(Z)-ylidene]-4,4-diethoxy-3-oxo-butyric acid ethyl ester (625 mg, 2.28 mmol) in methanol (10 mL) is added 4-fluorophenylhydrazine hydrochloride (410 mg, 2.5 mmol). The mixture is warmed at reflux. After 2 hours, the reaction mixture is cooled to room temperature, concentrated in vacuo, diluted with water (15 mL) and extracted with ether (3×15 mL). The combined ether layers are washed with brine (2×15 mL), dried over magnesium sulfate, filtered and concentrated. The residue is purified by silica gel chromatography eluting with a gradient of 0-10% EtOAc in hexanes to afford 5-diethoxymethyl-1-(4-fluorophenyl)-1H-pyrazole-4-carboxylic acid ethyl ester.

To a solution of 5-diethoxymethyl-1-(4-fluorophenyl)-1H-pyrazole-4-carboxylic acid ethyl ester (5.70 g, 16.9 mmol) in acetic acid (100 mL) is added hydrazine monohydrate (5.0 mL, 6.1 mmol) and 12 N aqueous hydrochloric acid (200 μL). The reaction mixture is warmed at reflux. After 2 hours, the mixture is cooled to room temperature and diluted with water. The solid is collected by filtration, washed with water and air dried to afford 1-(4-fluorophenyl)-1H-pyrazolo[3,4-d]pyridazin-4-ol.

A mixture of 1-(4-fluorophenyl)-1H-pyrazolo[3,4-d]pyridazin-4-ol (1.30 g, 5.65 mmol), and POCl₃ (25 mL) is warmed at 100° C. After 4 hours, the reaction mixture is cooled to room temperature and added dropwise to ice cold water, followed by periodic addition of crushed ice to control the exotherm. To the aqueous solution is added EtOAc and the mixture is neutralized with sodium bicarbonate. The organic layer is separated and the aqueous layer is extracted with EtOAc (3×50 mL). The combined organic layers are washed with saturated aqueous sodium bicarbonate (2×30 mL) and brine (2×30 mL), dried over magnesium sulfate, filtered and concentrated to afford 4-chloro-1-(4-fluorophenyl)-1H-pyrazolo[3,4-d]pyridazine, which is used without purification.

A mixture of 4-chloro-1-(4-fluorophenyl)-1H-pyrazolo[3,4-d]pyridazine (510 mg, 2.1 mmol), DIPEA (700 μL, 4 mmol)), Pd[PhCN]₂Cl₂ (24 mg, 0.063 mmol), and 1,1-bis(diphenylphosphino)ferrocene (dppf) (48 mg, 0.087 mmol) in absolute ethanol (15 mL) is placed in a sealed pressure reactor with stirring and placed under 15 bars of carbon monoxide and warmed at 85° C. After 18 hours, the sealed pressure reactor is cooled to room temperature, returned to atmospheric pressure and opened. The reaction mixture is diluted with saturated aqueous ammonium chloride (30 mL) and extracted with EtOAc (3×20 mL). The combined organic layers are washed with saturated aqueous ammonium chloride (2×15 mL) and brine (2×15 mL), dried over magnesium sulfate, filtered and concentrated. The crude product is passed through a pad of silica gel eluting using a gradient of 10-40% EtOAc in hexanes to afford 1-(4-fluorophenyl)-1H-pyrazolo[3,4-d]pyridazine-4-carboxylic acid ethyl ester as a solid.

The title product is prepared from 1-(4-fluorophenyl)-1H-pyrazolo[3,4-d]pyridazine-4-carboxylic acid ethyl ester (520 mg, 1.82 mmol) according to the procedure described in Example 1, with the exception that the reaction progress is monitored for the disappearance of the starting material by TLC (EtOAc:hexanes; 1:1) prior to work up.

Example 3

Synthesis of 3-(4-Fluorophenyl)-imidazo[1,5-a]pyrazine-8-carboxylic acid (3)

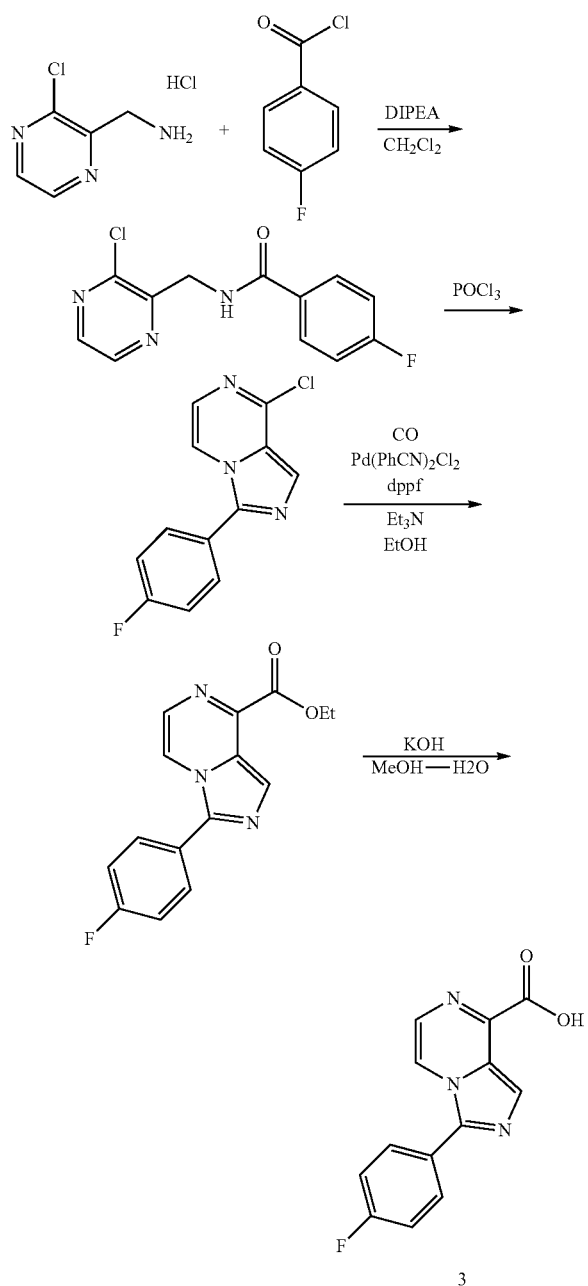

To a suspension of 2-aminomethyl-3-chloropyrazine hydrochloride (900 mg, 5 mmol) in dichloromethane (25 mL) is added 4-fluorobenzoyl chloride (730 µL, 6.1 mmol) followed by DIPEA (2.0 mL, 11 mmol). After 1 day, the mixture is concentrated and diluted with saturated aqueous ammonium chloride and extracted with EtOAc (3×40 mL). The combined organic layers are washed with brine (3×25 mL), dried over magnesium sulfate, filtered and concentrated. The residue is passed through a pad of silica gel using dichloromethane-heptane (1:1) to load the sample and then eluting with dichloromethane to afford N-(3-chloro-pyrazin-2-ylmethyl)-4-fluoro-benzamide as an oil which partially solidified.

A mixture of N-(3-chloro-pyrazin-2-ylmethyl)-4-fluoro-benzamide (986 mg, 3.71 mmol) and POCl$_3$ is warmed at reflux. After 2 hours, the mixture is cautiously added to ice water, made basic with sodium bicarbonate and extracted with EtOAc (3×75 mL). The combined organic layers are washed with saturated aqueous sodium bicarbonate (2×30 mL), brine (2×15 mL), dried over magnesium sulfate, filtered and concentrated to afford as determined by LCMS a mixture of 8-chloro-3-(4-fluorophenyl)-imidazo[1,5-a]pyrazine and 3-(4-fluorophenyl)-7H-imidazo[1,5-a]pyrazin-8-one. The crude mixture is diluted with first ether and then hexanes. The solid is filitered to afford 3-(4-fluorophenyl)-7H-imidazo[1,5-a]pyrazin-8-one. The filtrate is passed through a pad of silica gel eluting with ether to afford 8-chloro-3-(4-fluorophenyl)-imidazo[1,5-a]pyrazine.

A mixture of 8-chloro-3-(4-fluorophenyl)-imidazo[1,5-a]pyrazine (612 mg, 2.47 mmol), DIPEA (500 µL, 2.9 mmol), Pd[PhCN]$_2$Cl$_2$ (25 mg, 0.07 mmol), and dppf (50 mg, 0.09 mmol) in absolute ethanol (10 mL) in a pressure reactor with stirring and placed under 15 bars of carbon monoxide is warmed at 80° C. After 24 hours, the mixture is cooled to room temperature, returned to atmospheric pressure and opened. The mixture is diluted with brine (100 mL) and extracted with EtOAc (3×40 mL). The combined organic layers are washed with brine (3×25 mL), dried over magnesium sulfate, filtered and concentrated. The residue is passed through a pad of silica gel using dichloromethane-heptane (1:1) to load the sample and then eluting with dichloromethane-heptane (1:1, then 75:25, then 100:0) and then EtOAc-dichloromethane (2:8, then 1:1) to afford 3-(4-fluorophenyl)-imidazo[1,5-a]pyrazine-8-carboxylic acid ethyl ester.

To a solution of 3-(4-fluorophenyl)-imidazo[1,5-a]pyrazine-8-carboxylic acid ethyl ester (440.0 mg, 1.54 mmol) in methanol (10 mL) is added in several portions a solution of 85% KOH (330 mg, 4.9 mmol) in water (3 mL) (additional water is added to suspend the solid that precipitated) and the mixture is warmed at reflux. The methanol is removed in vacuo and the residue is diluted with water (15 mL) and made acidic (pH=4) with 1 N aqueous HCl. The solid is collected by filtration washing with water and then ether to afford 3-(4-fluorophenyl)-imidazo[1,5-a]pyrazine-8-carboxylic acid.

Example 4

Synthesis of 1-(4-Fluorophenyl)-1H-pyrrolo[2,3-c]pyridine-4-carboxylic acid (4)

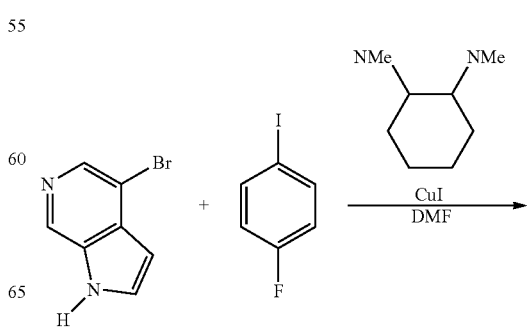

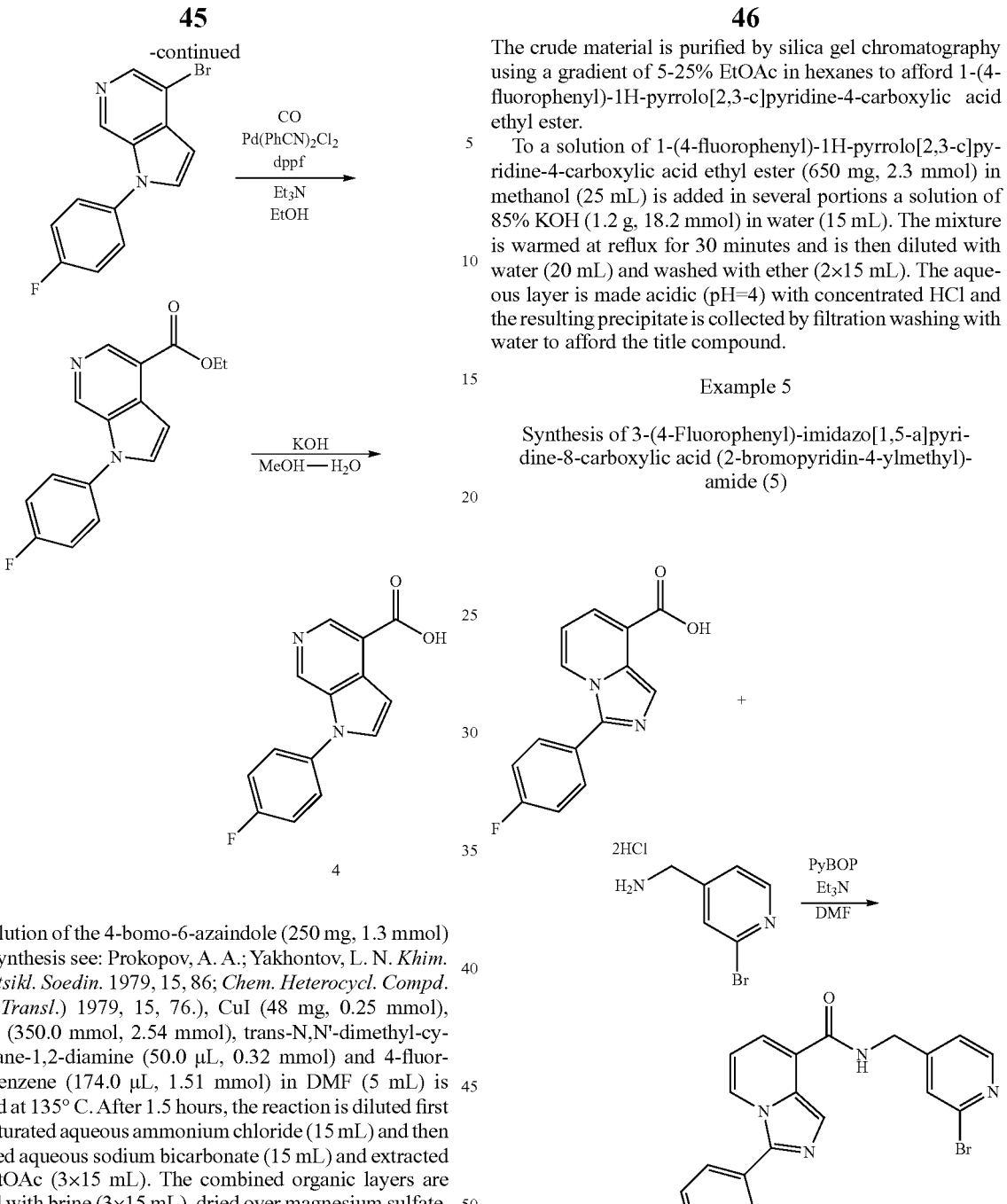

The crude material is purified by silica gel chromatography using a gradient of 5-25% EtOAc in hexanes to afford 1-(4-fluorophenyl)-1H-pyrrolo[2,3-c]pyridine-4-carboxylic acid ethyl ester.

To a solution of 1-(4-fluorophenyl)-1H-pyrrolo[2,3-c]pyridine-4-carboxylic acid ethyl ester (650 mg, 2.3 mmol) in methanol (25 mL) is added in several portions a solution of 85% KOH (1.2 g, 18.2 mmol) in water (15 mL). The mixture is warmed at reflux for 30 minutes and is then diluted with water (20 mL) and washed with ether (2×15 mL). The aqueous layer is made acidic (pH=4) with concentrated HCl and the resulting precipitate is collected by filtration washing with water to afford the title compound.

Example 5

Synthesis of 3-(4-Fluorophenyl)-imidazo[1,5-a]pyridine-8-carboxylic acid (2-bromopyridin-4-ylmethyl)-amide (5)

A solution of the 4-bomo-6-azaindole (250 mg, 1.3 mmol) (for a synthesis see: Prokopov, A. A.; Yakhontov, L. N. *Khim. Geterotsikl. Soedin.* 1979, 15, 86; *Chem. Heterocycl. Compd. (Engl. Transl.)* 1979, 15, 76.), CuI (48 mg, 0.25 mmol), K₂CO₃ (350.0 mmol, 2.54 mmol), trans-N,N'-dimethyl-cyclohexane-1,2-diamine (50.0 µL, 0.32 mmol) and 4-fluoroiodobenzene (174.0 µL, 1.51 mmol) in DMF (5 mL) is warmed at 135° C. After 1.5 hours, the reaction is diluted first with saturated aqueous ammonium chloride (15 mL) and then saturated aqueous sodium bicarbonate (15 mL) and extracted with EtOAc (3×15 mL). The combined organic layers are washed with brine (3×15 mL), dried over magnesium sulfate, filtered and concentrated. The residue is purified by silica gel chromatography using dichloromethane-hexanes (1:1) to load the sample and then eluting with EtOAc-hexanes (5:95) to afford partially purified 4-bromo-1-(4-fluorophenyl)-1H-pyrrolo[2,3-c]pyridine which is used without further purification.

A mixture of 4-bromo-1-(4-fluorophenyl)-1H-pyrrolo[2,3-c]pyridine (820.0 mg, 2.82 mmol), Et₃N (1.00 mL, 7.19 mmol), Pd[PhCN]₂Cl₂ (45 mg, 0.12 mmol), and dppf (155 mg, 0.28 mmol) in absolute ethanol (20 mL) is placed in a pressure reactor with stirring and placed under 15 bars of carbon monoxide and warmed at 140° C. After 2 hours, the pressure reactor is cooled to room temperature, returned to atmopheric pressure and opened. The reaction is diluted with ammonium chloride and extracted with EtOAc (3×25 mL). The combined organic layers are washed with brine (2×10 mL), dried over magnesium sulfate, filtered and concentrated.

To a mixture of 3-(4-fluorophenyl)-imidazo[1,5-a]pyridine-8-carboxylic acid (125 mg, 0.488 mmol) and Et₃N (0.400 mL, 2.88 mmol) in DMF (3 mL) is added benzotriazol-1-yloxy)tripyrrolidinophosphoniumhexafluorophosphate (PyBOP) (0.300 g, 0.577 mmol). After 10 minutes, C-(2-bromopyridin-4-yl)-methylamine di-hydrochloride salt (153 mg, 0.589 mmol) is added and the mixture is stirred at room temperature. After 2 hours, the reaction is diluted with saturated aqueous ammonium chloride (10 mL) and extracted with EtOAc (3×7 mL). The combined organic layers are washed with saturated aqueous ammonium chloride (2×10 mL), brine (2×10 mL), dried over magnesium sulfate, filtered and concentrated. The residue is purified by silica gel chromatography eluting with a gradient of 0-2% methanol in dichloromethane. The resulting solid is triturated with ethyl ether to afford the title compound.

The following compounds are also prepared according to the method described in Example 5:
3-(4-Fluorophenyl)-imidazo[1,5-a]pyridine-8-carboxylic acid 3-methanesulfonyl-benzylamide;
3-(4-Fluorophenyl)-imidazo[1,5-a]pyridine-8-carboxylic acid (6-bromopyridin-3-ylmethyl)-amide;
3-(4-Fluorophenyl)-imidazo[1,5-a]pyridine-8-carboxylic acid [1-(6-methanesulfonyl-pyridin-3-yl)-butyl]-amide; and
3-(4-Fluorophenyl)-imidazo[1,5-a]pyridine-8-carboxylic acid [(S)-1-(6-bromopyridin-3-yl)-propyl]-amide.

The following compounds are prepared from 3-(4-fluorophenyl)-imidazo[1,2-a]pyridine-8-carboxylic acid according to the method described in Example 5:
3-(4-Fluorophenyl)-imidazo[1,2-a]pyridine-8-carboxylic acid [(S)-1-(6-bromopyridin-3-yl)-butyl]-amide; and
3-(4-Fluorophenyl)-imidazo[1,2-a]pyridine-8-carboxylic acid [(S)-1-(6-bromopyridin-3-yl)-propyl]-amide.

The following compound is prepared from 1-(4-fluorophenyl)-imidazo[1,5-a]pyridine-5-carboxylic acid according to the method described in Example 5:
1-(4-Fluorophenyl)-imidazo[1,5-a]pyridine-5-carboxylic acid [(S)-1-(6-bromopyridin-3-yl)-propyl]-amide.

The following compound is prepared from 6-cyano-1-(4-fluorophenyl)-1H-indole-4-carboxylic acid according to the method described in Example 5;
6-Cyano-1-(4-fluorophenyl)-1H-indole-4-carboxylic acid 4-(1-methyl-piperidin-4-ylsulfamoyl)-benzylamide; and
6-Cyano-1-(4-fluorophenyl)-1H-indole-4-carboxylic acid 3-methanesulfonyl-benzylamide.

The following compounds are prepared from 1-(4-fluorophenyl)-1H-pyrrolo[2,3-c]pyridine-4-carboxylic acid by methods described in Example 5 with the following modification. The coupling reagent benzotriazol-1-yloxy)tripyrrolidinophosphoniumhexafluorophosphate (PyBOP) is replaced with O-(benzotriazol-1-yl-N,N,N',N'-tetramethyluronium hexafluorophosphate (HBTU):
1-(4-Fluorophenyl)-1H-pyrrolo[2,3-c]pyridine-4-carboxylic acid [(S)-1-(6-methanesulfonyl-pyridin-3-yl)-propyl]-amide;
1-(4-Fluorophenyl)-1H-pyrrolo[2,3-c]pyridine-4-carboxylic acid 3-methanesulfonyl-benzylamide; and
1-(4-Fluorophenyl)-1H-pyrrolo[2,3-c]pyridine-4-carboxylic acid [(S)-1-(2-methanesulfonyl-pyridin-4-yl)-propyl]-amide.

The following compounds are prepared from 1-(4-fluorophenyl)-1H-pyrrolo[2,3-c]pyridine-4-carboxylic acid by methods described in Example 5 with the following modification. The coupling reagent benzotriazol-1-yloxy)tripyrrolidinophosphoniumhexafluorophosphate (PyBOP) is replaced with O-(benzotriazol-1-yl)-N,N,N',N'-tetramethyluronium tetrafluoroborate (TBTU):
1-(4-Fluorophenyl)-1H-pyrrolo[2,3-c]pyridine-4-carboxylic acid (2-methanesulfonyl-pyridin-4-ylmethyl)-amide;
1-(4-Fluorophenyl)-1H-pyrrolo[2,3-c]pyridine-4-carboxylic acid [(S)-1-(5-methanesulfonyl-pyridin-3-yl)-propyl]-amide;
1-(4-Fluorophenyl)-1H-pyrrolo[2,3-c]pyridine-4-carboxylic acid [(S)-1-(2-methanesulfonyl-pyridin-4-yl)-ethyl]-amide; and
1-(4-Fluorophenyl)-1H-pyrrolo[2,3-c]pyridine-4-carboxylic acid [(S)-1-(2-methanesulfonyl-thiazol-5-yl)-propyl]-amide.

The following compound is prepared from 6-Cyano-1-(4-fluorophenyl)-1H-indole-4-carboxylic acid according to the method described in Example 5:
6-Cyano-1-(4-fluorophenyl)-1H-indole-4-carboxylic acid [1-(2-methanesulfonyl-pyridin-4-yl)-cyclopropyl]-amide.

Example 6

Synthesis of 1-(4-Fluorophenyl)-1H-pyrazolo[3,4-d]pyridazine-4-carboxylic acid (2-methanesulfonyl-pyridin-4-ylmethyl)-amide (6)

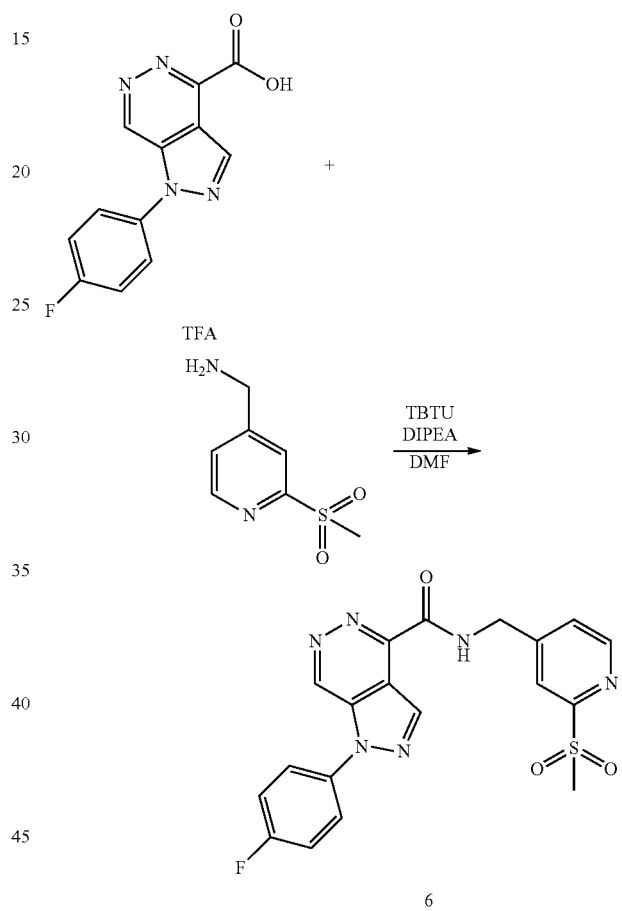

To a solution of 1-(4-fluorophenyl)-1H-pyrazolo[3,4-d]pyridazine-4-carboxylic acid (55.0 mg, 0.213 mmol), C-(2-methanesulfonyl-pyridin-4-yl)-methylamine trifluoroacetic acid salt (80.0 mg, 0.266 mmol) and DIPEA (112 μL, 0.644 mmol) in DMF (3.0 mL) is added TBTU (93.0 mg, 0.290 mmol). After 30 minutes, the mixture is diluted with saturated aqueous ammonium chloride (20 mL) and extracted with EtOAc (3×15 mL). The combined organic layers are washed with brine (4×5 mL), dried over MgSO$_4$, filtered and concentrated in vacuo. The residue is purified by silica gel chromatography eluting with a gradient of 25-100% EtOAc in hexanes. The resulting solid is triturated with ethyl ether to afford the title compound.

The following compounds are also prepared according to the method described in Example 6:
1-(4-Fluorophenyl)-1H-pyrazolo[3,4-d]pyridazine-4-carboxylic acid [(S)-1-(2-methanesulfonyl-pyridin-4-yl)-propyl]-amide;

1-(4-Fluorophenyl)-1H-pyrazolo[3,4-d]pyridazine-4-carboxylic acid [(S)-1-(2-methanesulfonyl-pyridin-4-yl)-ethyl]-amide; and
1-(4-Fluorophenyl)-1H-pyrazolo[3,4-d]pyridazine-4-carboxylic acid [(S)-1-(6-methanesulfonyl-pyridin-3-yl)-propyl]-amide.

The following compounds are prepared from 3-(4-fluorophenyl)-imidazo[1,5-a]pyrazine-8-carboxylic acid according to the method described in Example 6:
3-(4-Fluorophenyl)-imidazo[1,5-a]pyrazine-8-carboxylic acid [(S)-1-(2-methanesulfonyl-pyridin-4-yl)-propyl]-amide;
3-(4-Fluorophenyl)-imidazo[1,5-a]pyrazine-8-carboxylic acid [(S)-1-(2-methanesulfonyl-pyridin-4-yl)-butyl]-amide;
3-(4-Fluorophenyl)-imidazo[1,5-a]pyrazine-8-carboxylic acid (2-methanesulfonyl-pyridin-4-ylmethyl)-amide;
3-(4-Fluorophenyl)-imidazo[1,5-a]pyrazine-8-carboxylic acid [1-(2-bromopyridin-4-yl)-1-methyl-ethyl]-amide;
3-(4-Fluorophenyl)-imidazo[1,5-a]pyrazine-8-carboxylic acid [1-(2-methanesulfonyl-pyridin-4-yl)-cyclopropyl]-amide; and
3-(4-Fluorophenyl)-imidazo[1,5-a]pyrazine-8-carboxylic acid [(S)-1-(5-methanesulfonyl-pyridin-3-yl)-butyl]-amide.

Example 7

Synthesis of 3-(4-Fluorophenyl)-imidazo[1,5-a]pyridine-8-carboxylic acid (6-methanesulfonyl-pyridin-3-ylmethyl)-amide (7)

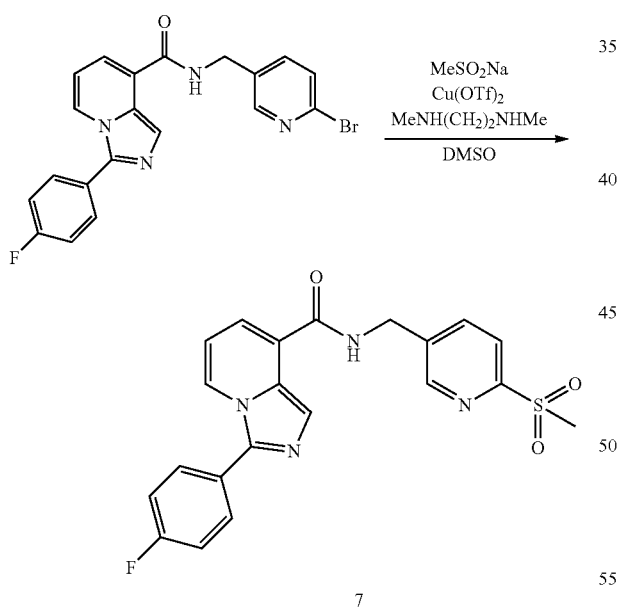

To a solution of 3-(4-fluorophenyl)-imidazo[1,5-a]pyridine-8-carboxylic acid (6-bromopyridin-3-ylmethyl)-amide (133 mg, 0.313 mmol) in DMSO (2 mL) in a microwave tube is added sodium methanesulfinate (52.0 mg, 0.509 mmol), copper (II) trifluoromethanesulfonate (115 mg, 0.318 mmol) and N,N'-dimethylethylene diamine (0.100 mL, 0.939 mmol). The mixture is warmed at 110° C. for 35 minutes in a microwave reactor. The reaction is the diluted with saturated aqueous ammonium chloride (7 mL) and extracted with EtOAc (4×7 mL). The combined organic layers are washed with saturated aqueous ammonium chloride (3×7 mL) and brine (3×7 mL), dried over magnesium sulfate, filtered and concentrated. The residue is purified by silica gel chromatography eluting with a gradient of 0.5-3% methanol in dichloromethane. The resulting solid is triturated with dichloromethane-ether to afford the title compound.

The following compounds are prepared according to the method described in Example 7:
3-(4-Fluorophenyl)-imidazo[1,5-a]pyridine-8-carboxylic acid [(S)-1-(2-methanesulfonyl-pyridin-4-yl)-propyl]-amide;
3-(4-Fluorophenyl)-imidazo[1,5-a]pyridine-8-carboxylic acid (2-methanesulfonyl-pyridin-4-ylmethyl)-amide;
3-(4-Fluorophenyl)-imidazo[1,5-a]pyridine-8-carboxylic acid [(S)-1-(6-methanesulfonyl-pyridin-3-yl)-propyl]-amide; and
1-(4-Fluorophenyl)-imidazo[1,5-a]pyridine-5-carboxylic acid [(S)-1-(6-methanesulfonyl-pyridin-3-yl)-propyl]-amide.

The following compound is prepared from 6-cyano-1-(4-fluorophenyl)-1H-indole-4-carboxylic acid (6-bromopyridin-3-ylmethyl)-amide according to the method described in Example 7:
6-Cyano-1-(4-fluorophenyl)-1H-indole-4-carboxylic acid (6-methanesulfonyl-pyridin-3-ylmethyl)-amide.

Example 8

Synthesis of 3-(4-Fluorophenyl)-imidazo[1,5-a]pyridine-8-carboxylic acid 3-trifluoromethyl-benzylamide (8)

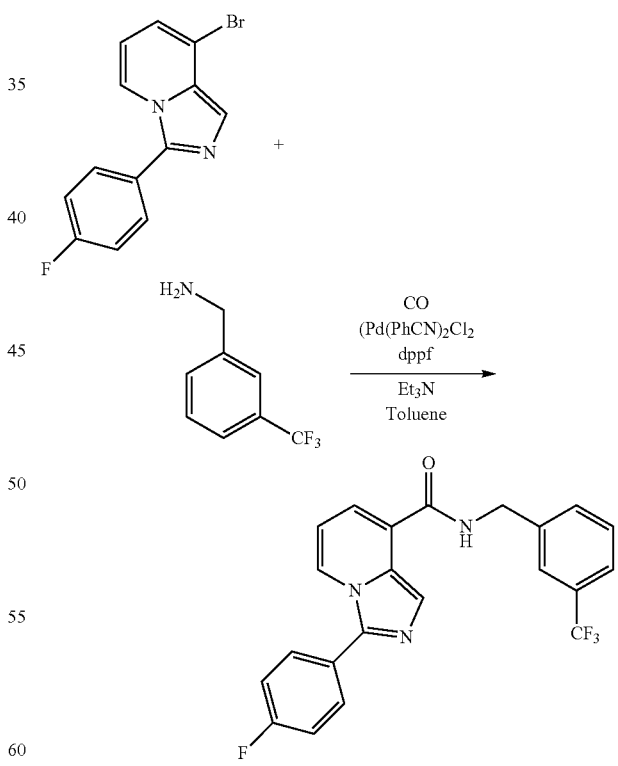

A mixture of 8-bromo-3-(4-fluorophenyl)-imidazo[1,5-a]pyridine (0.100 g, 0.344 mmol), Et$_3$N (95.0 µL, 0.683 mmol), 3-(trifluoromethyl)benzylamine (89.0 µL, 0.621 mmol), Pd[PhCN]$_2$Cl$_2$ (5.0 mg, 0.013 mmol), and dppf (21 mg, 0.038 mmol) in degassed toluene (10 mL) is placed in a pressure reactor. The stirred mixture is placed under 15 bars of carbon monoxide and warmed at 140° C. After 3 hours, the pressure reactor is cooled to room temperature, returned to atmospheric pressure and opened. The reaction mixture is diluted with saturated aqueous ammonium chloride (10 mL) and extracted with EtOAc (3×10 mL). The combined organic layers are washed with saturated aqueous ammonium chloride (3×10 mL), brine (10 mL), dried over magnesium sulfate, filtered and concentrated. The residue is purified by silica gel chromatography eluting with a gradient of 0-50% EtOAc in dichloromethane. The resulting solid is triturated with ether-hexanes to afford the title compound.

The following compound is prepared from 4-chloro-1-(4-fluorophenyl)-1H-pyrazolo[3,4-d]pyrimidine according to the method described in Example 8:
1-(4-Fluorophenyl)-1H-pyrazolo[3,4-d]pyrimidine-4-carboxylic acid 3-trifluoromethyl-benzylamide.

The following compound is prepared from 8-bromo-3-(3,4-dichloro-phenyl)-imidazo[1,5-a]pyridine according to the method described in Example 8:
3-(3,4-Dichloro-phenyl)-imidazo[1,5-a]pyridine-8-carboxylic acid 3-trifluoromethyl-benzylamide.

Example 9

Synthesis of 3-(4-Fluorophenyl)-imidazo[1,2-a]pyridine-8-carboxylic acid (9)

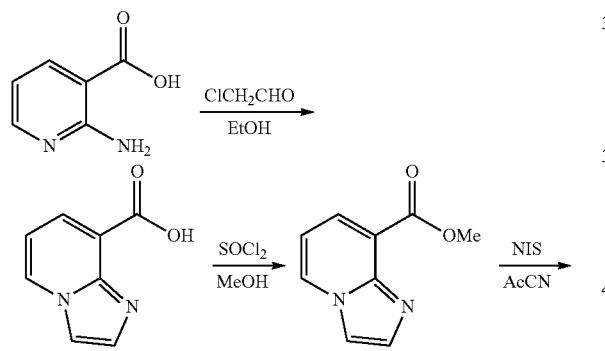

Chloroacetaldehyde (45% aqueous solution) (6.6 mL, 38 mmol) is added to the stirred solution of 2-aminonicotinic acid (5.0 g, 25 mmol) in ethanol (35 mL) and warmed at reflux for 14 hours. The reaction mixture is concentrated and the crude material is triturated with EtOH-Et$_2$O to afford imidazo[1,2-a]pyridine-8-carboxylic acid. Mp: 296-299° C.

To a stirred solution of imidazo[1,2-a]pyridine-8-carboxylic acid (3.8 g, 23 mmol) in methanol (100 mL) is added thionylchloride (8.36 g, 70.3 mmol) and the mixture is warmed at reflux. After 8 hours, the reaction mixture is cooled to room temperature and quenched with saturated aqueous NaHCO$_3$, and extracted with EtOAc (3×250 mL). The combined organic layers are washed with water, brine, dried over Na$_2$SO$_4$ and concentrated. The crude material is purified by silica gel chromatography eluting with 3% MeOH in CH$_2$Cl$_2$ to afford imidazo[1,2-a]pyridine-8-carboxylic acid methyl ester. Mp: 71-73° C.

A mixture of imidazo[1,2-a]pyridine-8-carboxylic acid methyl ester (3.24 g, 18.3 mmol) and N-iodosuccinimide (NIS) (4.11 g, 18.3 mmol) in acetonitrile (50 mL) is stirred at room temperature. After 2 hours, the reaction mixture is quenched with saturated aqueous Na$_2$S$_2$O$_3$ and extracted with EtOAc (3×100 mL). The combined organic layers are washed with water, brine, dried over Na$_2$SO$_4$ and concentrated. The crude material is purified by silica gel chromatography eluting with 80% EtOAc in hexanes to afford 3-iodo-imidazo[1,2-a]pyridine-8-carboxylic acid methyl ester. Mp: 99-110° C.

To a degassed (with Argon gas) solution of 3-iodo-imidazo[1,2-a]pyridine-8-carboxylic acid methyl ester (2.2 g, 7.3 mmol) and 4-fluorophenyl boronic acid (1.48 g, 9.44 mmol) in a 1:1 mixture of ethanol-benzene (100 mL) is added an aqueous solution of 2 M sodium carbonate (9 mL, 18 mmol) and tetrakis(triphenylphosphine) palladium (0) (0.42 g, 0.36 mmol) and the reaction mixture is warmed at reflux. After 16 hours, the reaction mixture is filtered through filter agent washing with EtOAc. The filtrate is diluted with water and the organic layer is separated. The pH of the aqueous layer is adjusted to 4-5 with 6 N aqueous HCl. The solid is collected by filtration and triturated with Et$_2$O to afford the title compound. Mp: >400° C.

Example 10

Synthesis of 1-(4-Fluorophenyl)-imidazo[1,5-a]pyridine-5-carboxylic acid (10)

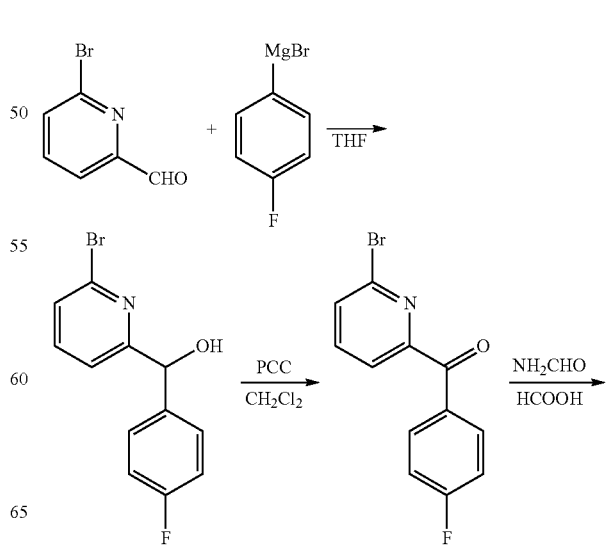

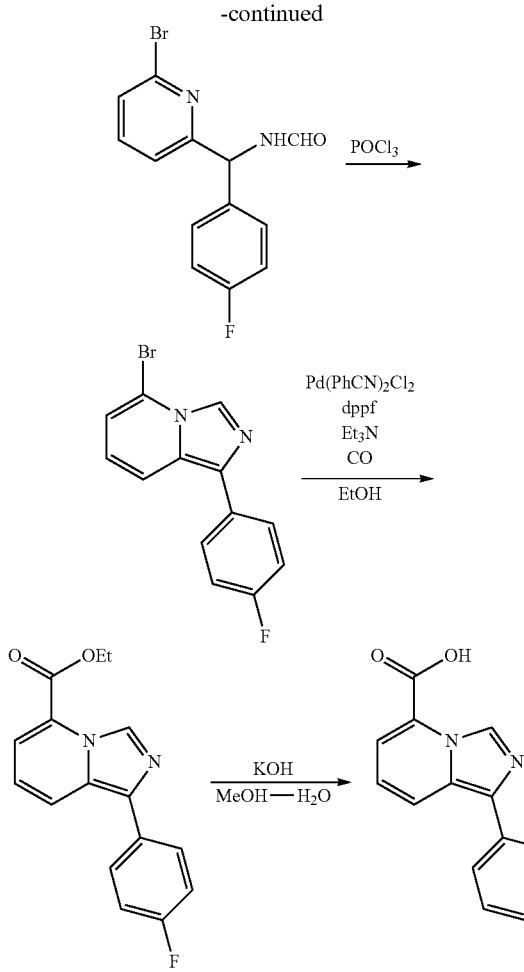

To a chilled (−10° C.) solution of 6-bromopyridine-2-carboxaldehyde (5.0 g, 27 mmol) in THF (108 mL) is added a 1 M solution of 4-fluorophenylmagnesium bromide in THF (30 mL, 30 mmol). The temperature is allowed to slowly warm to room temperature over 30 minutes and then the reaction mixture is quenched with saturated aqueous NH$_4$Cl (100 mL) and extracted with EtOAc (3×100 mL). The combined organic layers are dried over Na$_2$SO$_4$ and concentrated. The crude material is purified by silica gel chromatography eluting with 15% EtOAc-hexanes to afford (6-bromopyridin-2-yl)-(4-fluorophenyl)-methanol.

To a chilled (0° C.) solution of (6-bromopyridin-2-yl)-(4-fluorophenyl)-methanol (6.2 g, 22 mmol) in dichloromethane (88 mL) is added pyridinium chlorochromate (PCC) (7.1 g, 33 mmol). The reaction mixture is allowed to warm to room temperature. After 5 hours, the reaction mixture is concentrated and purified by silica gel chromatography eluting with 10% EtOAc in hexanes to afford (6-bromopyridin-2-yl)-(4-fluorophenyl)-methanone.

A stirred mixture of 6-bromopyridin-2-yl)-(4-fluorophenyl)-methanone (5.4 g, 19 mmol) and formic acid (27.5 g, 598 mmol) in formamide (193 mL) is warmed at 180° C. After 1 hour, the reaction mixture is diluted with water (100 mL) and extracted into EtOAc (3×200 mL). The combined organic layers are washed with water, brine, dried over Na$_2$SO$_4$ and concentrated to afford N-[(6-bromopyridin-2-yl)-(4-fluorophenyl)-methyl]-formamide which is used without further purification.

A stirred mixture of N-[(6-bromopyridin-2-yl)-(4-fluorophenyl)-methyl]-formamide (6.4 g, 21 mmol) in POCl$_3$ (41 mL) is warmed at reflux. After 1 hour, the reaction mixture is cautiously quenched by a slow addition to saturated aqueous NaHCO$_3$ and the mixture is extracted into EtOAc (3×200 mL). The combined organic layers are dried over Na$_2$SO$_4$ and concentrated. The crude material is purified by silica gel chromatography eluting with 30% EtOAc in hexanes to afford 5-bromo-1-(4-fluorophenyl)-imidazo[1,5-a]pyridine.

To a autoclave flask, charged with 5-bromo-1-(4-fluorophenyl)-imidazo[1,5-a]pyridine (4.2 g, 15 mmol) in ethanol (500 mL) is added Et$_3$N (4.20 mL, 30.5 mmol), dppf (0.48 g, 0.87 mmol), and Pd(PhCN)$_2$Cl$_2$ (0.11 g, 0.29 mmol) and the mixture is warmed at 140° C. under an atmosphere of carbon monoxide (15 kg). After 2 hours, the autoclave is allowed to come to room temperature and is opened and the mixture is concentrated. The residue is diluted with water and extracted into EtOAc (3×200 mL). The combined organic layers are washed with water, brine, dried over Na$_2$SO$_4$ and concentrated. The crude product is purified by silica gel chromatography eluting with 10% EtOAc in hexanes to afford 1-(4-fluorophenyl)-imidazo[1,5-a]pyridine-5-carboxylic acid ethyl ester.

To a stirred solution of 1-(4-fluorophenyl)-imidazo[1,5-a]pyridine-5-carboxylic acid ethyl ester (2.0 g, 7.0 mmol) in MeOH (233 mL) is added a solution of 85% KOH (4.6 g, 69 mmol) in H$_2$O (35 mL) and the mixture is warmed at reflux. After 15 minutes, the reaction mixture is evaporated, diluted with water, and washed with EtOAc (2×200 mL). The aqueous layer is acidified with 1 N aqueous HCl (pH 5-6) to afford a precipitate. The solid is collected by filtration and triturated with 10% MeOH—CH$_2$Cl$_2$ to provide the title compound.

Example 11

Synthesis of (S)-1-(2-Methanesulfonyl-thiazol-5-yl)-propylamine hydrochloride (11)

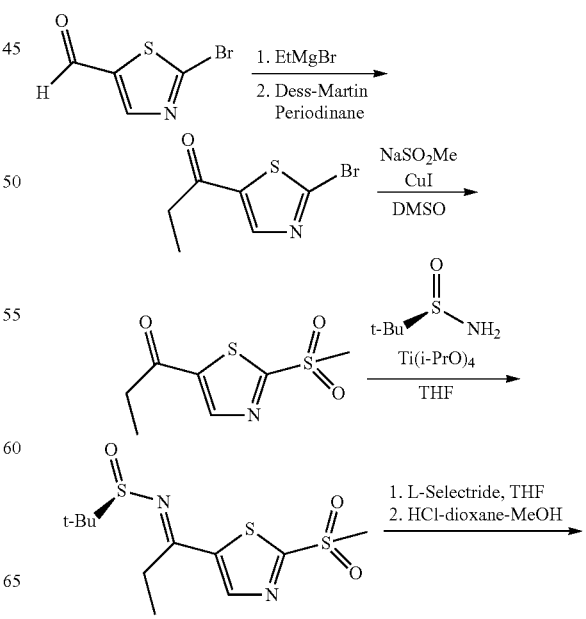

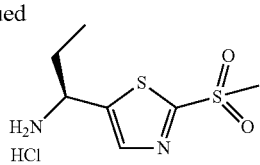

To a solution of 2-bromo-thiazole-5-carboxaldehyde (1.00 g, 5.21 mmol) in THF (10 mL) is added a 3 M solution of ethylmagnesium bromide (5.00 mL, 15.0 mmol) in diethyl ether. After 18 hours, the reaction is poured into saturated aqueous ammonium chloride (100 mL) containing crushed ice and diluted with EtOAc (100 mL). The organic phase is separated, washed with saturated aqueous sodium bicarbonate solution (100 mL), dried over sodium sulfate, filtered and concentrated. The compound is purified by silica gel chromatography eluting using a gradient of 0-100% EtOAc in hexanes to provide 1-(2-bromo-thiazol-5-yl)-propan-1-ol.

To a solution of 1-(2-bromo-thiazol-5-yl)-propan-1-ol (180 mg, 0.79 mmol) in dichloromethane (10 mL) is added Dess-Martin periodinane (DMP) (330 mg, 0.79 mmol). After 2 hours, the mixture is diluted with dichloromethane (50 mL), washed with saturated aqueous sodium bicarbonate (50 mL), brine (50 mL), dried over sodium sulfate, filtered and concentrated. The mixture is purified by silica gel chromatography eluting with a gradient of 0-100% EtOAc in hexanes to afford 1-(2-bromo-thiazol-5-yl)-propan-1-one.

To a solution of 1-(2-bromo-thiazol-5-yl)-propan-1-one (75 mg, 0.34 mmol) in DMSO (3 mL) is added sodium methanesulfonate (41 mg, 0.34 mmol) followed by copper (I) iodide (65 mg, 0.34 mmol). The mixture is warmed in a microwave reactor at 120° C. After 1 hour, the reaction is diluted with EtOAc (20 mL) and washed with saturated aqueous sodium bicarbonate (50 mL) and brine (10 mL). The aqueous phase is extracted with EtOAc (2×10 mL). The combined organic layers are dried over magnesium sulfate, filtered and concentrated to afford 1-(2-methanesulfonyl-thiazol-5-yl)-propan-1-one which is used without further purification.

A mixture of 1-(2-methanesulfonyl-thiazol-5-yl)-propan-1-one (110 mg, 0.50 mmol), (R)-2-methyl-2-propanesulfinamide (70 mg, 0.6 mmol) and titanium (IV) isopropoxide (0.29 mL, 1.0 mmol) in THF (10 mL) is warmed at reflux. After 18 hours, the mixture is cooled to room temperature and diluted with diethyl ether (100 mL) and water (6 mL). After 10 minutes with stirring, the solution is dried over sodium sulfate, filtered and concentrated. The crude product is purified by silica gel chromatography eluting with a gradient of 0-100% EtOAc in hexanes to afford 2-methyl-propane-2-sulfinic acid [1-(2-methanesulfonyl-thiazol-5-yl)-prop-(Z)-ylidene]-amide.

To a chilled (−78° C.) solution of 2-methyl-propane-2-sulfinic acid [1-(2-methanesulfonyl-thiazol-5-yl)-prop-(Z)-ylidene]-amide (93 mg, 0.29 mmol) in THF (5 mL) is added a 1 M solution of lithium tri-sec-butylborohydride (L-Selectride) (0.58 mL, 0.58 mmol) in THF dropwise. After 2.5 hours, the reaction mixture is quenched with saturated aqueous ammonium chloride solution (100 mL), and the aqueous layer is separated. The aqueous layer is extracted with EtOAc (2×10 mL). The combined organic layers are washed with brine (10 mL), dried over sodium sulfate, filtered and concentrated. The residue is purified by silica gel chromatography eluting using a gradient of 0-100% EtOAc in hexanes to afford 2-methyl-propane-2-sulfinic acid [(S)-1-(2-methanesulfonyl-thiazol-5-yl)-propyl]-amide.

To a solution of 2-methyl-propane-2-sulfinic acid [(S)-1-(2-methanesulfonyl-thiazol-5-yl)-propyl]-amide (80 mg, 0.3 mmol) in methanol (5 mL) is added a 4 N solution of hydrochloric acid (1 mL, 4 mmol) in dioxane. After 1 hour, the mixture is concentrated and diluted with dichloromethane (2 mL) followed by hexanes (10 mL), and concentrated to afford (S)-1-(2-methanesulfonyl-thiazol-5-yl)-propylamine hydrochloride.

Example 12

Synthesis of (S)-1-(2-Methanesulfonyl-pyridin-4-yl)-propylamine hydrochloride salt (12)

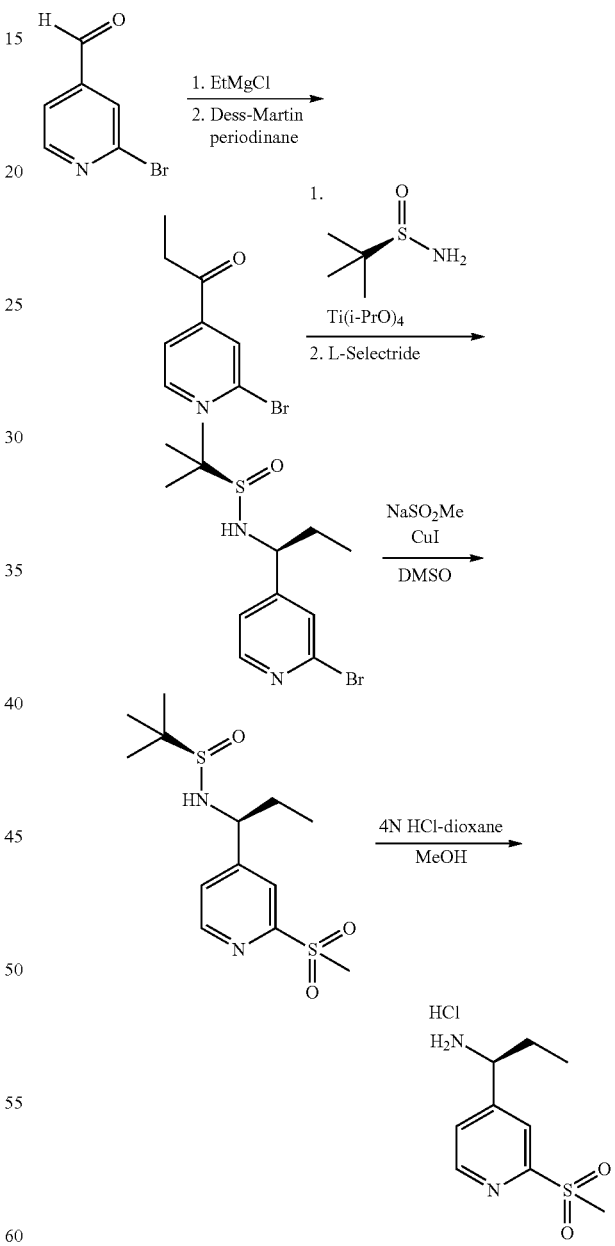

To a chilled (−78° C.) solution of 2-bromopyridine-4-carboxaldehyde (7.0 g, 38 mmol) in THF (200 mL) is added a 2 M solution of ethylmagnesium chloride in ether (23.5 mL, 47.0 mmol) over a 10 minute period. After 15 minutes, the mixture is gradually warmed to room temperature over 1 hour. The reaction is quenched by the slow addition of saturated aqueous NH₄Cl (100 mL) and extracted with EtOAc (2×200 mL). The combined organic layers are washed with brine, dried over sodium sulfate, filtered and concentrated. The crude material is purified by silica gel chromatography eluting with a gradient of 20-40% EtOAc in hexanes to afford 1-(2-bromopyridin-4-yl)-propan-1-ol.

To a solution of 1-(2-bromopyridin-4-yl)-propan-1-ol (2.20 g 10.2 mmol) in dichloromethane (55 mL) is added Dess-Martin periodinane (5.6 g, 13 mmol). After 30 hours, the mixture is diluted with saturated aqueous sodium carbonate (40 mL) and partially concentrated to remove the dichloromethane. The crude material is filtered through filter agent and washed with EtOAc (100 mL). The aqueous layer is separated and extracted with EtOAc (40 mL). The combined organic layers are washed with saturated aqueous sodium carbonate (40 mL) and brine (40 mL). The material is dried over magnesium sulfate, filtered and concentrated to afford 1-(2-bromopyridin-4-yl)-propan-1-one as an oil which is used without further purification.

Alternatively, the intermediate ketone, 1-(2-bromopyridin-4-yl)-propan-1-one, can be prepared via a Grignard addition to a Weinreb amide derived from commercially available 2-bromo-isonicotinic acid.

A solution of 1-(2-bromopyridin-4-yl)-propan-1-one (8.9 g, 42 mmol), R-(+)-2-methylpropane-2-sulfinamide (6 g, 50 mmol) and titanium (IV) isopropoxide (26 g, 91 mmol) in anhydrous dichloromethane (50 mL) is warmed at 40° C. for 18 hours. After cooling, the solution is concentrated and EtOAc (100 mL) is added. The solution is stirred and brine (100 mL) is added slowly. After 15 minutes, the mixture is filtered through a pad of filter agent and washed with EtOAc (100 mL). The organic layers are separated, dried over sodium sulfate, and concentrated. The product is purified by silica gel chromatography eluting with a gradient of 0-50% EtOAc in hexanes to afford 2-methyl-propane-2-sulfinic acid [1-(2-bromopyridin-4-yl)-prop-(E)-ylidene]-amide.

To a chilled (−78° C.) solution of 2-methyl-propane-2-sulfinic acid [1-(2-bromopyridin-4-yl)-prop-(E)-ylidene]-amide (6.0 g, 19 mmol) in THF (280 mL) is added a 1 M solution of L-Selectride in THF (37.8 mL, 37.8 mmol) dropwise. After 2.5 hours, the reaction mixture is quenched with saturated aqueous NH₄Cl (100 mL). The layers are separated and the aqueous layer is extracted with EtOAc (2×400 mL). The combined organic layers are washed with brine, and concentrated. The residue is purified by silica gel chromatography eluting with a gradient of 0-100% EtOAc in hexanes to afford an oily solid, which after further drying gives 2-methyl-propane-2-sulfinic acid [(R)-1-(2-bromopyridin-4-yl)-propyl]-amide as a crystalline solid.

To a solution of 2-methyl-propane-2-sulfinic acid [(R)-1-(2-bromopyridin-4-yl)-propyl]-amide (6.00 g, 18.8 mmol) in DMSO (240 mL) is added sodium methanesulfinate (6.77 g, 56.4 mmol) and copper (I) iodide (10.7 g, 56.4 mmol). The mixture is then heated at 130° C. for 45 minutes. The reaction is diluted with saturated aqueous NH₄Cl (90 mL), saturated NaHCO₃ (10 mL), and EtOAc (150 mL), and sonicated for 10 minutes to dissolve all the solids. The phases are separated and the organic layer is washed with a 9:1 mixture of saturated NH₄Cl-saturated NaHCO₃ (100 mL). The combined aqueous phases are extracted with EtOAc (150 mL). Combined organic layers are washed with brine, dried over sodium sulfate, filtered and concentrated. The crude material is purified by silica gel chromatography eluting with a gradient of 0-100% EtOAc in hexanes to afford 2-methyl-propane-2-sulfinic acid [(S)-1-(2-methanesulfonyl-pyridin-4-yl)-propyl]-amide as an oil.

Alternatively, (1-(2-bromopyridin-4-yl)-propan-1-one could be converted to the corresponding methyl sulfone via the above procedure to afford 1-(2-methanesulfonyl-pyridin-4-yl)-propan-1-one. 1-(2-Methanesulfonyl-pyridin-4-yl)-propan-1-one can be converted to the title compound by methods described in example 12.

To a solution of 2-methyl-propane-2-sulfinic acid [(S)-1-(2-methanesulfonyl-pyridin-4-yl)-propyl]-amide (26 g, 82 mmol) in methanol (150 mL) is added a solution of 4 N HCl in dioxane (22.5 mL, 89.8 mmol). After 1 hour, the solution is concentrated to half the original volume and diluted with toluene (100 mL), and concentrated. The crude material is co-evaporated from toluene (3×100 mL) and dried in vacuo for 18 hours to afford the title compound as a solid.

Example 13

Synthesis of (R)-1-(2-bromopyridin-4-yl)-2-methoxy-ethylamine ditrifloroacetic acid salt (13)

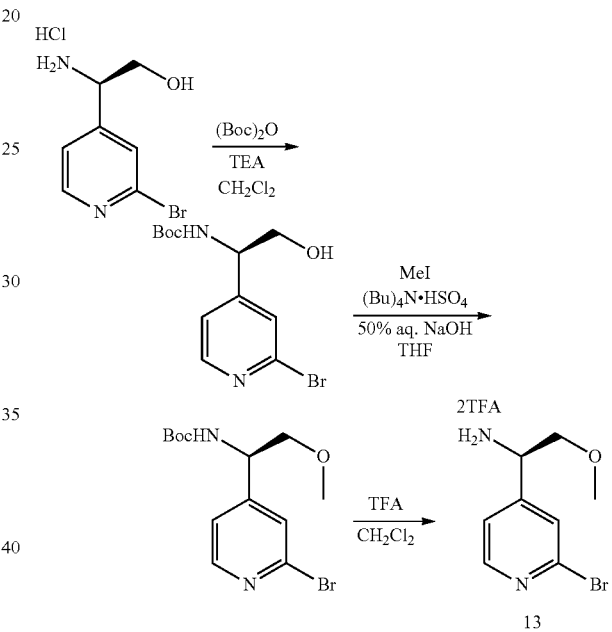

To a suspension of (R)-2-amino-2-(2-bromopyridin-4-yl)-ethanol hydrochloride salt (180 mg, 0.71 mmol) in methylene chloride (5 mL) is added triethylamine (370 μL, 2.13 mmol) and di-tert-butyl dicarbonate (186 mg, 0.852 mmol). After 16 hours, the mixture is diluted with methylene chloride (20 mL), washed with saturated aqueous ammonium chloride (20 mL), saturated aqueous sodium bicarbonate (20 mL) and brine (20 mL), dried over MgSO₄, filtered and concentrated in vacuo. The resulting residue is purified by silica gel chromatography eluting with a gradient of 0-10% methanol in methylene chloride to afford [(R)-1-(2-bromopyridin-4-yl)-2-hydroxy-ethyl]-carbamic acid tert-butyl ester as foam. MS m/z 317.1, 319.0.

To a solution of [(R)-1-(2-bromopyridin-4-yl)-2-hydroxyethyl]-carbamic acid tert-butyl ester (180 mg, 0.57 mmol), methyl iodide (177 μL, 2.84 mmol) and tetrabutylammonium hydrogen sulfate (192 mg, 0.568 mmol) in THF (4.0 mL) is added 50% aqueous sodium hydroxide (2.5 mL). After 1 hour, the reaction mixture is diluted with water (50 mL) and extracted with ethyl ether (3×50 mL). The combined organic layers are dried over MgSO₄, filtered and concentrated in vacuo. The residue is purified by silica gel chromatography eluting with a gradient of 0-30% EtOAc in heptane to afford

[(R)-1-(2-bromopyridin-4-yl)-2-methoxy-ethyl]-carbamic acid tert-butyl ester as oil which solidified upon standing.

To a solution of [(R)-1-(2-bromopyridin-4-yl)-2-methoxy-ethyl]-carbamic acid tert-butyl ester (150 mg, 0.45 mmol) in CH$_2$Cl$_2$ (3 mL) is added trifluoroacetic acid (872 µL, 11.3 mmol). After 14 hours, the mixture is concentrated in vacuo to afford the title compound which is used without purification. MS m/z 231.0, 233.0.

Example 14

Synthesis of (S)-1-(2-Methanesulfonyl-pyridin-4-yl)-ethylamine hydrochloride (14)

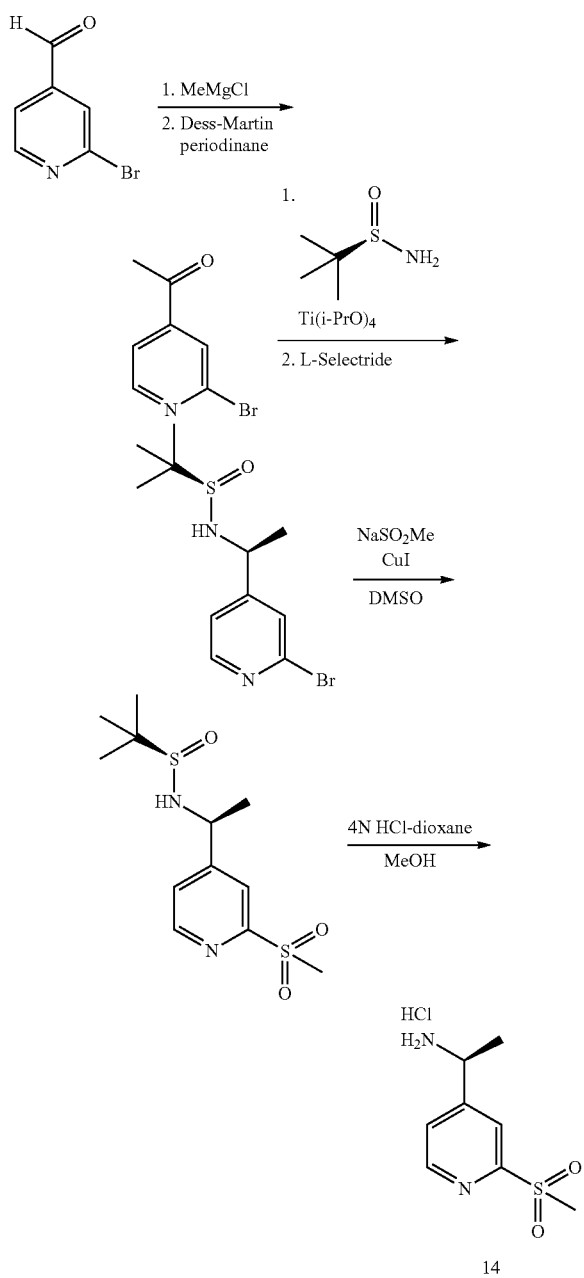

14

To a chilled (−78° C.) solution of 2-bromopyridine-4-carboxaldehyde (10.0 g, 53.8 mmol) in THF (100 mL) is added a 3 M solution of methylmagnesium chloride in THF (18 mL, 54 mmol) over a 10 minute period. After 1 hour, the solution is allowed to warm gradually to room temperature over a 3 hour period. The reaction is quenched by the slow addition of saturated aqueous NH$_4$Cl (50 mL) and extracted with EtOAc (2×200 mL). The combined organic layers are washed with brine, dried over sodium sulfate, and concentrated to afford an oil. The crude material is purified by silica gel chromatography eluting with a gradient of 10-45% EtOAc in hexanes to afford 1-(2-bromopyridin-4-yl)-ethanol.

To a chilled (ice water bath) solution of 1-(2-bromopyridin-4-yl)-ethanol (27.5 g, 132 mmol) in dichloromethane (200 mL) is added Dess-Martin periodinane (56.0 g, 132 mmol). The cold bath is then removed and the mixture is stirred at room temperature. After 2 hours, the mixture is diluted with saturated sodium carbonate (100 mL) and partially concentrated to remove the dichloromethane. The crude material is filtered through filter agent and washed with EtOAc (200 mL). The aqueous layer is separated and extracted with EtOAc (100 mL). The combined organic layers are washed with saturated aqueous sodium carbonate (100 mL), brine (100 mL), dried over magnesium sulfate, filtered and concentrated. The crude material is purified by silica gel chromatography eluting with a gradient of 5-30% EtOAc in hexanes to afford 1-(2-bromopyridin-4-yl)-ethanone as needles.

Alternatively, the intermediate ketone (1-(2-bromopyridin-4-yl)-ethanone) can be accessed via a Grignard addition to a Weinreb amide derived from commercially available 2-bromo-isonicotinic acid.

A solution of 1-(2-bromopyridin-4-yl)-ethanone (8 g, 40 mmol), R-(+)-2-methylpropane-2-sulfinamide (5.8 g, 48 mmol) and titanium (IV) isopropoxide (25.7 mL, 87.8 mmol) in anhydrous dichloromethane (10 mL) is heated at 60° C. After 18 hours, the mixture is cooled and concentrated. The residue is diluted with EtOAc (300 mL) and brine (50 mL) is added slowly to the stirred mixture. After 15 minutes, the mixture is filtered through filter agent and washed with EtOAc (100 mL). The organic phase is separated, dried over sodium sulfate, and concentrated. The product is purified by silica gel chromatography eluting with a gradient of 0-50% EtOAc in hexanes to afford 2-methyl-propane-2-sulfinic acid [1-(2-bromopyridin-4-yl)-eth-(E)-ylidene]-amide.

To a chilled (−78° C.) solution of 2-methyl-propane-2-sulfinic acid [1-(2-bromopyridin-4-yl)-eth-(E)-ylidene]-amide (9.3 g, 31 mmol) in THF (280 mL) is added a 1 M solution of L-Selectride in THF (61.3 mL, 61.3 mmol) dropwise. After 2.5 hours, the chilled mixture is quenched with saturated aqueous NH$_4$Cl (100 mL). The layers are separated and the aqueous layer is extracted with EtOAc (2×400 mL). The combined organic layers are washed with brine, and concentrated. The residue is purified by silica gel chromatography eluting with a gradient of 50-90% EtOAc in hexanes to afford 2-methyl-propane-2-sulfinic acid [(S)-1-(2-bromopyridin-4-yl)-ethyl]-amide as an oil which contained 5% of the opposite diastereomer.

To a solution of 2-methyl-propane-2-sulfinic acid [(S)-1-(2-bromopyridin-4-yl)-ethyl]-amide (3.10 g, 10.2 mmol) (containing 5 wt % of the other diastereomer) in DMSO (120 mL) is added sodium methanesulfinate (3.7 g, 31 mmol) and copper (I) iodide (5.8 g, 31 mmol). The mixture is warmed at 130° C. for 45 minutes. The reaction is diluted with saturated aqueous NH$_4$Cl (90 mL), saturated aqueous NaHCO$_3$ (10 mL), and EtOAc (150 mL), and sonicated for 10 minutes to dissolve all the solids. The aqueous phase is separated and the organic layer is washed with a mixture of saturated aqueous NH$_4$Cl (90 mL) in saturated aqueous NaHCO$_3$ (10 mL). The combined aqueous layers are extracted with EtOAc (150 mL). The combined organic layers are washed with brine, dried over sodium sulfate, filtered and concentrated. The crude material is purified by silica gel chromatography eluting with a gradient of 75-100% EtOAc in hexanes to afford 2-methylpropane-2-sulfinic acid [(S)-1-(2-methanesulfonyl-pyridin-4-yl)-ethyl]-amide as an oil as a single diastereomer.

Alternatively, (1-(2-bromopyridin-4-yl)-ethanone) could be converted to the corresponding methyl sulfone via the above procedure to afford 1-(2-methanesulfonyl-pyridin-4-yl)-ethanone. 1-(2-Methanesulfonyl-pyridin-4-yl)-ethanone can be converted to the title compound by methods described in example 14.

To a solution of 2-methyl-propane-2-sulfinic acid [(S)-1-(2-methanesulfonyl-pyridin-4-yl)-ethyl]-amide (29.9 g, 98.2 mmol) in methanol (160 mL) is added a solution of 4 N HCl in dioxane (25.8 mL, 103 mmol). After 1 hour, the solution is concentrated to half the original volume and diluted with toluene (100 mL), and concentrated. The crude material is diluted with toluene (3×100 mL) and concentrated in vacuo and dried in vacuo for 18 hours to afford the title compound as a solid which is used without further purification.

Example 15

Synthesis of (S)-1-(4-Bromopyridin-2-yl)-propylamine hydrochloride salt (15)

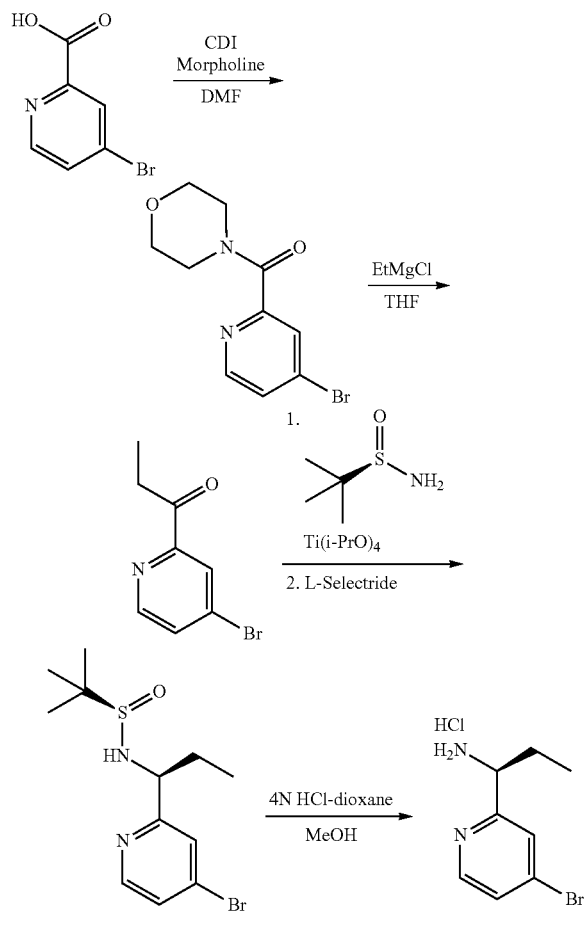

To a solution of 4-bromopyridine-2-carboxylic acid (2.0 g, 9.9 mmol) in DMF (15 mL) is added CDI. After 15 minutes, morpholine (3.0 mL, 34 mmol) is added. The reaction is monitored by HPLC-MS indicating a single peak with the desired mass and the mixture is diluted with saturated aqueous ammonium chloride (60 mL) and extracted with EtOAc (5×50 mL). The combined organic layers are washed with brine (2×30 mL), dried over magnesium sulfate, filtered and concentrated. The crude mixture is purified by silica gel chromatography using dichloromethane to load the sample and then eluting with a gradient of 10-100% EtOAc in hexanes to afford 4-bromopyridin-2-yl)-morpholin-4-yl-methanone.

To a chilled (−78° C.) solution of 4-bromopyridin-2-yl)-morpholin-4-yl-methanone (1.5 g, 5.5 mmol) in THF (30 mL) is added of a 2 M solution of ethyl magnesium chloride (3.5 mL, 7.0 mmol) in THF dropwise. The mixture is diluted with saturated aqueous ammonium chloride (40 mL) and extracted with EtOAc (3×50 mL). The combined organic layers are washed with brine (2×30 mL), dried over magnesium sulfate, filtered and concentrated. The crude material is passed through a pad of silica gel eluting with 5% EtOAc in hexanes to afford 1-(4-bromopyridin-2-yl)-propan-1-one.

A mixture of 1-(4-bromopyridin-2-yl)-propan-1-one (1.0 g, 4.7 mmol), R-(+)-2-methylpropane-2-sulfinamide (711 mg, 5.87 mmol) and titanium (IV) isopropoxide (2 mL, 6.8 mmol) in dichloroethane (10 mL) is warmed at reflux. After 1 hour, the mixture is cooled to room temperature and stirred for 2 days. The mixture is then diluted with dichloromethane (50 mL) and water (2 mL) is added. The mixture is stirred for 10 minutes and then dried over magnesium sulfate, filtered through filter agent and concentrated in vacuo. The residue is purified by silica gel chromatography eluting with EtOAc in hexanes (1:99, then 5:95) to afford 2-methyl-propane-2-sulfinic acid [(S)-1-(4-bromopyridin-2-yl)-propyl]-amide.

To a chilled (−78° C.) solution of 2-methyl-propane-2-sulfinic acid [(S)-1-(4-bromopyridin-2-yl)-propyl]-amide (985 mg, 3.10 mmol) in THF (25 mL) is added a 1 M solution of L-Selectride (3.2 mL, 3.2 mmol) in THF. The reaction is monitored by TLC (EtOAc-ether 3:7) indicating a single diastereomer when compared to a mixture of diastereomers prepared by reduction of 2-methyl-propane-2-sulfinic acid [(S)-1-(4-bromopyridin-2-yl)-propyl]-amide with lithium borohydride in THF. After 3 hours, the mixture is quenched with saturated aqueous ammonium chloride (30 mL) and extracted with EtOAc (3×25 mL). The combined organic layers are washed with brine (3×30 mL), dried over magnesium sulfate, filtered and concentrated. The crude material is purified by silica gel chromatography eluting with a gradient of 0-100% EtOAc in dichloromethane. The material from the column is crystallized from hexanes to afford (S)-1-(4-bromopyridin-2-yl)-propylamine.

A mixture of (S)-1-(4-bromopyridin-2-yl)-propylamine (0.600 g, 1.88 mmol) in 3 N aqueous HCl is stirred for 16 hours. The mixture is then added to a solution of saturated aqueous sodium bicarbonate (15 mL) and extracted with EtOAc (5×15 mL). The combined organic layers are dried over sodium sulfate, filtered and concentrated in vacuo to afford the title compound which is used without purification.

Example 16

Synthesis of (S)-1-(6-Bromopyridin-3-yl)-propylamine dihydrochloride salt (16)

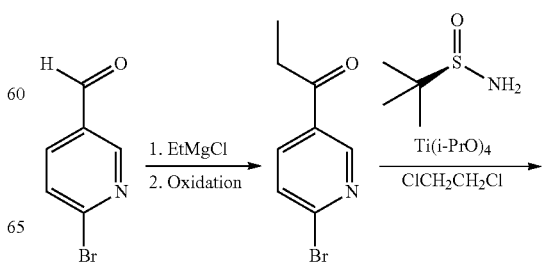

-continued

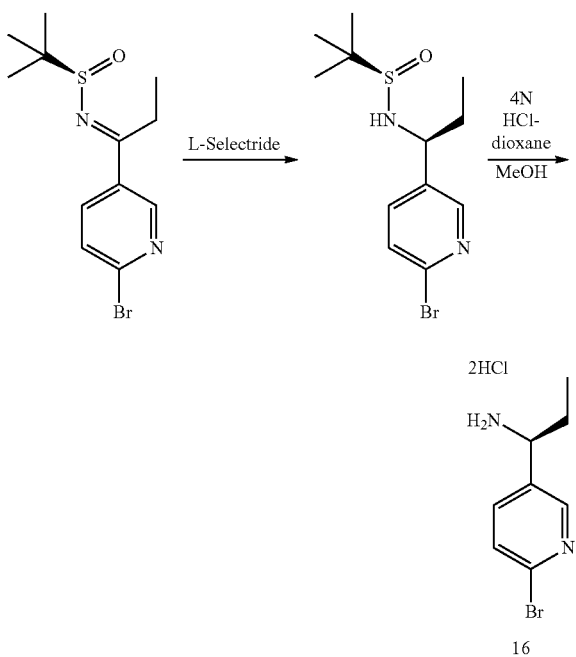

16

To a chilled (0° C.) solution of 6-bromopyridine-3-carboxaldehyde (15.0 g, 80.6 mmol) in a 1:1 mixture of ether-toluene (400 mL) is added a 2 M solution of ethylmagnesium chloride (40.0 mL, 80.0 mmol) in THF over a 15 minute period. After 4 hours, the mixture is diluted with saturated aqueous ammonium chloride (300 mL) and the organic layer is separated. The aqueous layer is extracted with EtOAc (2×100 mL). The combined organic layers are washed with brine (2×50 mL), dried over magnesium sulfate, filtered and concentrated. The crude material is passed through a pad of silica gel eluting with dichloromethane-hexanes (0-100%). The material from the pad is purified by silica gel chromatography eluting with EtOAc-hexanes (2:98, then 4:96, then 6:94, then 8:92, then 1:9, then 12:88, then 15:85) to afford 1-(6-bromopyridin-3-yl)-propan-1-ol as an oil.

Reacting 6-bromopyridine-3-carboxaldehyde with propylmagnesium chloride according to the above method gives the following analog:

1-(6-bromopyridin-3-yl)-butan-1-ol.

To a solution of 1-(6-bromopyridin-3-yl)-propan-1-ol (12.9 g, 59.9 mmol) in THF (200 mL) is added 85% activated MnO$_2$ (6.4 g, 63 mmol) and the mixture is stirred overnight. The reaction is monitored by TLC (EtOAc-hexanes 4:6) indicating starting material and a new less polar product. To the mixture is added additional 85% activated MnO$_2$ (6.0 g, 58.66 mmol) and the mixture stirred for 2 days. The reaction is monitored by TLC (EtOAc-hexanes 3:7) indicating starting material is still present. The mixture is warmed at reflux for 6 hours. The mixture is filtered through filter agent and concentrated. The residue is diluted with dichloromethane and Dess-Martin periodinane (19 g, 44.8 mmol) is added. After 1 hour, the mixture is diluted with saturated aqueous potassium carbonate (200 mL) and concentrated. The resulting solid is collected by filtration washing with water and dried. The solid is suspended in dichloromethane and filtered and the filtrate is passed through a pad of silica gel eluting with ether to afford 1-(6-bromopyridin-3-yl)-propan-1-one as a solid.

Reacting (1-(6-bromopyridin-3-yl)-butan-1-ol according to the above method gives the following analog:

1-(6-Bromopyridin-3-yl)-butan-1-one.

A mixture of 1-(6-bromopyridin-3-yl)-propan-1-one (11.8 g, 55.12 mmol), R-(+)-2-methylpropane-2-sulfinamide (8.0 g, 66.01 mmol) and titanium (IV) isopropoxide (18.0 mL, 61.43 mmol) in dichloroethane (65 mL) is warmed at reflux. After 2 days, the mixture is diluted with dichloromethane (600 mL) and water (15 mL) is added. After 10 minutes of stirring, the mixture is dried over magnesium sulfate, filtered through filter agent and concentrated. The residue is purified by silica gel chromatography eluting with a gradient of 0-40% EtOAc in hexanes and then a gradient of 0-40% EtOAc in dichloromethane to afford 2-methyl-propane-2-sulfinic acid [1-(6-bromopyridin-3-yl)-prop-(E)-ylidene]-amide.

Reacting 1-(6-bromopyridin-3-yl)-butan-1-one according to the above method gives the following analog:

2-Methyl-propane-2-sulfinic acid [1-(6-bromopyridin-3-yl)-but-(E)-ylidene]-amide.

To a chilled (−78° C.) solution of 2-methyl-propane-2-sulfinic acid [1-(6-bromopyridin-3-yl)-prop-(E)-ylidene]-amide (10.4 g, 32.78 mmol) in THF (150 mL) is added a 1 M solution of L-Selectride (33.0 mL, 33.0 mmol) in THF. The reaction is monitored by TLC (EtOAc-ether 3:7) indicating a single diastereomer (when compared to a mixture of diastereomers prepared by a reduction of 2-methyl-propane-2-sulfinic acid [1-(6-bromopyridin-3-yl)-prop-(E)-ylidene]-amide with lithium borohydride in THF). After 6 hours, the mixture is quenched with saturated aqueous ammonium chloride (100 mL) and extracted with EtOAc (3×100 mL). The combined organic layers are washed with saturated aqueous ammonium chloride (2×50 mL), brine (50 mL), dried over magnesium sulfate, filtered and concentrated. The crude material is purified by silica gel chromatography eluting with ether-dichloromethane (0:100, then 5:95, then 1:9, then 2:8). The material from the chromatography is triturated with ether to afford in two crops material which by $^1$H NMR is consistent with a single diastereomer however an impurity is present by TLC (EtOAc-ether 3:7). This material and the filtrate is purified by silica gel chromatography separately using EtOAc-dichloromethane (0:100, then 4:96, then 8:98, then 12:88, then 2:8, then 3:7, then 4:6). The material from the two purifications is combined and crystallized from dichloromethane-hexanes-ether to afford in 3 crops 2-methyl-propane-2-sulfinic acid [(S)-1-(6-bromopyridin-3-yl)-propyl]-amide.

Reacting 2-methyl-propane-2-sulfinic acid [1-(6-bromopyridin-3-yl)-but-(E)-ylidene]-amide according to the above method gives the following analog:

2-Methyl-propane-2-sulfinic acid [(S)-1-(6-bromopyridin-3-yl)-butyl]-amide.

To a mixture of 2-methyl-propane-2-sulfinic acid [(S)-1-(6-bromopyridin-3-yl)-propyl]-amide (5.35 g, 16.8 mmol) in methanol (25 mL) is added a solution of 4 N HCl in dioxane (10 mL, 40 mmol). After 2 hour, the mixture is concentrated to near dryness to afford a white solid. The solid is diluted with ether and collected by filtration to afford the title compound.

Reacting 2-methyl-propane-2-sulfinic acid [(S)-1-(6-bromopyridin-3-yl)-butyl]-amide according to the above method gives the following analog:

(S)-1-(6-Bromopyridin-3-yl)-butylamine.

Example 17

Synthesis of (S)-1-(6-Methanesulfonyl-pyridin-3-yl)-propylamine hydrochloride (17)

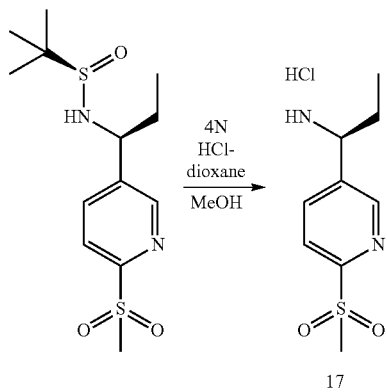 [SMILES: "MeOH" ; CC[C@H](N[S@](=O)C(C)(C)C)c1ccc(S(C)(=O)=O)nc1 ; CC[C@H](N)c1ccc(S(C)(=O)=O)nc1 ; Cl]

17

To a solution of 2-methyl-propane-2-sulfinic acid [(S)-1-(6-methanesulfonyl-pyridin-3-yl)-propyl]-amide (50.0 g, 157 mmol) in methanol (500 mL) is added a 4 N solution of HCl in dioxane (40 mL, 160 mmol). After 1 hour, the mixture is concentrated to near dryness (about 40 mL) and the resulting mixture is diluted with ether (500 mL) and the solid is collected by filtration to afford the title compound.

Example 18

Synthesis of 1-Ethyl-1-(2-methanesulfonyl-thiazol-5-yl)-propylamine hydrochloride (18)

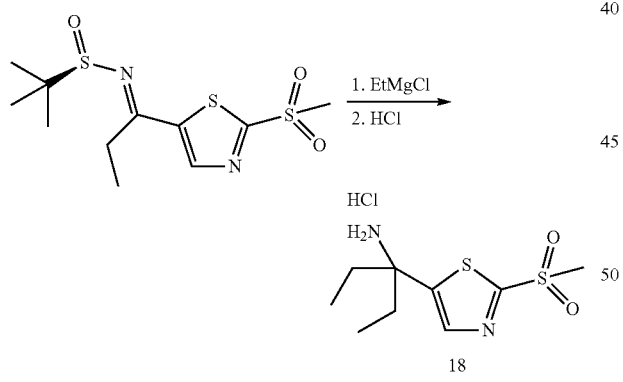

18

To a chilled (0° C.) solution of 2-methyl-propane-2-sulfinic acid [1-(2-methanesulfonyl-thiazol-5-yl)-prop-(Z)-ylidene]-amide (100 mg, 0.3 mmol) in THF (5 mL) is added a 2 M solution of ethylmagnesium chloride (0.19 mL, 0.38 mmol) in diethyl ether. After 2.5 hours, the reaction mixture is quenched with saturated aqueous ammonium chloride (10 mL) and extracted with EtOAc (2×10 mL). The combined organic layers are washed with brine (10 mL), dried over sodium sulfate, filtered and concentrated. The residue is purified by silica gel chromatography eluting with a gradient of 0-10% methanol in dichloromethane to afford an oil. The oil is dissolved in methanol (5 mL) and a 4 N solution of HCl in dioxane (0.5 mL, 2 mmol) is added. After 1 hour, the solution is concentrated to obtain the title compound.

The following compounds are prepared according to methods described in Example 18:

1-(2-Bromopyridin-4-yl)-1-methyl-ethylamine is prepared from 2-methyl-propane-2-sulfinic acid [1-(2-bromopyridin-4-yl)-eth-(E)-ylidene]-amide using methyl magnesium bromide as the Grignard reagent and toluene as solvent;

1-(2-Bromopyridin-4-yl)-1-methyl-propylamine is prepared from 2-methyl-propane-2-sulfinic acid [1-(2-bromopyridin-4-yl)-eth-(E)-ylidene]-amide using toluene as solvent; and 1-(2-Bromopyridin-4-yl)-1-ethyl-propylamine is prepared from 2-methyl-propane-2-sulfinic acid [1-(2-bromopyridin-4-yl)-prop-(E)-ylidene]-amide using toluene as solvent.

Example 19

Synthesis of 1-(2-Methanesulfonyl-pyridin-4-yl)-cyclopropylamine hydrochloride salt (19)

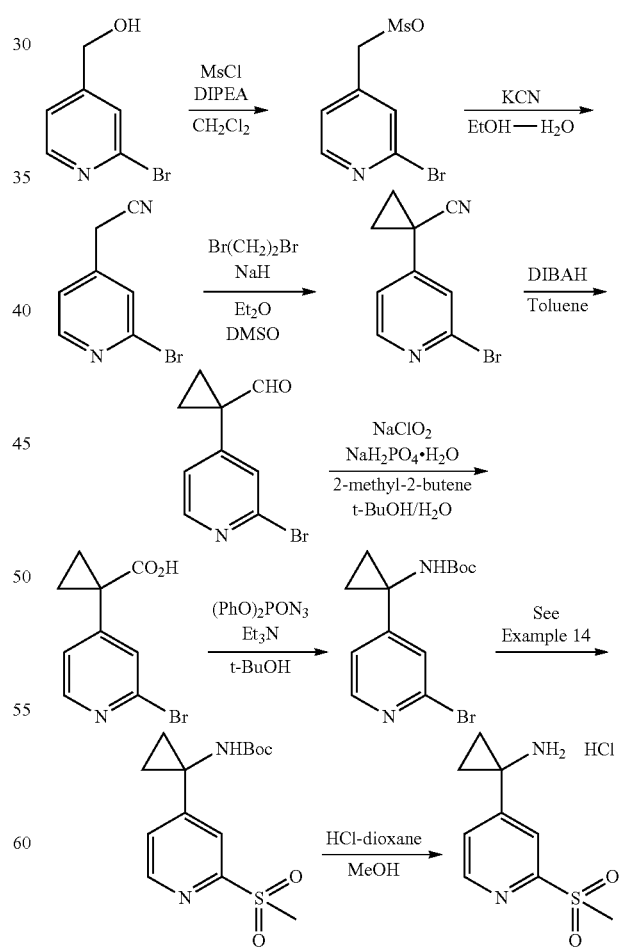

19

To a chilled (0° C.) solution of (2-bromopyridin-4-yl)-methanol (3.00 g, 16.0 mmol) and DIPEA (8.3 mL, 48 mmol) in dichloromethane (30 mL) is added methanesulfonyl chloride (1.30 mL, 16.8 mmol). The resulting mixture is warmed to room temperature. After 1 hour, the mixture is diluted with dichloromethane (20 mL) and washed with saturated aqueous ammonium chloride (3×10 mL), saturated aqueous sodium bicarbonate (10 mL) and brine (10 mL), dried over MgSO$_4$, filtered and concentrated to afford crude methanesulfonic acid 2-bromopyridin-4-ylmethyl ester, which is used without purification.

Methanesulfonic acid 2-bromopyridin-4-ylmethyl ester (4.24 g, 15.9 mmol) is added to a stirred solution of potassium cyanide (1.02 g, 15.1 mmol) in a mixture of ethanol (30 mL) and water (6 mL) at room temperature. After 72 hours, EtOAc (80 mL) and saturated aqueous sodium bicarbonate (40 mL) are added and the organic layer is separated. The organic layer is washed with water (3×40 mL), dried over MgSO$_4$, filtered and concentrated. The resulting residue is purified by silica gel chromatography eluting with a gradient of 0-60% EtOAc in heptane to afford (2-bromopyridin-4-yl)-acetonitrile. MS m/z 197.4, 199.4.

A solution of (2-bromopyridin-4-yl)-acetonitrile (1.20 g, 6.09 mmol) and the 1,2-dibromoethane (0.663 mL, 7.61 mmol) in a mixture of anhydrous Et$_2$O (5 mL) and anhydrous DMSO (1 mL) is added to a suspension of NaH (60% dispersion in mineral oil, 585 mg, 14.6 mmol) in anhydrous DMSO (10 mL) while controlling the resulting exotherm by cooling in a water bath, and the resulting mixture is stirred at room temperature. After 18 hours, water (10 mL) and EtOAc (10 mL) are added, phases are separated and the aqueous layer is extracted with EtOAc (3×10 mL). The combined organic layers are washed with brine (30 mL) and dried over MgSO$_4$, filtered and concentrated. The residue is purified by silica gel chromatography eluting with a gradient of 0-60% EtOAc in heptane to afford 1-(2-bromopyridin-4-yl)-cyclopropanecarbonitrile as a solid. MS m/z 223.4, 225.4.

To a chilled (−78° C.) solution of 1-(2-bromopyridin-4-yl)-cyclopropanecarbonitrile (1.16 g, 5.2 mmol) in toluene (30 mL) is added a 1 M solution of diisobutylaluminum hydride (DIBAH) (10.4 mL) in toluene. The mixture stirred at −78° C. for 1 hour and is then warmed to room temperature. After 1 hour, EtOAc (30 mL) is added, followed by 1 M aqueous solution of H$_2$SO$_4$ (30 mL). The organic phase is separated and the aqueous layer is extracted with EtOAc (3×50 mL). The combined organic layers are dried over MgSO$_4$, filtered and concentrated to afford crude 1-(2-bromopyridin-4-yl)-cyclopropanecarboxaldehyde which is used without purification. MS m/z 226.5, 228.5

A solution of sodium chlorite (368 mg, 3.26 mmol) and sodium dihydrogen phosphate monohydrate (449 mg, 3.26 mmol) in 5 mL of water is added dropwise to a solution of crude 1-(2-bromopyridin-4-yl)-cyclopropanecarboxaldehyde (566 mg, 2.50 mmol) and 2-methyl-2-butene (1.73 mL, 16.3 mmol) in t-butanol (12 mL), and the resulting reaction mixture is stirred at room temperature. After 18 hours, the mixture is concentrated in vacuo, acidified to pH 2 with 1 M aqueous HCl, diluted with brine (25 mL) and extracted with EtOAc (3×50 mL). The combined organic layers are dried over Na$_2$SO$_4$, filtered and concentrated to afford crude 1-(2-bromopyridin-4-yl)-cyclopropanecarboxylic acid which is used without purification.

To a solution of the crude 1-(2-bromopyridin-4-yl)-cyclopropanecarboxylic acid (350 mg, 1.45 mmol) in t-butanol (7 mL) is added diphenylphosphoryl azide (0.312 mL, 1.45 mmol) and triethylamine (0.202 mL, 1.45 mmol) in a pressure vessel. The tube is sealed and the reaction mixture is warmed at 90° C. After 4 hours, the pressure vessel is cooled in an ice-bath, vented and opened. The reaction mixture is concentrated in vacuo. The resulting residue is dissolved in EtOAc (70 mL), washed with saturated aqueous ammonium chloride (70 mL), saturated aqueous sodium bicarbonate (70 mL), dried over MgSO$_4$, filtered and concentrated. The residue is purified by silica gel chromatography eluting with a gradient of 0-50% EtOAc in heptane to afford [1-(2-bromopyridin-4-yl)-cyclopropyl]-carbamic acid tert-butyl ester.

[1-(2-Bromopyridin-4-yl)-cyclopropyl]-carbamic acid tert-butyl ester is converted to [1-(2-methanesulfonyl-pyridin-4-yl)-cyclopropyl]-carbamic acid tert-butyl ester according to methods described in example 14.

To a solution of [1-(2-methanesulfonyl-pyridin-4-yl)-cyclopropyl]-carbamic acid tert-butyl ester (606 mg, 1.94 mmol) in methanol (10 mL) is added a solution of 4 N HCl in dioxane (2 mL, 8 mmol). The mixture stirred overnight and is then concentrated and the residue is triturated with ether-ethanol. The solid is collected by filtration to afford the title compound.

Example 20

Synthesis of 6-Cyano-1-(4-fluorophenyl)-1H-indole-4-carboxylic acid (20)

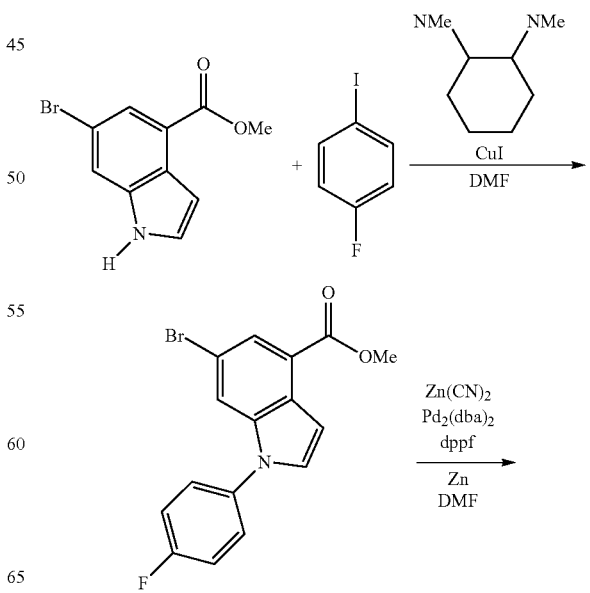

-continued

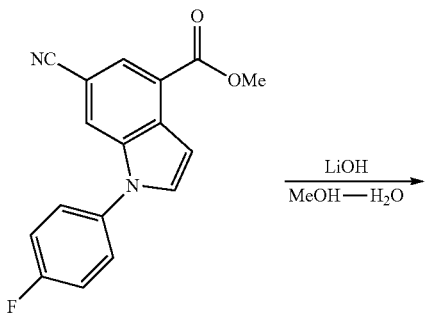

Example 21

Synthesis of 6-Cyano-1-(4-fluorophenyl)-1H-indole-4-carboxylic acid (6-methanesulfonylamino-pyridin-3-ylmethyl)-amide (21)

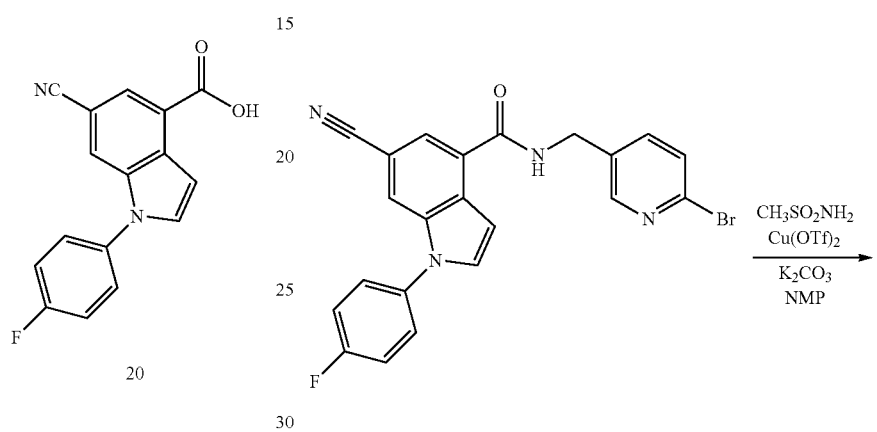

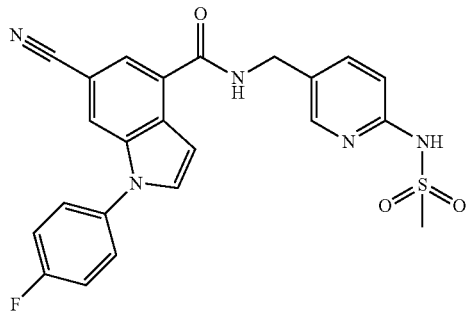

21

A mixture of 6-bromo-1H-indole-4-carboxylic acid methyl ester (2.00 g, 7.84 mmol), CuI (38.0 mg, 0.20 mmol) and $K_2CO_3$ (1.18 g, 8.50 mmol) in a sealed tube is degassed with argon. To the mixture is added 4-fluoroiodobenzene (1.78 g, 8.00 mmol) and trans-N,N'-dimethyl-cyclohexane-1,2-diamine (0.20 g, 1.40 mmol) followed by DMF (25 mL). The reaction mixture is warmed at 120° C. After 3 hours, the reaction is diluted with water and extracted with EtOAc. The combined organic layers are washed with brine, dried over sodium sulfate, filtered and concentrated in vacuo. The residue is purified by silica gel chromatography eluting with EtOAc-hexanes (20:80) to afford 6-bromo-1-(4-fluorophenyl)-1H-indole-4-carboxylic acid methyl ester.

A mixture of 6-bromo-1-(4-fluorophenyl)-1H-indole-4-carboxylic acid methyl ester (1.50 g, 4.30 mmol), $Pd_2(dba)_3$ (393.5 mg, 0.43 mmol), $Zn(CN)_2$ (622 mg, 5.30 mmol), dppf (249.48 mg, 0.45 mmol) and Zn (196.11 mg, 3.00 mmol) in DMF (30 mL) is degassed with argon for 5 minutes. The mixture is warmed at 120° C. After 3 hours, the mixture is diluted with saturated aqueous ammonium chloride (30 mL) and extracted with EtOAc. The combined organic layers are washed with brine, dried over sodium sulfate, filtered and concentrated in vacuo. The residue is purified by silica gel chromatography eluting with EtOAc-hexanes (20:80) to afford 6-cyano-1-(4-fluorophenyl)-1H-indole-4-carboxylic acid methyl ester.

To a stirred solution of 6-cyano-1-(4-fluorophenyl)-1H-indole-4-carboxylic acid methyl ester (0.34 g, 1.2 mmol) in a mixture of MeOH—$H_2O$ (20 mL:5 mL) is added 2 N aqueous NaOH (40 mL) and the mixture is warmed at reflux. After 1 hour, the reaction is cooled to room temperature. The solution is acidified with 2 N aqueous HCl (pH=3). The solid is collected by filtration, washed with $CH_2Cl_2$ and dried to afford the title compound.

To a mixture of 6-cyano-1-(4-fluorophenyl)-1H-indole-4-carboxylic acid (6-bromo-pyridin-3-ylmethyl)-amide (75 mg, 0.17 mmol), methanesulfonamide (81 mg, 0.85 mmol), copper (II) trifluoromethanesulfonate (105 mg, 0.290 mmol), trans-N,N'-dimethylcyclohexane-1,2-diamine (55.2 µL, 0.35 mmol) and potassium carbonate (247 mg, 1.79 mmol) in a sealed tube is added NMP (2.5 mL). The solution is degassed with argon for 3 minutes. The reaction is warmed at 125° C. in a microwave reactor. After 40 minutes, the reaction is diluted with saturated aqueous potassium carbonate (15 mL) and extracted with EtOAc (2×15 mL). The combined organic layers are washed with brine (2×15 mL), dried over magnesium sulfate and concentrated in vacuo. The residue is purified by preparative reversed phase HPLC to afford the title compound.

Example 22

Synthesis of 1-(4-Fluorophenyl)-6-hydroxy-1H-indole-4-carboxylic acid 4-methylsulfamoyl-benzylamide (22)

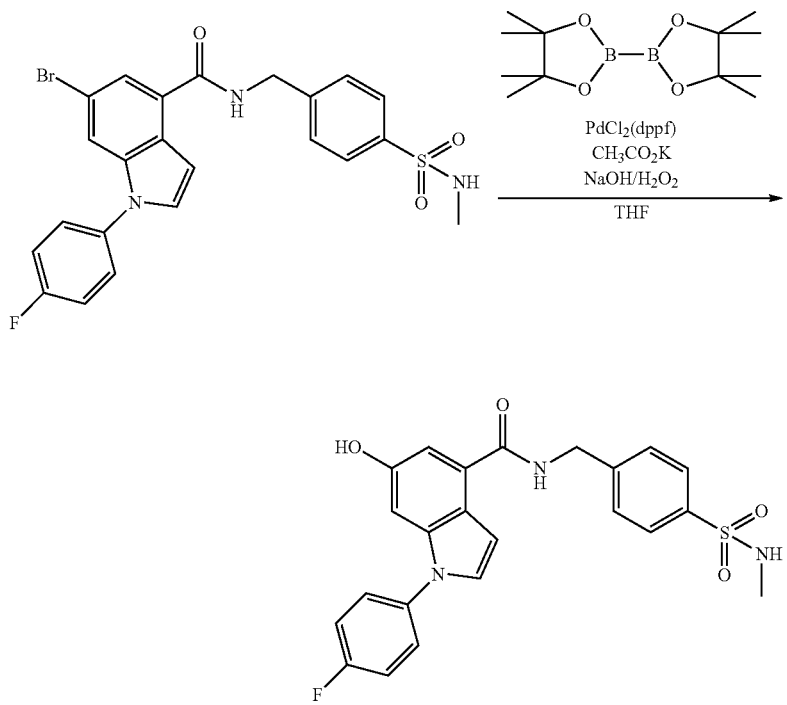

A mixture of 6-bromo-1-(4-fluorophenyl)-1H-indole-4-carboxylic acid 4-methylsulfamoyl-benzylamide (0.1 g, 0.2 mmol), bis(pinacolato)diboron (0.1 g, 0.4 mmol), PdCl$_2$(dppf) (0.04 g, 0.05 mmol), potassium acetate (0.05 g, 0.5 mmol) is charged in a sealed tube with anhydrous THF (7 mL). The solution is warmed at 80° C. for 16 hours. The reaction mixture is cooled to room temperature and quenched with water (15 mL) and diluted with CH$_2$Cl$_2$ (20 mL). The organic layer is separated and washed with brine (10 mL), dried over sodium sulfate and concentrated in vacuo. The residue is dissolved in THF (10 mL), and a solution of 30% H$_2$O$_2$ in water (0.15 mL, 0.5 mmol) and NaOH (0.01 g, 0.3 mmol) is added. The mixture is stirred at 10° C. for 3 hours and is then quenched with water (10 mL) and diluted with CH$_2$Cl$_2$ (20 mL). The organic layer is washed with brine (10 mL) and dried over sodium sulfate and concentrated in vacuo. The residue is purified by reversed-phase HPLC eluting with a gradient of 5-100% CH$_3$CN in water. The desired fractions are combined and diluted with saturated aqueous NaHCO$_3$ (20 mL) and EtOAc (20 mL). The organic layer is separated, dried over sodium sulfate and concentrated to afford the title compound.

Example 23

Synthesis of 1-(4-Fluorophenyl)-6-methanesulfonyl-1H-indole-4-carboxylic acid [(S)-1-(6-methanesulfonyl-pyridin-3-yl)-propyl]-amide (23)

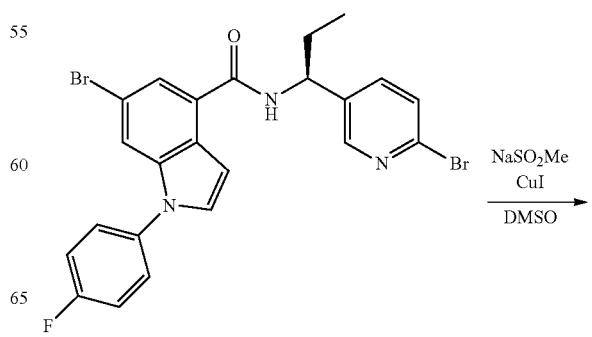

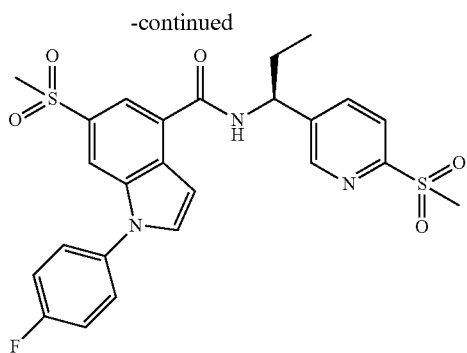

23

A microwave tube is charged with 6-bromo-1-(4-fluorophenyl)-1H-indole-4-carboxylic acid [(S)-1-(6-bromopyridin-3-yl)-propyl]-amide (90.0 mg, 0.170 mmol, prepared as described in Example 5), copper (I) iodine (143 mg, 0.75 mmol) and sodium methanesulfinate (77 mg, 0.75 mmol) in DMSO (20 mL). The tube is capped and the solution is degassed with argon for 3 minutes. The mixture is warmed in a microwave reactor at 130° C. After 40 minutes, the reaction is diluted with saturated aqueous ammonium chloride (100 mL), saturated aqueous sodium bicarbonate (50 mL) and extracted with EtOAc. The combined organic layers are washed with brine, dried over sodium sulfate, filtered and concentrated in vacuo. The crude mixture is purified by reversed-phase HPLC to afford the title compound.

Assessment of Biological Properties

Compounds are assessed for the ability to block the interaction of CCR1 and MIP-1α in a functional cellular assay measuring calcium flux in CCR1 transfected cells.

Method A: Non-adherent cells purchased from Chemicon Corporation (HTS005C), stably expressing recombinant CCR1 and G-alpha-16 are grown in RPMI 1640 medium (Mediatech 10-080-CM) supplemented with 10% heat-inactivated FBS, 0.4 mg/mL Geneticin and penicillin/streptomycin. On the day of the assay, the cells are transferred to a beaker and dye-loaded in bulk using a Fluo-4 NW Calcium Assay Kit with probenecid (Invitrogen F36205) at 0.8E6 cells/mL for 1 hour at room temperature. After 1 hour, they are seeded in a 384-well tissue culture-treated plate at a density of 20,000 cells/well. Appropriately diluted test compound is added to the well to achieve a top concentration of 3,000 nM (diluted 4-fold with 10 doses total). The final concentration of DMSO is 1%. The buffer is HBSS (Invitrogen 14025) with 20 mM HEPES at pH 7.4. The cells are allowed to incubate 1 hour in the dark at room temperature. The plates are transferred to the FLIPR TETRA where MIP-1 alpha in 1% BSA is added at the EC80 final concentration. Wells+/−MIP-1 alpha containing diluted DMSO instead of compound serve as the controls. Intracellular calcium flux is recorded on the FLIPR TETRA, using excitation at 470/495 nm and emission at 515/575 nm. Data are analyzed using Activity Base software.

Method B: Non-adherent cells purchased from Chemicon Corporation (HTS005C), stably expressing recombinant CCR1 and G-alpha-16 are grown in RPMI 1640 medium (Mediatech 10-080-CM) supplemented with 10% FBS, 0.4 mg/mL Geneticin and penicillin/streptomycin. On the day of the assay, the cells are loaded with Calcium 4 dye (Molecular Devices R7448) with Probenecid (Invitrogen P346400) at 8E5 cells/mL for 1 hour at room temperature. After 1 hour, they are seeded in a 384-well tissue culture-treated plate at a density of 20,000 cells/well. Appropriately diluted test compound is added to the well to achieve a top concentration of 3,000 nM (diluted 4-fold with 10 doses total). The final concentration of DMSO is 1%. The buffer is HBSS (Invitrogen 14025) with 20 mM HEPES at pH 7.4. The cells incubate 30 minutes at 37 C and then 30 minutes at room temperature. The plates are transferred to the HAMAMATSU FDSS6000 where MIP-1alpha in 1% BSA is added at the EC80 final concentration. All plates must be read within 4 hours of the start of dye-loading. Wells+/−MIP-1alpha containing diluted DMSO instead of compound serve as the controls. Data are analyzed using Activity Base software.

In general, the preferred potency range ($IC_{50}$) of compounds in the above assay is between 0.1 nM to 3 μM, and the most preferred potency range is 0.1 nM to 50 nM.

Representative compounds of the invention have been tested in the above assay and have shown activity as CCR1 antagonists, this represents another embodiment of the invention.

TABLE II

| Name | Method A $IC_{50}$ (nM) | Method B $IC_{50}$ (nM) |
|---|---|---|
| 3-(4-Fluorophenyl)-imidazo[1,5-a]pyridine-8-carboxylic acid 3-trifluoromethyl-benzylamide | 18 | |
| 3-(3,4-Dichlorophenyl)-imidazo[1,5-a]pyridine-8-carboxylic acid 3-trifluoromethyl-benzylamide | 810 | |
| 3-(4-Fluorophenyl)-imidazo[1,5-a]pyridine-8-carboxylic acid 3-methanesulfonyl-benzylamide | 305 | |
| 3-(4-Fluorophenyl)-imidazo[1,5-a]pyridine-8-carboxylic acid (2-bromopyridin-4-ylmethyl)-amide | 11 | |
| 3-(4-Fluorophenyl)-imidazo[1,5-a]pyridine-8-carboxylic acid (6-bromopyridin-3-ylmethyl)-amide | 428 | |
| 3-(4-Fluorophenyl)-imidazo[1,5-a]pyridine-8-carboxylic acid (6-methanesulfonyl-pyridin-3-ylmethyl)-amide | 568 | |
| 3-(4-Fluorophenyl)-imidazo[1,5-a]pyridine-8-carboxylic acid (2-methanesulfonyl-pyridin-4-ylmethyl)-amide | 285 | |
| 3-(4-Fluorophenyl)-imidazo[1,5-a]pyridine-8-carboxylic acid [1-(6-methanesulfonyl-pyridin-3-yl)-butyl]-amide | 7 | |
| 3-(4-Fluorophenyl)-imidazo[1,5-a]pyridine-8-carboxylic acid [(S)-1-(6-bromopyridin-3-yl)-propyl]-amide | | 29 |
| 3-(4-Fluorophenyl)-imidazo[1,5-a]pyridine-8-carboxylic acid [(S)-1-(6-methanesulfonyl-pyridin-3-yl)-propyl]-amide | | 17 |
| 3-(4-Fluorophenyl)-imidazo[1,5-a]pyridine-8-carboxylic acid [(S)-1-(2-methanesulfonyl-pyridin-4-yl)-propyl]-amide | | 2 |

TABLE II-continued

| Name | Method A IC$_{50}$ (nM) | Method B IC$_{50}$ (nM) |
|---|---|---|
| 3-(4-Fluorophenyl)-imidazo[1,2-a]pyridine-8-carboxylic acid [(S)-1-(6-bromopyridin-3-yl)-butyl]-amide | | 1103 |
| 3-(4-Fluorophenyl)-imidazo[1,2-a]pyridine-8-carboxylic acid [(S)-1-(6-bromopyridin-3-yl)-propyl]-amide | | 1336 |
| 1-(4-Fluorophenyl)-imidazo[1,5-a]pyridine-5-carboxylic acid [(S)-1-(6-bromopyridin-3-yl)-propyl]-amide | | 96 |
| 1-(4-Fluorophenyl)-imidazo[1,5-a]pyridine-5-carboxylic acid [(S)-1-(6-methanesulfonyl-pyridin-3-yl)-propyl]-amide | | 19 |
| 1-(4-Fluorophenyl)-1H-pyrazolo[3,4-d]pyridazine-4-carboxylic acid (2-methanesulfonyl-pyridin-4-ylmethyl)-amide | | 91 |
| 1-(4-Fluorophenyl)-1H-pyrazolo[3,4-d]pyridazine-4-carboxylic acid [(S)-1-(2-methanesulfonyl-pyridin-4-yl)-propyl]-amide | | 3 |
| 1-(4-Fluorophenyl)-1H-pyrazolo[3,4-d]pyridazine-4-carboxylic acid [(S)-1-(2-methanesulfonyl-pyridin-4-yl)-ethyl]-amide | | 57 |
| 1-(4-Fluorophenyl)-1H-pyrazolo[3,4-d]pyridazine-4-carboxylic acid [(S)-1-(6-methanesulfonyl-pyridin-3-yl)-propyl]-amide | | 44 |
| 3-(4-Fluorophenyl)-imidazo[1,5-a]pyrazine-8-carboxylic acid [(S)-1-(2-methanesulfonyl-pyridin-4-yl)-propyl]-amide | | 30 |
| 3-(4-Fluorophenyl)-imidazo[1,5-a]pyrazine-8-carboxylic acid [(S)-1-(2-methanesulfonyl-pyridin-4-yl)-butyl]-amide | | 5 |
| 3-(4-Fluorophenyl)-imidazo[1,5-a]pyrazine-8-carboxylic acid (2-methanesulfonyl-pyridin-4-ylmethyl)-amide | | 600 |
| 3-(4-Fluorophenyl)-imidazo[1,5-a]pyrazine-8-carboxylic acid [1-(2-bromopyridin-4-yl)-1-methyl-ethyl]-amide | | 1100 |
| 3-(4-Fluorophenyl)-imidazo[1,5-a]pyrazine-8-carboxylic acid [1-(2-methanesulfonyl-pyridin-4-yl)-cyclopropyl]-amide | | 410 |
| 3-(4-Fluorophenyl)-imidazo[1,5-a]pyrazine-8-carboxylic acid [(S)-1-(5-methanesulfonyl-pyridin-3-yl)-butyl]-amide | | 6 |
| 1-(4-Fluorophenyl)-1H-pyrrolo[2,3-c]pyridine-4-carboxylic acid [(S)-1-(6-methanesulfonyl-pyridin-3-yl)-propyl]-amide | | 21 |
| 1-(4-Fluorophenyl)-1H-pyrrolo[2,3-c]pyridine-4-carboxylic acid 3-methanesulfonyl-benzylamide | | 565 |
| 1-(4-Fluorophenyl)-1H-pyrrolo[2,3-c]pyridine-4-carboxylic acid [(S)-1-(2-methanesulfonyl-pyridin-4-yl)-propyl]-amide | | 2 |
| 1-(4-Fluorophenyl)-1H-pyrrolo[2,3-c]pyridine-4-carboxylic acid (2-methanesulfonyl-pyridin-4-ylmethyl)-amide | | 455 |
| 1-(4-Fluorophenyl)-1H-pyrrolo[2,3-c]pyridine-4-carboxylic acid [(S)-1-(5-methanesulfonyl-pyridin-3-yl)-propyl]-amide | | 2 |
| 1-(4-Fluorophenyl)-1H-pyrrolo[2,3-c]pyridine-4-carboxylic acid [(S)-1-(2-methanesulfonyl-pyridin-4-yl)-ethyl]-amide | | 45 |
| 1-(4-Fluorophenyl)-1H-pyrrolo[2,3-c]pyridine-4-carboxylic acid [(S)-1-(2-methanesulfonyl-thiazol-5-yl)-propyl]-amide | | 23 |
| 6-Cyano-1-(4-fluorophenyl)-1H-indole-4-carboxylic acid 4-(1-methyl-piperidin-4-ylsulfamoyl)-benzylamide | | 18 |
| 6-Cyano-1-(4-fluorophenyl)-1H-indole-4-carboxylic acid 3-methanesulfonyl-benzylamide | | 2 |
| 6-Cyano-1-(4-fluorophenyl)-1H-indole-4-carboxylic acid (6-methanesulfonyl-pyridin-3-ylmethyl)-amide | | 4 |
| 6-Cyano-1-(4-fluorophenyl)-1H-indole-4-carboxylic acid (6-methanesulfonylamino-pyridin-3-ylmethyl)-amide | | 4 |
| 1-(4-Fluorophenyl)-6-hydroxy-1H-indole-4-carboxylic acid 4-methylsulfamoyl-benzylamide | | 1400 |
| 1-(4-Fluorophenyl)-6-methanesulfonyl-1H-indole-4-carboxylic acid [(S)-1-(6-methanesulfonyl-pyridin-3-yl)-propyl]-amide | | 260 |
| 6-Cyano-1-(4-fluorophenyl)-1H-indole-4-carboxylic acid [1-(2-methanesulfonyl-pyridin-4-yl)-cyclopropyl]-amide | | 0.8 |

Method of Use

The compounds of the invention are effective antagonists of the interactions between CCR1 and its chemokine ligands and thus inhibit CCR1-mediated activity. Therefore, in one embodiment of the invention, there is provided methods of treating autoimmune disorders using compounds of the invention. In another embodiment, there is provided methods of treating inflammatory disorders using compounds of the invention.

Without wishing to be bound by theory, by antagonizing the interactions between CCR1 and its chemokine ligands, the compounds block chemotaxis of pro-inflammatory cells including monocytes, macrophages dendritic cells, eosinophils, and T cells (TH1) cells and other CCR1 positive cells to inflamed tissues and thereby ameliorate the chronic inflammation associated with autoimmune diseases. Thus, the inhibition of CCR1 activity is an attractive means for preventing and treating a variety of autoimmune disorders, including inflammatory diseases, autoimmune diseases, organ (Horuk et al. (2001) *JBC* 276 p. 4199) and bone marrow transplant rejection and other disorders associated with an influx of pro-inflammatory cells. For example, the compounds of the invention may be used to prevent or treat acute or chronic inflammation, allergies, contact dermatitis, psoriasis, rheumatoid arthritis, multiple sclerosis, type 1 diabetes, inflammatory bowel disease, Guillain-Barre syndrome, Crohn's disease, ulcerative colitis, graft versus host disease (and other forms of organ or bone marrow transplant rejection), Alzheimer's disease (Halks-Miller et al. (2003) *Ann Neurol* 54 p. 638), *Asthma* (Jouber et al. (2008) *J. Immun* 180 p. 1268), chronic kidney disease (Topham et al. (1999) *J. Clin. Invest.* 104 p. 1549), sepsis (Ile et al. (2007) *Am J. Physio* 292 p. G1173), autoimmune myocarditis (Futamats et al. (2006) *J Mol Cell Cardiology* 40 p. 853), multiple myeloma (Blood (2001) 97 pp 3349-3353), COPD (*Expert Opin. Investig. Drugs* (2005) 14 pp 785-796) and systemic lupus erythematosus. In particular, the compounds may be used to prevent or treat rheumatoid arthritis and multiple sclerosis. Other disorders associated with the trafficking of pro-inflammatory cells will be evident to those of ordinary skill in the art and can also be treated with the compounds and compositions of this invention.

For treatment of the above-described diseases and conditions, a therapeutically effective dose will generally be in the range from about 0.01 mg/kg to about 100 mg/kg of body weight per dosage of a compound of the invention; preferably, from about 0.1 mg/kg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems*, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

The invention claimed is:

1. A compound of the formula (I)

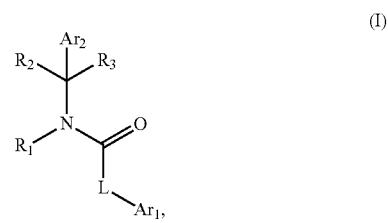

wherein:

L is selected from

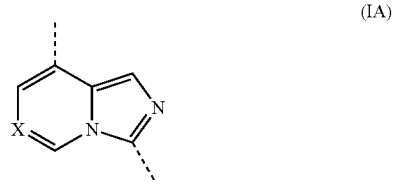

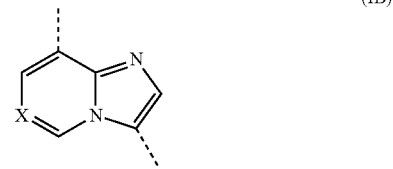

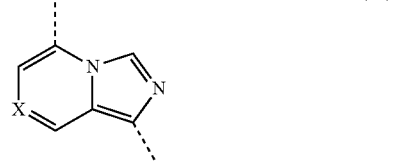

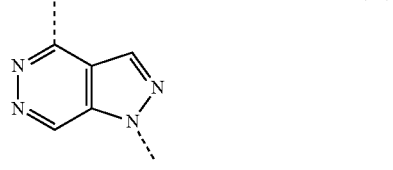

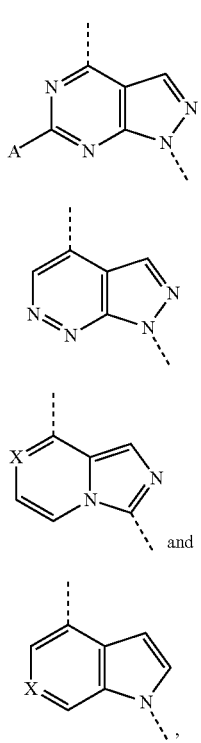

(IE), (IF), (IG), (IH)

wherein Ar₁ is connected to the 5-member ring within L and wherein —C(O)N(R₁)CR₂R₃Ar₂ is connected to the 6-member ring contained within L;

X is N or C-A;

A is selected from hydrogen, methyl, trifluoromethyl, halogen, hydroxyl, cyano and $C_1$-$C_5$ alkylthio wherein the sulfur atom is optionally oxidized to a sulfoxide or sulfone;

Ar₁ is carbocycle, heteroaryl or heterocyclyl each optionally substituted by one to three $R_a$;

Ar₂ is carbocycle, heteroaryl or heterocyclyl, each optionally substituted by one to three $R_b$;

R₁ is hydrogen, $C_{1-6}$ alkyl or $C_{1-6}$ alkoxy$C_{1-6}$ alkyl;

R₂, R₃ are each independently hydrogen, $C_{1-6}$ alkyl or $C_{1-6}$ alkenyl, wherein the $C_{1-6}$ alkyl or alkenyl is optionally partially or fully halogenated or substituted with one to three groups independently selected from cyano, $C_{1-6}$ alkoxy, hydroxyl, —CO₂$C_{1-6}$ alkyl, —C(O)N($R_e$)($R_f$), —N($R_e$)($R_f$) and heterocyclyl optionally substituted by oxo; or R₂ and R₃ together with the carbon atom they are commonly attached to form a $C_3$-$C_6$ cycloalkyl ring;

$R_a$ is $C_{1-6}$ alkyl, $C_{3-10}$ cycloalkyl, $C_{1-6}$ alkoxy, $C_{1-6}$ alkylthio, $C_{1-6}$ alkylsulfonyl, $C_{1-6}$ alkoxycarbonyl, amino, mono- or di-$C_{1-6}$ alkylamino, $C_{3-6}$ cycloalkylamino, $C_{1-6}$ alkylaminocarbonyl, $C_{1-6}$ acyl, $C_{1-6}$ acylamino, $C_{1-6}$ dialkylaminocarbonyl, hydroxyl, halogen, cyano, nitro, oxo, $R_4$—S(O)$_m$—NH—, $R_4$—NH—S(O)$_m$—, aryl or carboxyl;

$R_b$ is hydroxyl, carboxyl, halogen, —(CH₂)$_n$—CN, —(CH₂)$_n$—CO₂$C_{1-6}$alkyl, nitro, $C_{1-6}$ alkyl, $C_{2-6}$ alkenyl, $C_{2-6}$ alkynyl, $C_{3-10}$ cycloalkyl, $C_{1-6}$ alkoxy, $C_{1-6}$alkylC(O)—, —(CH₂)$_n$—NR$_c$R$_d$, $R_4$—S(O)$_m$(CH₂)$_{0-1}$—, $R_4$—S(O)$_m$—NR$_e$—, $R_4$—NR$_e$—S(O)$_m$(CH₂)$_{0-1}$—, —NR$_f$—C(O)—R$_e$, —(CH₂)$_y$—C(O)—(CH₂)$_n$—NR$_c$R$_d$, heterocyclyl, aryl or heteroaryl, each $R_b$ where possible is optionally halogenated or substituted with 1 to 3$C_{1-6}$ alkyl, hydroxyl, $C_{1-6}$ acyl, $C_{1-6}$ alkoxycarbonyl, $C_{1-6}$ alkyl-S(O)$_m$—, aryl or carboxyl;

each $R_c$, $R_d$ are independently hydrogen, $C_{1-6}$ alkyl, $C_{1-6}$ acyl, $C_{3-10}$ cycloalkyl, $C_{1-6}$ alkoxy, hydroxy$C_{1-6}$ alkyl, cyano-$C_{1-6}$ alkyl, $C_{1-6}$ alkyl$C_{1-6}$ alkoxy, $C_{1-6}$ alkylsulfonyl, $C_{1-6}$ alkoxycarbonyl$C_{0-3}$alkyl, —(CH₂)$_n$—C(O)—NR$_e$R$_f$ or —(CH₂)$_n$—NR$_e$R$_f$;

each R$_e$, R$_f$ are independently hydrogen, $C_{1-6}$ alkyl, $C_{3-10}$ cycloalkyl, $C_{1-6}$ alkoxy, $C_{1-6}$ alkoxy$C_{1-6}$alkyl, mono- or di$C_{1-6}$alkylamino$C_{1-6}$alkyl, hydroxy$C_{1-6}$ alkyl or $C_{1-6}$ acyl;

R₄ is hydrogen, $C_{1-6}$ alkyl, $C_{3-6}$cycloalkyl, heterocyclyl (CH₂)$_{0-1}$, mono- or di-$C_{1-6}$ alkylamino, mono- or di-$_{1-6}$ alkylamino(CH₂)$_{2-3}$N(R$_e$)—, aryl or heteroaryl each optionally substituted with 1 to 3$C_{1-6}$ alkyl, $C_{3-6}$cycloalkyl, $C_{1-6}$alkoxy, halogen, hydroxyl, oxo, carboxyl, —C(O)NR$_e$R$_f$, amino, mono- or di-$C_{1-6}$ alkylamino, $C_{1-6}$ alkoxycarbonyl or $C_{1-6}$ acylamino;

each n, y are independently 0-3;

each m is independently 0-2;

or a pharmaceutically acceptable salt thereof.

2. The compound according to claim 1, and wherein
X is N or C-A;
A is selected from hydrogen, methyl, trifluoromethyl, hydroxyl, cyano and $C_1$-$C_5$ alkylthio wherein the sulfur atom is optionally oxidized to a sulfoxide or sulfone;
Ar₁ is phenyl, cyclohexyl or tetrahydropyranyl each optionally substituted by one to three $R_a$;
Ar₂ is phenyl, pyridinyl, pyrimidinyl, thiophenyl, thiazolyl, oxazolyl, pyrazolyl, imidazolyl, cyclohexyl, piperidinyl, morpholinyl or piperazinyl, each optionally substituted by one to three $R_b$;
R₁ is hydrogen;
R₂, R₃ are each independently hydrogen or $C_{1-6}$ alkyl, wherein the $C_{1-6}$ alkyl is optionally partially or fully halogenated or substituted with one to three groups independently selected from cyano, $C_{1-6}$ alkoxy and hydroxyl; or
R₂ and R₃ together with the carbon atom they are commonly attached to form a $C_{3-4}$ cycloalkyl ring;
$R_a$ is $C_{1-6}$ alkyl, hydroxyl, halogen, cyano or nitro;
$R_b$ is hydroxyl, carboxyl, halogen, $C_{1-6}$ alkyl, $C_{1-6}$ alkoxy, $C_{1-6}$alkylC(O)—, $R_4$—S(O)$_m$(CH₂)$_{0-1}$—, $R_4$—S(O)$_m$—NR$_e$— or $R_4$—NR$_e$—S(O)$_m$(CH₂)$_{0-1}$—, each $R_b$ where possible is optionally halogenated or substituted with 1 to 3$C_{1-6}$ alkyl, hydroxyl, $C_{1-6}$ acyl, $C_{1-6}$ alkoxycarbonyl, $C_{1-6}$ alkyl-S(O)$_m$— or carboxyl;
each R$_e$ is hydrogen, $C_{1-6}$ alkyl, $C_{3-10}$ cycloalkyl, $C_{1-6}$ alkoxy, $C_{1-6}$ alkoxy$C_{1-6}$alkyl, mono- or di$C_{1-6}$alkylamino$C_{1-6}$alkyl, hydroxy$C_{1-6}$ alkyl or $C_{1-6}$ acyl;
R₄ is hydrogen, $C_{1-6}$ alkyl, $C_{3-6}$cycloalkyl, piperidinyl, morpholinyl, tetrahydropyranyl, pyrrolidinyl, mono- or di-$C_{1-6}$ alkylamino, mono- or di-$_{1-6}$alkylamino(CH₂)$_{2-3}$N(R$_e$)—, aryl or heteroaryl each optionally substituted with 1 to 3$C_{1-6}$ alkyl, $C_{3-6}$cycloalkyl, carboxyl;
or a pharmaceutically acceptable salt thereof.

3. The compound according to claim 2, and wherein
X is N or C-A;
A is selected from hydrogen and cyano;
Ar₁ is phenyl is substituted by one to two $R_a$;
Ar₂ is phenyl, pyridinyl, or thiazolyl, each optionally substituted by one to two $R_b$;
R₂, R₃ are each independently hydrogen or $C_{1-3}$ alkyl; or
R₂ and R₃ together with the carbon atom they are commonly attached to form a $C_3$ cycloalkyl ring;
$R_a$ is $C_{1-6}$ alkyl, halogen or cyano;

$R_b$ is halogen, $C_{1-3}$ alkyl, $R_4$—S(O)$_m$(CH$_2$)$_{0-1}$—, $R_4$—S(O)$_m$—NR$_e$—, or $R_4$—NR$_e$—S(O)$_m$(CH$_2$)$_{0-1}$—, each $R_b$ where possible is optionally halogenated;

each $R_e$ is hydrogen;

$R_4$ is $C_{1-6}$ alkyl or piperidinyl each optionally substituted with 1 to 3 $C_{1-3}$ alkyl;

each m is 2;

or a pharmaceutically acceptable salt thereof.

4. The compound according to claim 3, and wherein $R_a$ is —F;

$R_b$ is $R_4$—S(O)$_2$(CH$_2$)$_{0-1}$—, $R_4$—S(O)$_2$—NR$_e$—, or $R_4$—NR$_e$—S(O)$_2$(CH$_2$)$_{0-1}$—, CF$_3$ or Br;

$R_4$ is $C_{1-3}$ alkyl or piperidinyl each optionally substituted with —CH$_3$;

or a pharmaceutically acceptable salt thereof.

5. The compound according to claim 4, and wherein L is selected from

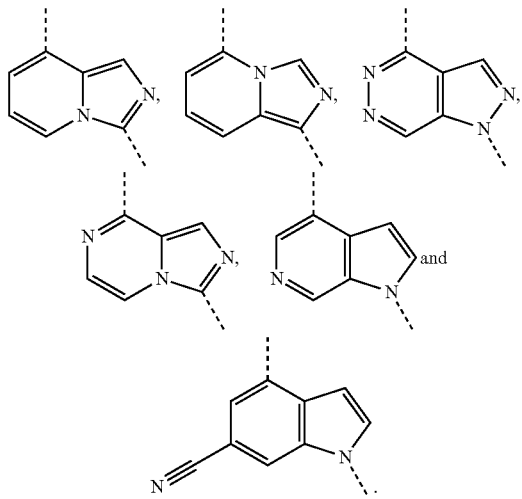

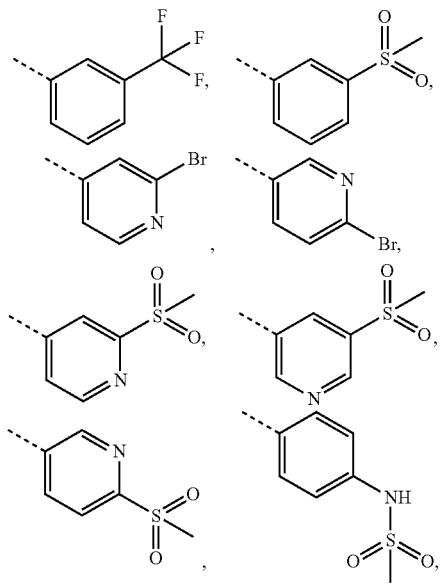

or a pharmaceutically acceptable salt thereof.

6. The compound according to claim 5, and wherein Ar$_2$ is

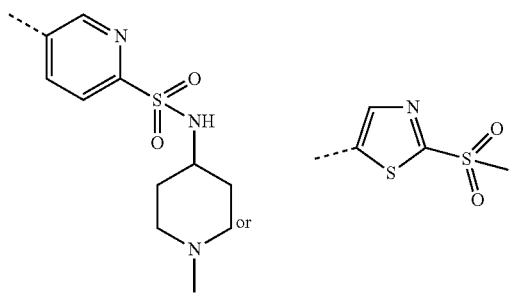

-continued or a pharmaceutically acceptable salt thereof.

7. A compound chosen from

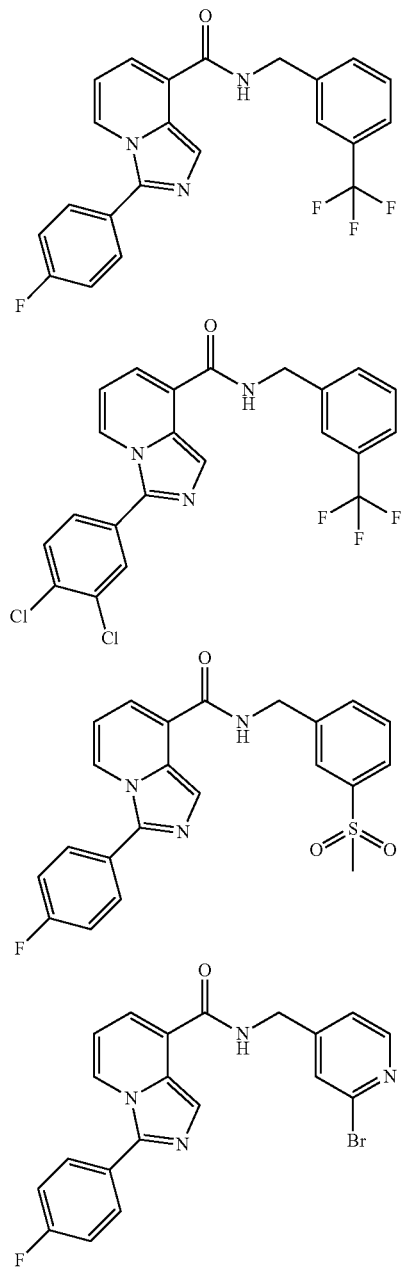

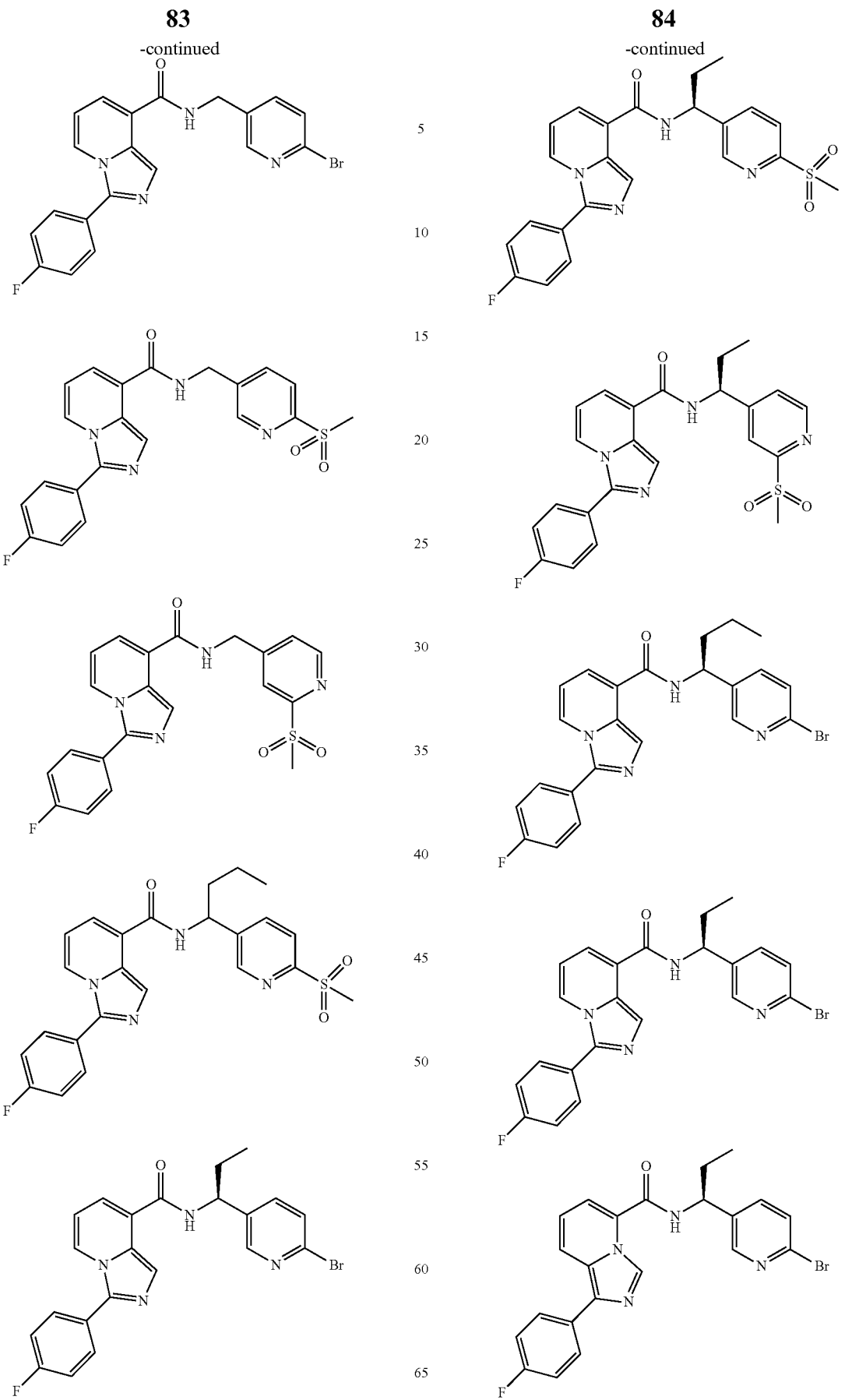

85
-continued
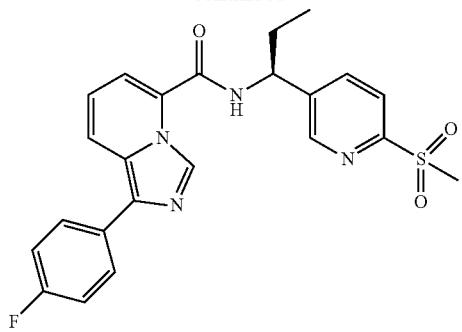
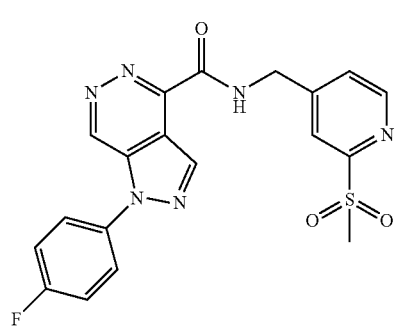
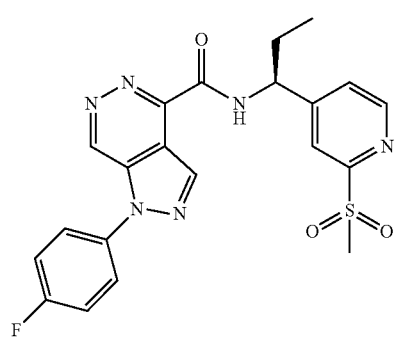
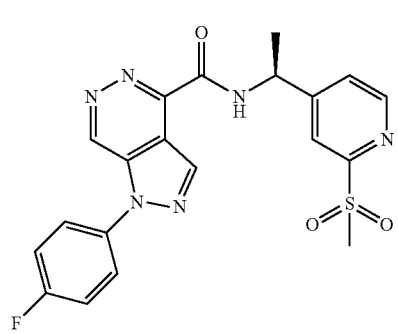
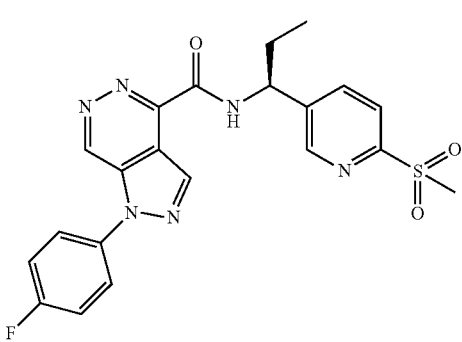
86
-continued
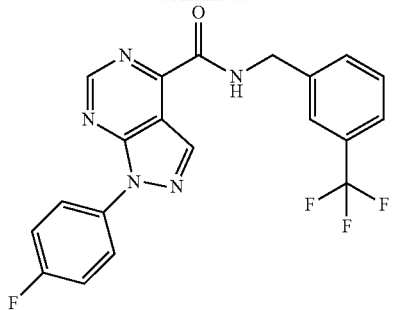
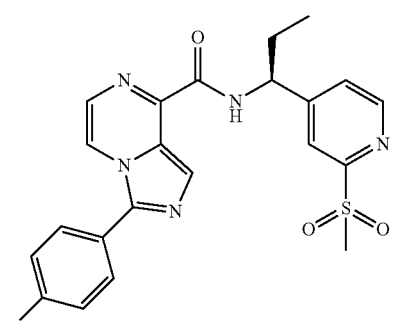
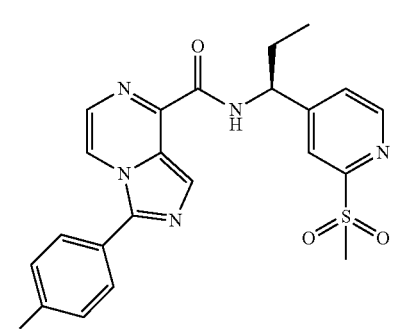
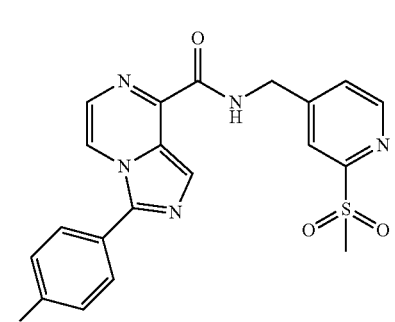
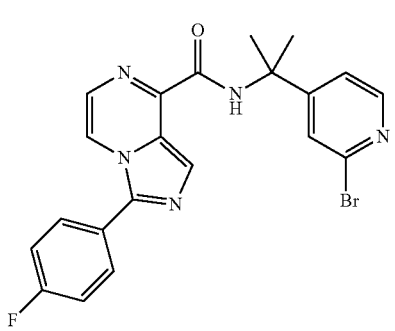

87
-continued
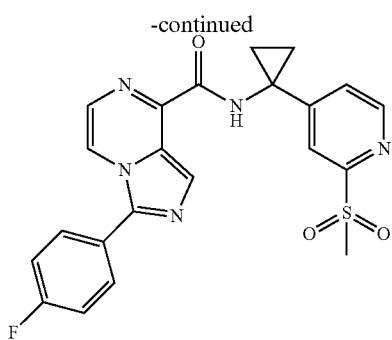
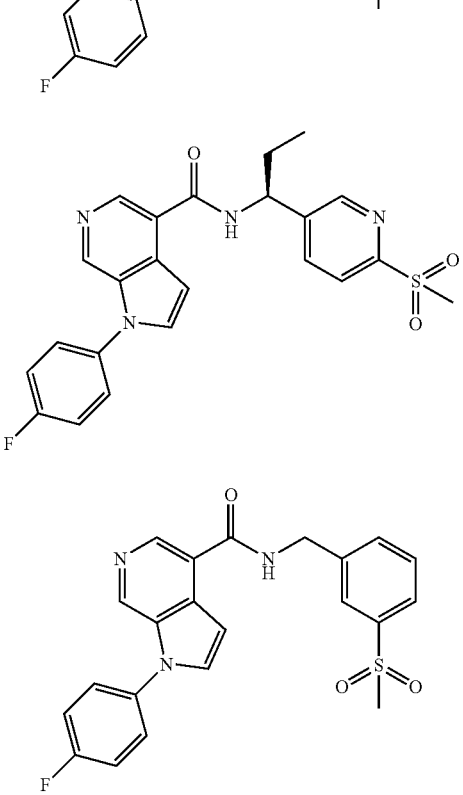
88
-continued
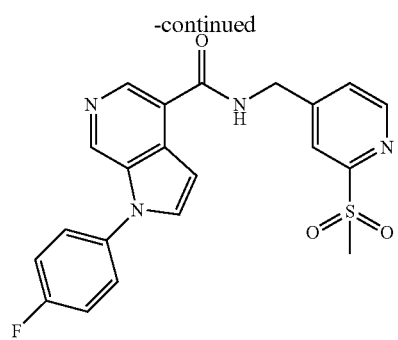
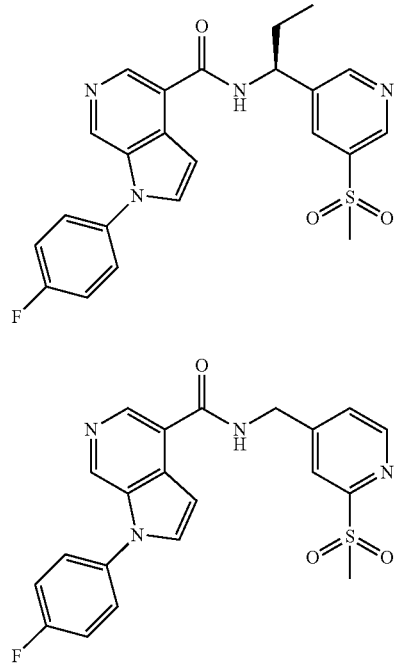
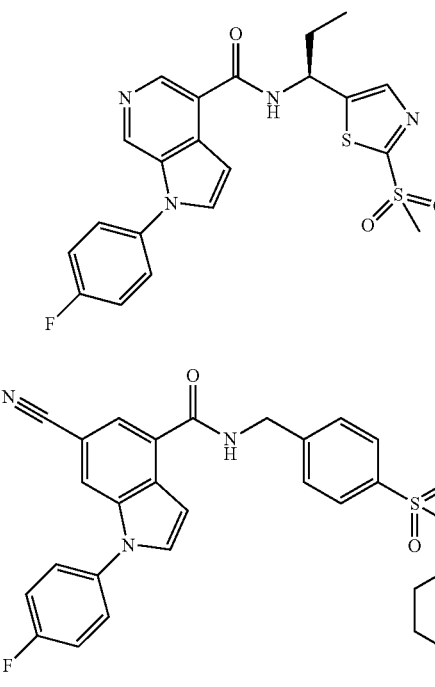
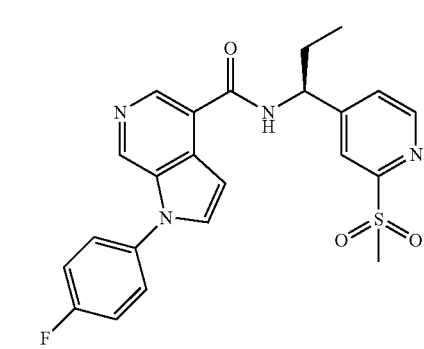

-continued
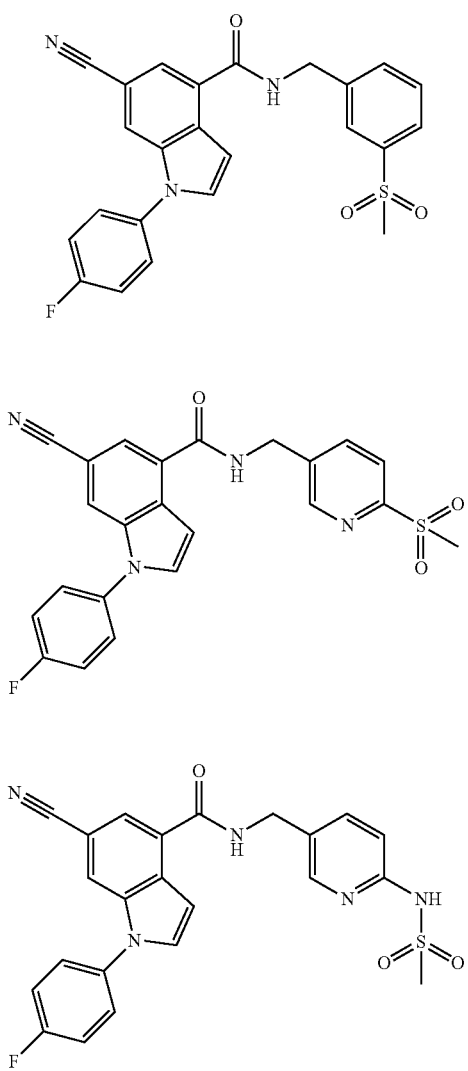
-continued
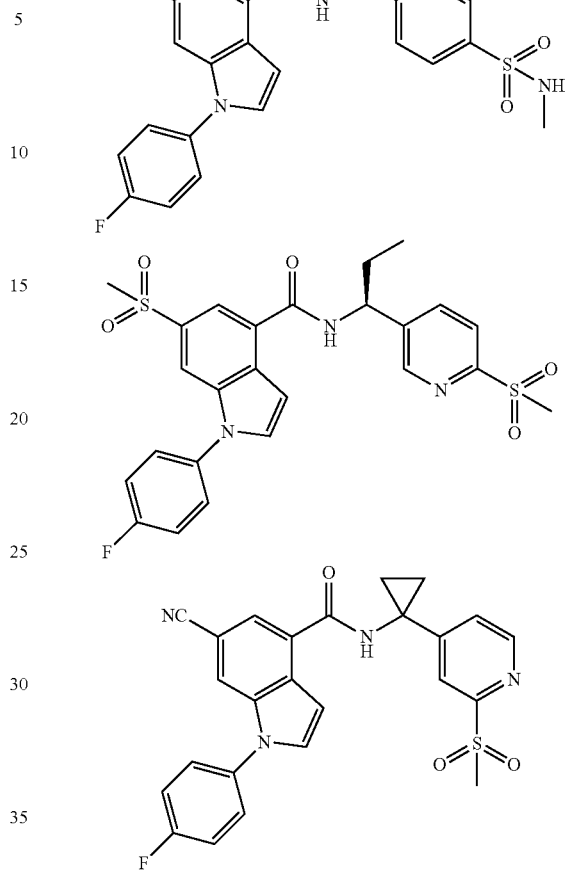
or a pharmaceutically acceptable salts thereof.
8. A pharmaceutical composition comprising a pharmaceutically effective amount of a compound according to claim 1 and one or more acceptable pharmaceutically carriers and/or adjuvants.
* * * * *